US010428119B2

(12) United States Patent
Pastan et al.

(10) Patent No.: US 10,428,119 B2
(45) Date of Patent: Oct. 1, 2019

(54) *PSEUDOMONAS* EXOTOXIN A WITH LESS IMMUNOGENIC T CELL AND/OR B CELL EPITOPES

(71) Applicant: **

(56) References Cited

U.S. PATENT DOCUMENTS

| | | | |
|---|---|---|---|
| 7,470,775 B2 | 12/2008 | Pastan et al. | |
| 7,521,054 B2 | 4/2009 | Pastan et al. | |
| 7,541,034 B1 | 6/2009 | Fitzgerald et al. | |
| 8,871,906 B2* | 10/2014 | Pastan .................. | C07K 14/21 424/260.1 |
| 8,932,586 B2 | 1/2015 | Jones et al. | |
| 2002/0197266 A1 | 12/2002 | Debinski | |
| 2007/0189962 A1 | 8/2007 | Pastan et al. | |
| 2008/0193976 A1 | 8/2008 | Harding | |
| 2009/0142341 A1 | 6/2009 | Pastan et al. | |
| 2010/0291150 A1 | 11/2010 | Harding | |

FOREIGN PATENT DOCUMENTS

| | | |
|---|---|---|
| EP | 0 239 400 B1 | 8/1994 |
| GB | 2 188 638 A | 10/1987 |
| WO | WO 1987/002671 A1 | 5/1987 |
| WO | WO 1993/011161 A1 | 6/1993 |
| WO | WO 1998/045322 A2 | 10/1998 |
| WO | WO 1999/051643 A1 | 10/1999 |
| WO | WO 2003/027135 A2 | 4/2003 |
| WO | WO 2005/052006 A2 | 6/2005 |
| WO | WO 2005/052007 A1 | 6/2005 |
| WO | WO 2006/037960 A2 | 4/2006 |
| WO | WO 2007/016150 A2 | 2/2007 |
| WO | WO 2007/031741 A1 | 3/2007 |
| WO | WO 2007/085470 A2 | 8/2007 |
| WO | WO 2007/103522 A2 | 9/2007 |
| WO | WO 2009/032954 A1 | 3/2009 |
| WO | WO 2011/032022 A1 | 3/2011 |
| WO | WO 2012/170617 A1 | 12/2012 |
| WO | WO 2013/040141 A1 | 3/2013 |

OTHER PUBLICATIONS

Mazor et al., "Dual B- and T-cell de-immunization of recombinant immunotoxin targeting mesothelin with high cytotoxic activity," *Oncotarget*, 7(21): 29916-29926 (2016).

Mazor et al., "Recombinant Immunotoxin with T Cell Epitope Mutations that Greatly Reduce Immunogenicity for Treatment of Mesothelin Expressing Tumors," *Mol. Cancer Ther.*, 14(12): 2789-2796 (2015).

Chain A, Pseudomonas Aeruginosa Exotoxin A, Wild Type, from https://www.ncbi.nlm.nih.gov/protein/1IKQ_A, pp. 1-5, Oct. 18, 2012.

Mazor et al., "Recombinant immunotoxin for cancer treatment with low immunogenicity by identification and silencing of human T-cell epitopes," and Supporting Information, *Proc. Natl. Acad. Sci. U.S.A.*, 111(23): 8571-8576 (May 5, 2014).

Arndt et al, "Helix-stabilized Fv (hsFv) antibody fragments: substituting the constant domains of a Fab fragment for a heterodimeric coiled-coil domain," *J. Mol. Niol.*, 312(1), 221-8 (2001).

Brinkmann et al. "A recombinant immunotoxin containing a disulfide-stabilized fv fragment," *PNAS*, 90(16), 7538-42 (1993).

Davies et al., "Antibody VH Domains as Small Recognition Units," *Biotechnology*, 13, 475-9 (1995).

Debinski et al., "An Immunotoxin with Increased Activity and Homogeneity Produced by Reducing the Number of Lysine Residues in Recombinant Pseudomonas Exotoxin," Bioconjug. Chem., 5: 40-46 (1994).

Definition of moiety, from http://dictionary.reference.com/browse/moiety, pp. 3, accessed Aug. 26, 2010.

Duckert et al., "Prediction of proprotein convertase cleavage sites," *Protein Eng. Des. Sel.*, 17(1), 107-12 (2004).

Frankel et al., "Targeted toxins," *Clin. Cancer Res.*, 6(2), 326-34 (2000).

Genbank Accession No. ZP_06879957 "Exotoxin a precursor [pseudomonas aeruginosa PAb1]" (Dec. 10, 2010).

Geneseq Database Accession No. AAU96810 (Aug. 13, 2002).

Geneseq Database EBI Accession No. AYM76300 (Feb. 3, 2011).

Ghahroudi et al., "Selection and identification of single domain antibody fragments from camel heavy-chain antibodies," *FEBS Lett.*, 414, 521-526 (1997).

Hansen et al., "A recombinant immunotoxin targeting CD22 with low immunogenicity, low nonspecific toxicity, and high antitumor activity in mice," *J. Immunother.*, 33(3), 297-304 (2010).

Harmsen et al., "Properties, production, and applications of camelid single-domain antibody fragments," *Appl. Microbiol. Biotechnol.*, 77(1), 13-22 (2007).

Haskard et al., "The production of human monoclonal autoantibodies from patients with rheumatoid arthritis by the ebv-hybridoma technique," *J. Immunol. Methods*, 74, 361-7 (1984).

Holliger et al., "Diabodies: small bivalent and bispecific antibody fragments" *PNAS*, 90, 6444-6448 (1993).

Holt et al., "Domain antibodies: proteins for therapy," *Trends Biotechnol.*, 21(11), 484-90 (2003).

Huse et al., "Generation of a large combinatorial library of the immunoglobulin repertoire in phage lambda," *Science*, 246, 1275-81 (1989).

Hwang et al., "Functional domains of Pseudomonas exotoxin identified by deletion analysis of the gene expressed in *E.coli*," *Cell*, 48(1), 129-36 (1987).

International Preliminary Report on Patentability, International Application No. PCT/US2012/041234 dated Dec. 27, 2013.

International Search Report, International Application No. PCT/US2012/041234 dated Nov. 13, 2012.

International Search Report, International Patent Application No. PCT/US2012/055034, dated Dec. 7, 2012.

Jones et al., "Replacing the complementarity-determining regions in a human antibody with those from a mouse," *Nature*, 321, 522-525 (1986).

Köhler et al., "Derivation of specific antibody-producing tissue culture and tumor lines by cell fusion," *Eur J. Immunol.*, 6(7), 511-9 (1976).

Kondo et al., "Activity of immunotoxins constructed with modified pseudomonas exotoxin a lacking the cell recognition domain," *Biol. Chem.*, 263, 9470-9475 (1988).

Kreitman, R.J., "Immunotoxins for targeted cancer therapy," *AAPS J.*, 8(3), E532-51 (2006).

Lauwereys et al., "Potent enzyme inhibitors derived from dromedary heavy-chain antibodies," *EMBO J.*, 17(13), 3512-20 (1998).

Mufson, R.A., "Tumor antigen targets and tumor immunotherapy," *Front Biosci.*, 11, 337-43 (2006).

Nagata et al., "Removal of B cell epitopes as a practical approach for reducing the immunogenicity of foreign protein-based therapeutics," *Adv. Drug Deliv. Rev.*, 61(11), 977-85 (2009).

Onda et al., "An immunotoxin with greatly reduced immunogenicity by identification and removal of B cell epitopes," *Proc. Natl. Acad. Sci. U.S.A.*, 105(32), 11311-6 (2008).

Onda et al., "Characterization of the B cell epitopes associated with a truncated form of Pseudomonas exotoxin (PE38) used to make immunotoxins for the treatment of cancer patients," *J. Immunol.*, 177, 8822-34 (2006).

Onda et al., "Recombinant immunotoxin against B-cell malignancies with no immunogenicity in mice by removal of B-cell epitopes," *PNAS*, 108(14), 5742-7 (2011).

Oseroff et al., "Molecular determinants of t cell epitope recognition to the common timothy grass allergen," *J. Immunol.*,185(2), 943-55 (2010).

Pai et al., "Anti-tumor activities of immunotoxins made of monoclonal antibody B3 and various forms of pseudomas exotoxin," *PNAS*, 88, 3358-3362 (1991).

Partial International Search Report, International Application No. PCT/US2012/041234 dated Sep. 12, 2012.

Pastan et al., "Immunotoxins containing Pseudomonas exotoxin A: a short history," *Cancer Immunol Immunother*, 52: 338-341 (2003).

Pastan et al., "Immunotoxins with decreased immunogenicity and improved activity," *Leukemia & Lymphoma*, 1-4 (2011).

Pastan et al., "Recombinant immunotoxins in the treatment of cancer," *Methods Mol. Biol.*, 248, 503-18 (2004).

Pastan et al., "Targeted therapy of cancer with recombinant immunotoxins," *Biochem. Biophys. Acta.*, 1333, C1-C6 (1997).

(56) References Cited

OTHER PUBLICATIONS

Pedersen et al., "Comparison of surface accessible residues in human and murine immunoglobulin fv domains," *J. Mol. Biol.*, 235, 959-73 (1994).
Pseudomonas exotoxin A—Pseudomonas aeruginosa PAO1, from http://www.ncbi.nlm.nih.gov/protein/NP_249839.1, pp. 1-3, accessed Oct. 31, 2014.
Reiter et al., "An antibody single-domain phage display library of a native heavy chain variable region: isolation of functional single-domain VH molecules with a unique interface," *J. Mol. Biol.*, 290, 685-698 (1999).
Riechmann et al., "Reshaping human antibodies for therapy," *Nature*, 332, 323-7 (1988).
Roder et al., "The EBV-hybridoma technique," *Methods Enzymol.*, 121, 140-167 (1986).
Roscoe et al., "Identification of epitopes on a mutant form of pseudomonas exotoxin using serum from humans treated with pseudomonas exotoxin containing immunotoxins," *Eur. J. Immunol.*, 27, 1459-68 (1997).
Roscoe et al., "Primate antibody response to immunotoxin: serological and computer-aided analysis of epitopes on a truncated form of pseudomonas exotoxin," *Infect. Immun.*, 62(11), 5055-65 (1994).
Saerens et al., "Single-domain antibodies as building blocks for novel therapeutics," *Curr. Opin. Pharmacol.*, 8(5), 600-8 (2008).
Siegall et al., "Functional analysis of domains II, Ib, and III of Pseudomonas exotoxin," *J. Biol. Chem*, 264(24), 14256-61 (1989).
Uniprot Database EBI Accession No. B7UX39 (Feb. 10, 2009).
Verhoeyen et al., "Reshaping human antibodies: grafting an antilysozyme activity," *Science*, 239, 1534-6 (1988).
Wadhwa et al., "Receptor mediated glycotargeting," *J. Drug Targeting*, 3, 111-27 (1995).
Water, from http://www.biology-online.org/dictionary/Water, pp. 1-3, accessed Apr. 24, 2014.
Weldon et al., "A guide to taming a toxin-recombinant immunotoxins constructed from pseudomonas exotoxin A for the treatment of cancer," *FEBS Journal*, 278, 4683-700 (2011).
Wesolowski et al, "Single domain antibodies: promising experimental and therapeutic tools in infection and immunity," *Med. Microbiol. Immunol.*, 198(3), 157-74 (2009).
Winter et al., "Man-made antibodies," *Nature*, 349, 293-9 (1991).
Written Opinion, International Application No. PCT/US2012/041234 dated Nov. 13, 2012.
Written Opinion, International Patent Application No. PCT/US2012/055034, dated Dec. 7, 2012.

* cited by examiner

| SEQ. ID NO: 188 | 282 | | | | | 290 | | | 300 | | | | 308 | | Intensity of Response (% of response to pool 3) | SEQ ID NO. of shaded area |
|---|---|---|---|---|---|---|---|---|---|---|---|---|---|---|---|---|
| | E | QLE | QCG | YP | VQRL | VAL | YLA | ARL | SWNQV | DQV | | | | | | |
| donors: | | | | | | | | | | | | | | | | |
| D010710aph | E | QLE | QCG | YP | VQRL | VAL | YLA | ARL | SWNQV | DQV | | | | | 80%-100% | 44 |
| | E | QLE | QCG | YP | VQRL | VAL | YLA | ARL | SWNQV | DQV | | | | | 80%-100% | 45 |
| d021610aph | E | QLE | QCG | YP | VQRL | VAL | YLA | ARL | SWNQV | DQV | | | | | 50%-80% | 44 |
| | E | QLE | QCG | YP | VQRL | VAL | YLA | ARL | SWNQV | DQV | | | | | 50%-80% | 45 |
| d031810aph | E | QLE | QCG | YP | VQRL | VAL | YLA | ARL | SWNQV | DQV | | | | | 50%-80% | 43 |
| | E | QLE | QCG | YP | VQRL | VAL | YLA | ARL | SWNQV | DQV | | | | | 80%-100% | 44 |
| | E | QLE | QCG | YP | VQRL | VAL | YLA | ARL | SWNQV | DQV | | | | | 50%-80% | 45 |
| d033010aph | E | QLE | QCG | YP | VQRL | VAL | YLA | ARL | SWNQV | DQV | | | | | 80%-100% | 44 |
| | E | QLE | QCG | YP | VQRL | VAL | YLA | ARL | SWNQV | DQV | | | | | 80%-100% | 45 |
| d040610aph | E | QLE | QCG | YP | VQRL | VAL | YLA | ARL | SWNQV | DQV | | | | | 50%-80% | 44 |
| | E | QLE | QCG | YP | VQRL | VAL | YLA | ARL | SWNQV | DQV | | | | | 80%-100% | 45 |
| d040810aph | E | QLE | QCG | YP | VQRL | VAL | YLA | ARL | SWNQV | DQV | | | | | 80%-100% | 44 |
| | E | QLE | QCG | YP | VQRL | VAL | YLA | ARL | SWNQV | DQV | | | | | 80%-100% | 45 |
| d120109aph (low response level) | E | QLE | QCG | YP | VQRL | VAL | YLA | ARL | SWNQV | DQV | | | | | 50%-80% | 42 |
| | E | QLE | QCG | YP | VQRL | VAL | YLA | ARL | SWNQV | DQV | | | | | 10%-50% | 43 |
| | E | QLE | QCG | YP | VQRL | VAL | YLA | ARL | SWNQV | DQV | | | | | 80%-100% | 44 |
| d122209aph | E | QLE | QCG | YP | VQRL | VAL | YLA | ARL | SWNQV | DQV | | | | | 10%-50% | 44 |
| | E | QLE | QCG | YP | VQRL | VAL | YLA | ARL | SWNQV | DQV | | | | | 80%-100% | 44 |
| | E | QLE | QCG | YP | VQRL | VAL | YLA | ARL | SWNQV | DQV | | | | | 10%-50% | 45 |
| d010510aph (low response level) | E | QLE | QCG | YP | VQRL | VAL | YLA | ARL | SWNQV | DQV | | | | | 80%-100% | 44 |
| d111909aph | E | QLE | QCG | YP | VQRL | VAL | YLA | ARL | SWNQV | DQV | | | | | 50%-80% | 44 |
| | E | QLE | QCG | YP | VQRL | VAL | YLA | ARL | SWNQV | DQV | | | | | 10%-50% | 45 |
| d030410aph | E | QLE | QCG | YP | VQRL | VAL | YLA | ARL | SWNQV | DQV | | | | | 50%-80% | 44 |
| | E | QLE | QCG | YP | VQRL | VAL | YLA | ARL | SWNQV | DQV | | | | | 80%-100% | 44 |
| | E | QLE | QCG | YP | VQRL | VAL | YLA | ARL | SWNQV | DQV | | | | | 50%-80% | 45 |

PSEUDOMONAS EXOTOXIN A WITH LESS IMMUNOGENIC T CELL AND/OR B CELL EPITOPES

CROSS-REFERENCE TO RELATED APPLICATION

This patent application is a divisional of U.S. application Ser. No. 15/095,470, filed Apr. 11, 2016, now U.S. Pat. No. 9,765,123, which is a divisional of U.S. application Ser. No. 14/123,971, now U.S. Pat. No. 9,346,859, which is the U.S. National Phase of International Patent Application No. PCT/US2012/041234, filed Jun. 7, 2012, which claims the benefit of U.S. Provisional Patent Application No. 61/495,085, filed Jun. 9, 2011, and U.S. Provisional Patent Application No. 61/535,668, filed Sep. 16, 2011, each of which is incorporated by reference in its entirety herein.

STATEMENT REGARDING FEDERALLY SPONSORED RESEARCH AND DEVELOPMENT

This invention was made with Government support under project number BC008753 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: one 54,017 Byte ASCII (Text) file named "729021_ST25.TXT," dated Jun. 13, 2017.

BACKGROUND OF THE INVENTION

*Pseudomonas* exotoxin A (PE) is a bacterial toxin with cytotoxic activity that may be effective for destroying or inhibiting the growth of undesirable cells, e.g., cancer cells. Accordingly, PE may be useful for treating or preventing diseases such as, e.g., cancer. However, PE may be highly immunogenic. Accordingly, PE administration may stimulate an anti-PE immune response including, for example, the production of anti-PE antibodies and/or T-cells, that undesirably neutralizes the cytotoxic activity of PE. Such immunogenicity may reduce the amount of PE that can be given to the patient which may, in turn, reduce the effectiveness of the PE for treating the disease, e.g., cancer. Thus, there is a need for improved PE.

BRIEF SUMMARY OF THE INVENTION

An embodiment of the invention provides a *Pseudomonas* exotoxin A (PE) comprising an amino acid sequence having a substitution of one or more of amino acid residues L294, L297, Y298, L299, and R302, with the proviso that when the amino acid sequence comprises a substitution of alanine for the amino acid residue R302, at least one of amino acid residues L294, L297, Y298, and L299 is substituted, wherein the amino acid residues L294, L297, Y298, L299, and R302 are defined by reference to SEQ ID NO: 1, optionally with a substitution of one or more amino acid residues within one or more B-cell epitopes of SEQ ID NO: 1 and/or a substitution of one or more amino acid residues within one or more T cell epitopes within amino acid residues R421, L422, L423, A425, R427, L429, Y439, H440, F443, L444, A446, A447, I450, 463-519, R551, L552, T554, I555, L556, and W558 of SEQ ID NO: 1.

Another embodiment of the invention provides a PE comprising an amino acid sequence comprising Formula I:

$$\text{FCS-R}^1{}_m\text{—R}^2{}_p\text{—R}^3{}_n\text{-PE functional domain III} \qquad \text{(Formula I)}$$

wherein:

m, n, and p are, independently, 0 or 1;

FCS comprises a furin cleavage sequence of amino acid residues, which sequence is cleavable by furin;

$R^1$ comprises 1 or more continuous amino acid residues of residues 285-293 of SEQ ID NO: 1;

$R^2$ comprises $X_1VAX_2X_3X_4AAX_5LSW$ (SEQ ID NO: 2), wherein $X_1$, $X_2$, and $X_4$ are independently leucine, alanine, glycine, serine, or glutamine; $X_3$ is tyrosine, alanine, glycine, serine, or glutamine; and $X_5$ is arginine, alanine, glycine, serine, or glutamine; with the proviso that the PE does not comprise LVALYLAARLSW (SEQ ID NO: 3) and that when $X_5$ is alanine, at least one of $X_1$, $X_2$, $X_3$, and $X_4$ is alanine, glycine, serine, or glutamine;

$R^3$ comprises 1 or more continuous amino acid residues of residues 306-394 of SEQ ID NO: 1; and PE functional domain III comprises residues 395-613 of SEQ ID NO: 1, optionally with a substitution of one or more amino acid residues within one or more B-cell epitopes of SEQ ID NO: 1 and/or a substitution of one or more amino acid residues within one or more T cell epitopes within amino acid residues R421, L422, L423, A425, R427, L429, Y439, H440, F443, L444, A446, A447, I450, 463-519, R551, L552, T554, I555, L556, and W558 of SEQ ID NO: 1.

Still another embodiment of the invention provides a PE comprising an amino acid sequence having a substitution of one or more amino acid residues at positions R421, L422, L423, A425, R427, L429, Y439, H440, F443, L444, A446, A447, I450, 463-519, R551, L552, T554, I555, L556, and W558 of SEQ ID NO: 1; with the proviso that when the amino acid residue at position Q485 or L516 is substituted with alanine, at least one additional amino acid residue at positions R421, L422, L423, A425, R427, L429, Y439, H440, F443, L444, A446, A447, I450, 463-519, R551, L552, T554, I555, L556, and W558 of SEQ ID NO: 1 is substituted, and when the amino acid residue at position R427, R467, R490, R505, R513, or R551 is substituted with alanine, glycine, serine, or glutamine or when the amino acid residue at position R490 is substituted with valine, leucine, or isoleucine, at least one additional amino acid residue at positions R421, L422, L423, A425, R427, L429, Y439, H440, F443, L444, A446, A447, I450, 463-519, R551, L552, T554, I555, L556, and W558 of SEQ ID NO: 1 is substituted which does not include a substitution of alanine, glycine, serine, or glutamine for an amino acid residue at position R427, R467, R490, R505, R513, or R551 or a substitution of valine, leucine, or isoleucine for an amino acid residue at position 490, wherein the amino acid residues R421, L422, L423, A425, R427, L429, Y439, H440, F443, L444, A446, A447, I450, 463-519, R551, L552, T554, I555, L556, and W558 are defined by reference to SEQ ID NO: 1.

Still another embodiment of the invention provides a *Pseudomonas* exotoxin A (PE) comprising a PE amino acid sequence having a substitution of one or more amino acid residues D463, Y481, and L516 as defined by reference to SEQ ID NO: 1, with the proviso that when the amino acid residue at position 516 is substituted with alanine, at least one of amino acid residues D463 and Y481 is also substituted, wherein the PE optionally has a further substitution of one or more amino acid residues within one or more B cell epitopes, and/or a further substitution of one or more amino acid residues within one or more T-cell epitopes, and/or a deletion of one or more continuous amino acid residues of residues 1-273 and 285-394 as defined by SEQ ID NO: 1.

Additional embodiments of the invention provide related chimeric molecules, as well as related nucleic acids, recombinant expression vectors, host cells, populations of cells, and pharmaceutical compositions.

Still another embodiment of the invention provides a method of treating or preventing cancer in a mammal comprising administering to the mammal the inventive PE, chimeric molecule, nucleic acid, recombinant expression vector, host cell, population of cells, or pharmaceutical composition, in an amount effective to treat or prevent cancer in the mammal.

Another embodiment of the invention provides a method of inhibiting the growth of a target cell comprising contacting the cell with the inventive PE, chimeric molecule, nucleic acid, recombinant expression vector, host cell, population of cells, or pharmaceutical composition, in an amount effective to inhibit growth of the target cell.

Additional embodiments of the invention provide methods of producing the inventive PE and methods of producing the inventive chimeric molecule.

BRIEF DESCRIPTION OF THE SEVERAL VIEWS OF THE DRAWING(S)

FIG. 1 is a graph showing the allele frequency (y axis) of various major histocompatibility complex class II DR beta 1 (DRB1) alleles (x axis) in the world population (unshaded bars) and donor cohort (shaded bars).

FIG. 2A is a graph showing the number of spot forming cells (SFC) per $1 \times 10^6$ cells (y axis) indicating a response of naïve donor 031810aph T cells after in vitro expansion and incubation with media (M) (no peptide), peptide pool 3, peptide pool 16, or peptide pool 22 (x axis) as measured by interleukin (IL)-2 ELISpot.

FIG. 2B is a graph showing the number of SFC per $1 \times 10^6$ cells (y axis) indicating a response of naïve donor 031810aph T cells upon incubation with no peptide, peptide pool 3, peptide pool 16, or peptide pool 22 (x axis) without in vitro expansion as measured by IL-2 ELISpot.

FIG. 3 is a graph showing the total number of SFC per $1 \times 10^6$ cells (y axis) by T cells from each of donors 1-50 to no peptide or each of peptide pools 1-22 (x axis) after 14 days of in vitro expansion. The dotted line indicates three times background.

FIG. 4 identifies the specific peptides and regions within the peptides (shaded areas) from peptide pool 3 that stimulate a T cell response at various intensities for various donors.

Figure 7A:
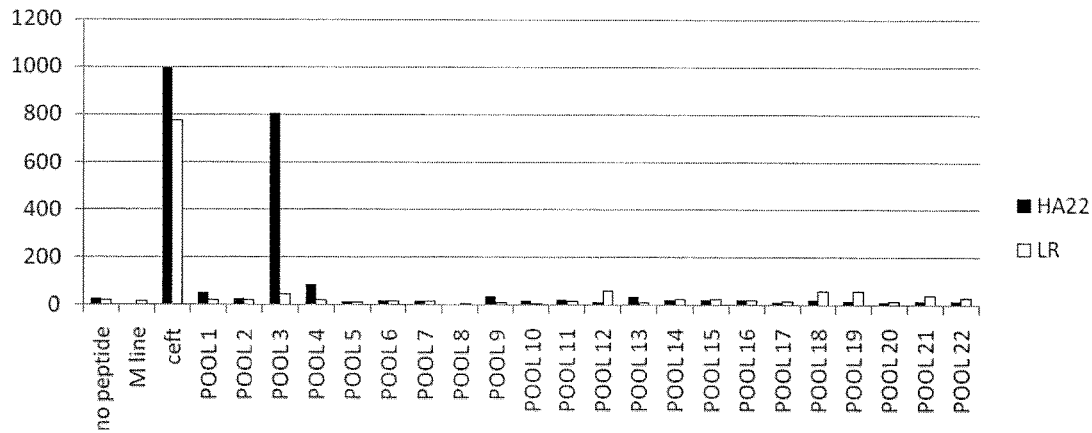

FIG. 7A is a graph showing the T cell response for donor 031510 (SFC per $1 \times 10^6$ cells) (y axis) upon stimulation with HA22 (containing PE38) (shaded bars) or LR RIT (LR) (containing amino acid residues 274-284 and 395-613 of SEQ ID NO: 1) (unshaded bars) and restimulation with one of peptide pools 1-22 (x axis). Controls included ceftazidime (CEFT)-grown cells, cells with no antigen stimulation on day 0 and no antigen stimulation on day 14 ("M line"), and cells with LMB9 stimulation on day 0 and no antigen stimulation on day 14 ("no peptide").

Figure 7B:
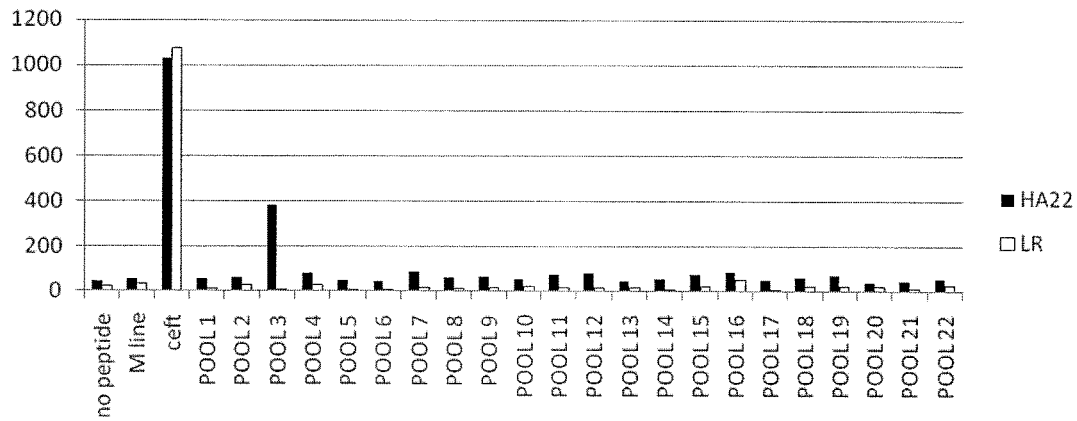

FIG. 7B is a graph showing the T cell response for donor 021610 (SFC per $1 \times 10^6$ cells) (y axis) upon stimulation with HA22 (containing PE38) (shaded bars) or LR RIT (LR) (containing amino acid residues 274-284 and 395-613 of SEQ ID NO: 1) (unshaded bars) and restimulation with no peptide or each of peptide pools 1-22 (x axis). Controls included ceftazidime (CEFT)-grown cells, cells with no antigen stimulation on day 0 and no antigen stimulation on day 14 ("M line"), and cells with LMB9 stimulation on day 0 and no antigen stimulation on day 14 ("no peptide").

Figure 7C:
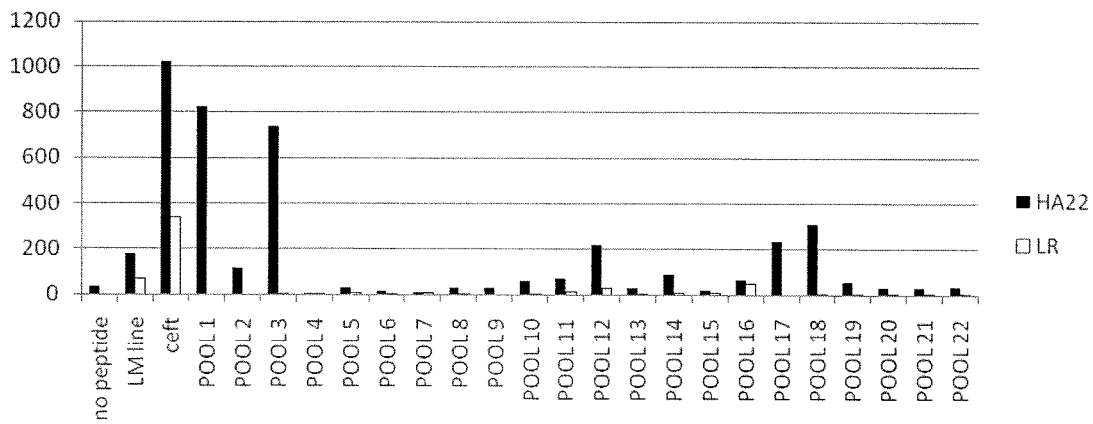

FIG. 7C is a graph showing the T cell response for donor 101509 (SFC per $1 \times 10^6$ cells) (y axis) upon stimulation with HA22 (containing PE38) (shaded bars) or LR RIT (LR) (containing amino acid residues 274-284 and 395-613 of SEQ ID NO: 1) (unshaded bars) and restimulation with no peptide or each of peptide pools 1-22 (x axis). Controls included ceftazidime (CEFT)-grown cells, cells with no antigen stimulation on day 0 and no antigen stimulation on day 14 ("M line"), and cells with LMB9 stimulation on day 0 and no antigen stimulation on day 14 ("no peptide").

Figure 8:
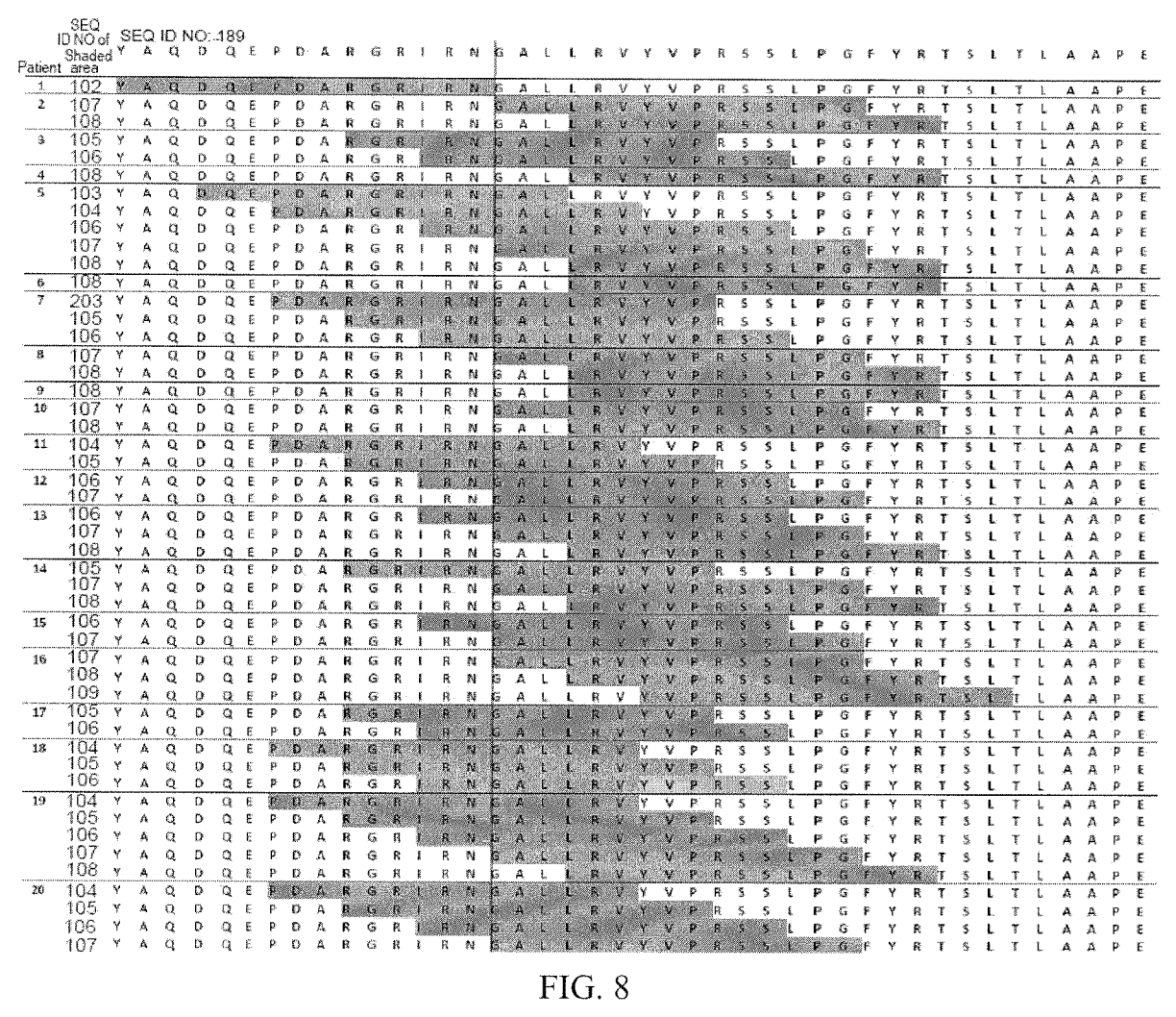

FIG. 8 identifies the specific peptides (shaded areas) of peptides SEQ ID NOs: 102-109 and 203 that stimulate a T cell response as measured by IL-2 production for various donors.

Figure 9:
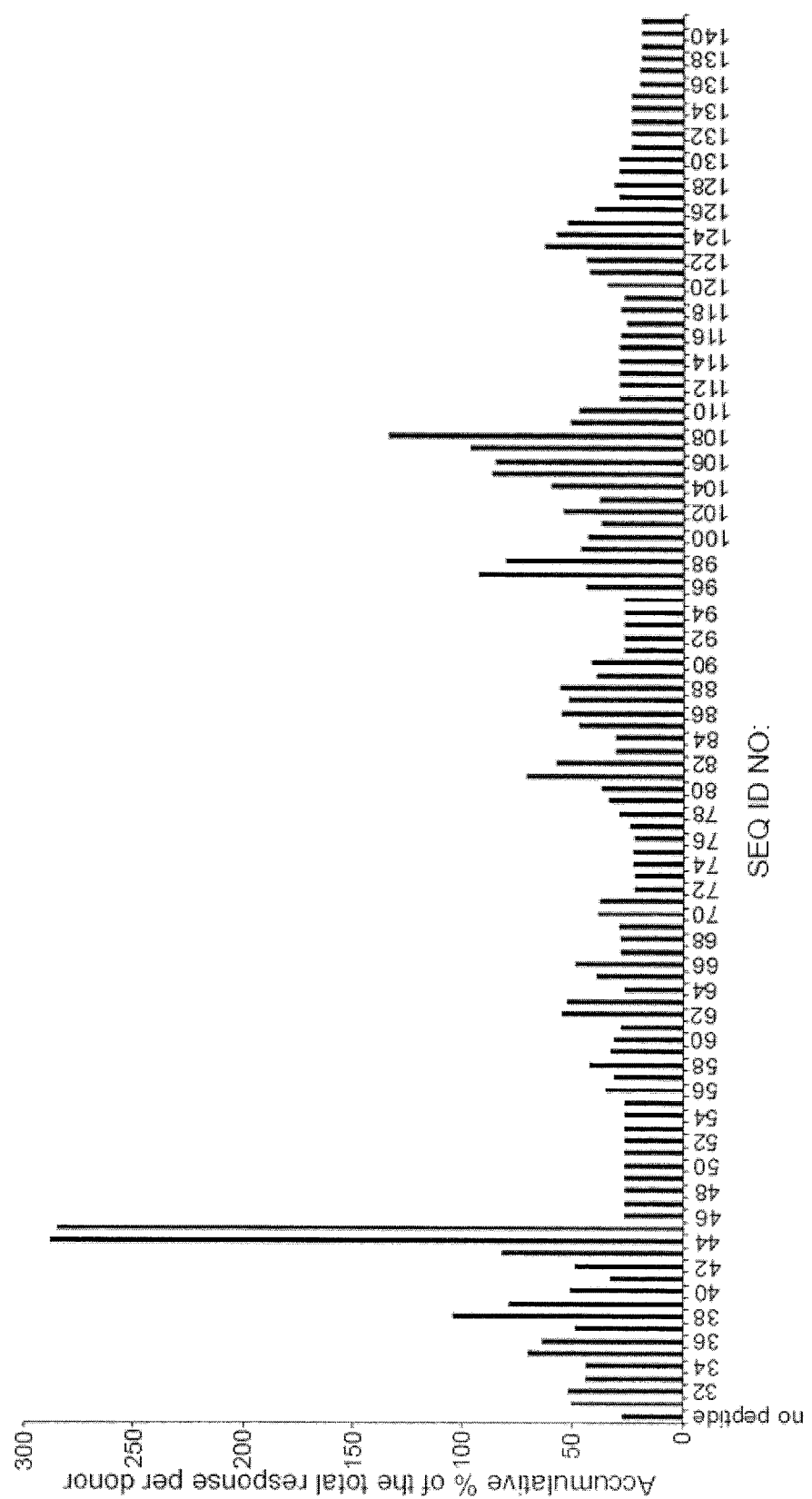

FIG. 9 is a graph showing the accumulative percentage of the total responses per donor for 50 donors for each of SEQ ID NOs: 31-141.

Figure 10:
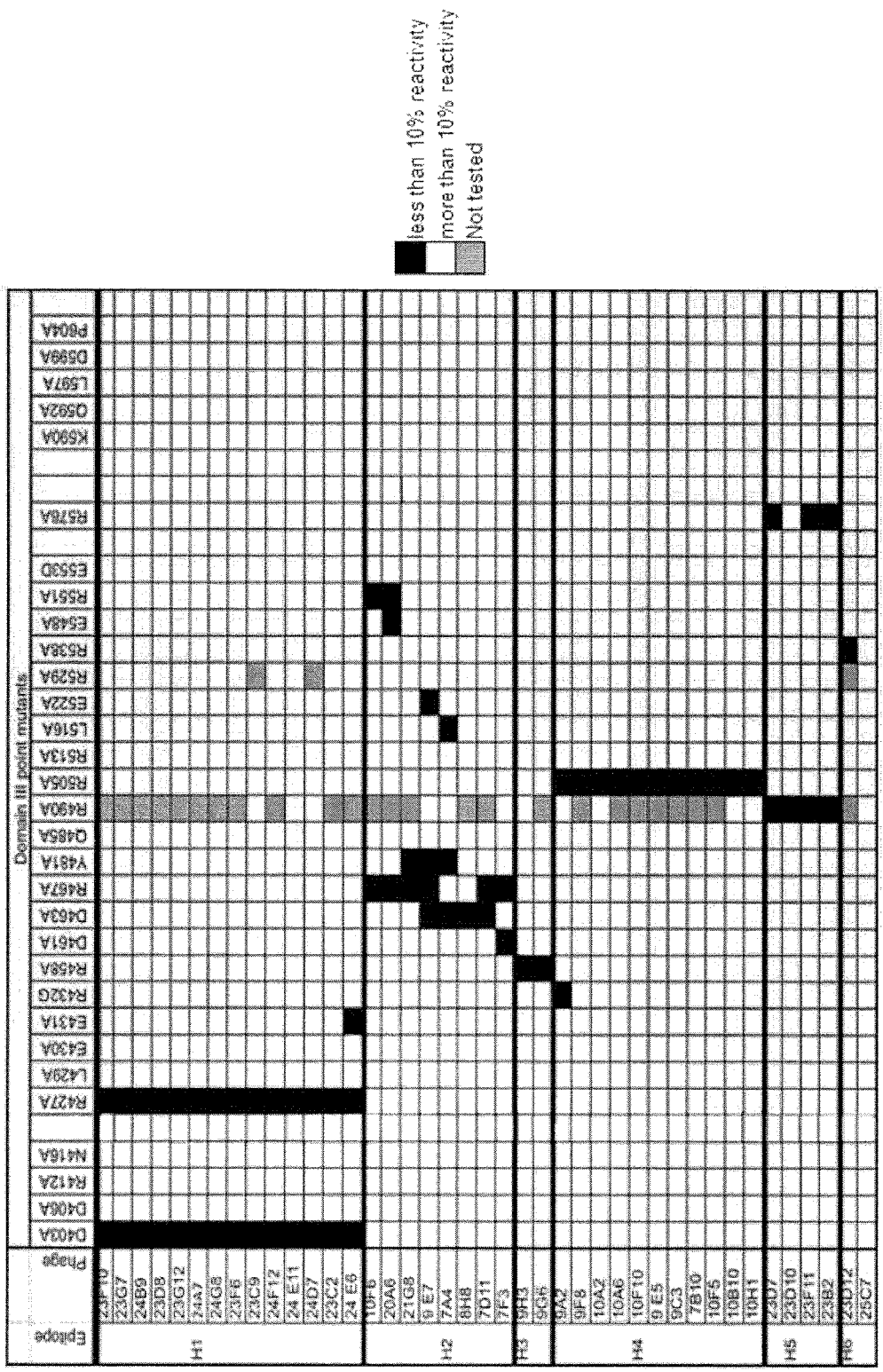

FIG. 10 is a chart showing the reactivity of anti-PE38 (domain III) phage against point-substituted HA22. Black cells represent less than 10% reactivity, blank cells represent more than 10% reactivity, and gray cells indicate not tested. The substitutions are ordered by their location from the N terminus (left) to the C terminus (right).

Figure 11A:
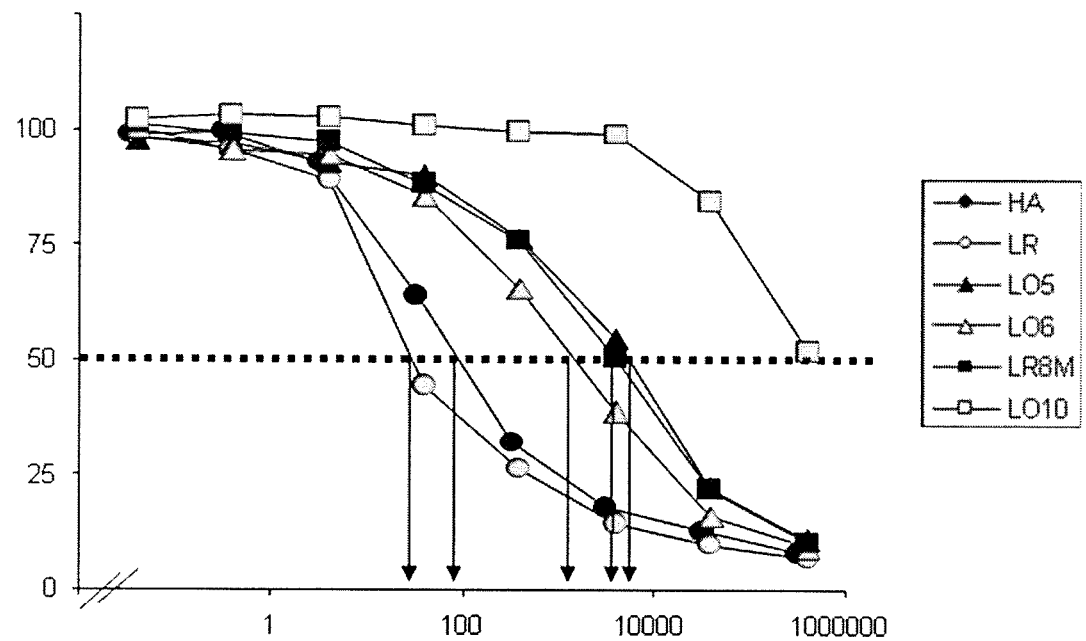
Figure 11B:
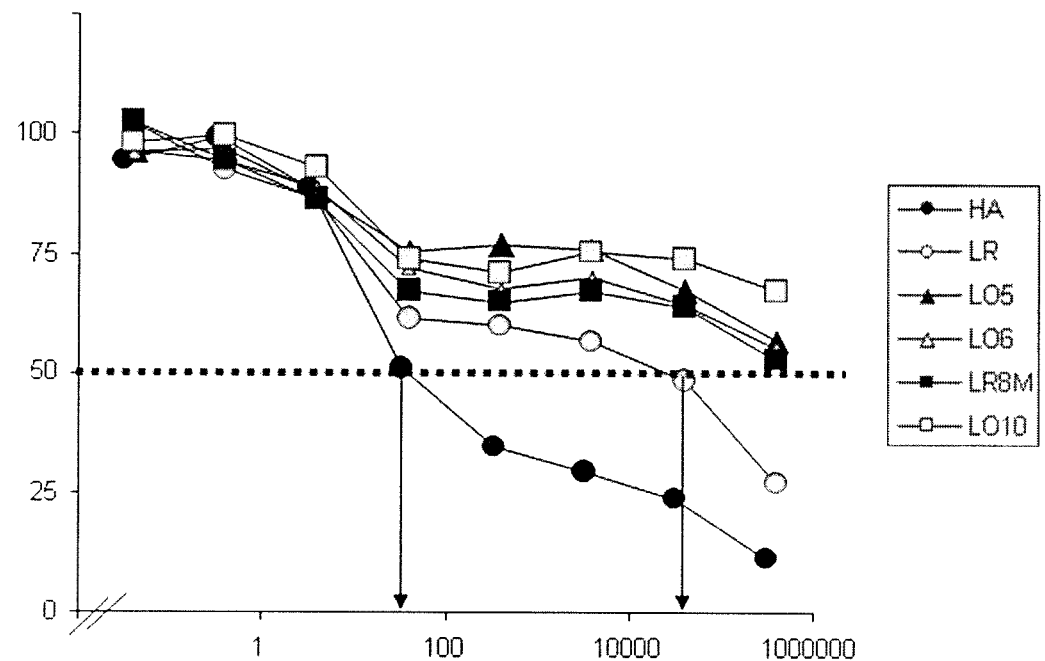

FIGS. 11A and 11B are line graphs showing the results of competition experiments testing the concentration of each of the substituted immunotoxins HA22 ("HA," closed circles), HA22-LR ("LR," open circles), HA22-LO5 ("LO5," closed triangles), HA22-LO6 ("LO6," open triangles), HA22-LR-8M ("LR8M," closed squares), and HA22-LO10 ("LO10," open squares) that reduced the level of antibodies reacting with HA22 by 50% (dotted line) in the serum of a first (FIG. 11A) and second (FIG. 11B) patient undergoing clinical trials with HA22.

Figure 12:
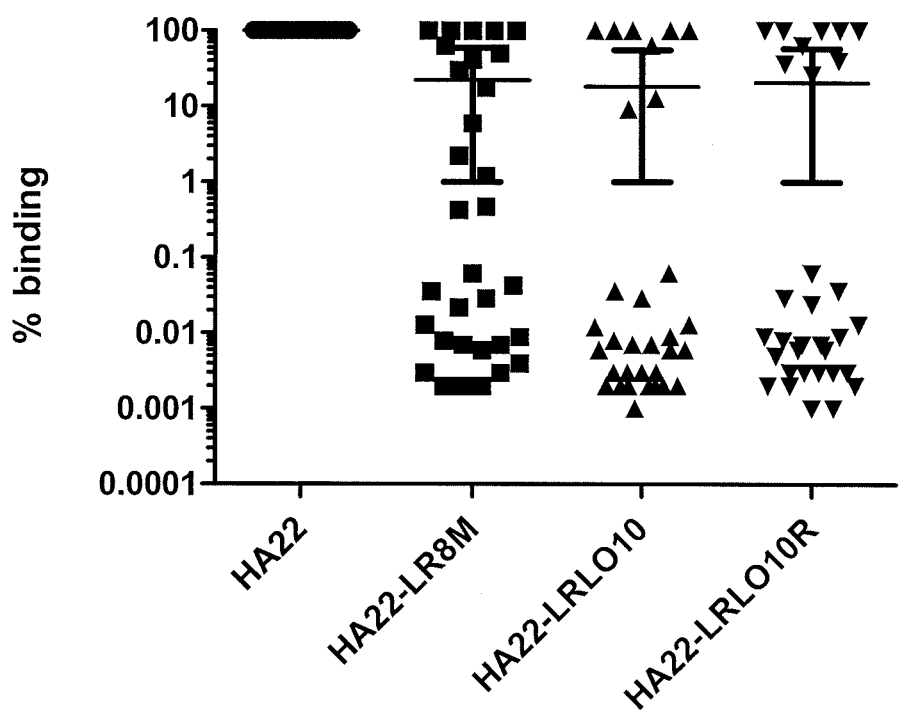

FIG. 12 is a graph showing percent binding of antibodies to HA22, HA22-LR-8M, HA22-LO10 (HA22-LRLO10), or HA22-LRLO10R in the sera of patients treated using PE38.

DETAILED DESCRIPTION OF THE INVENTION

*Pseudomonas* exotoxin A ("PE") is a bacterial toxin (molecular weight 66 kD) secreted by *Pseudomonas aeruginosa*. The native, wild-type PE sequence (SEQ ID NO: 1) is set forth in U.S. Pat. No. 5,602,095, which is incorporated herein by reference. Native, wild-type PE includes three structural domains that contribute to cytotoxicity. Domain Ia (amino acids 1-252) mediates cell binding, domain II (amino acids 253-364) mediates translocation into the cytosol, and domain III (amino acids 400-613) mediates ADP ribosylation of elongation factor 2. While the structural boundary of domain III of PE is considered to start at residue 400, it is contemplated that domain III may require a segment of domain Ib to retain ADP-ribosylating activity. Accordingly, functional domain III is defined as residues 395-613 of PE. The function of domain Ib (amino acids 365-399) remains undefined. Without being bound by a particular theory or mechanism, it is believed that the cytotoxic activity of PE occurs through the inhibition of protein synthesis in eukaryotic cells, e.g., by the inactivation of the ADP-ribosylation of elongation factor 2 (EF-2).

Substitutions of PE are defined herein by reference to the amino acid sequence of PE. Thus, substitutions of PE are described herein by reference to the amino acid residue present at a particular position, followed by the amino acid with which that residue has been replaced in the particular substitution under discussion. In this regard, the positions of the amino acid sequence of a particular embodiment of a PE are referred to herein as the positions of the amino acid sequence of the particular embodiment or as the positions as defined by SEQ ID NO: 1. When the positions are as defined by SEQ ID NO: 1, then the actual positions of the amino acid sequence of a particular embodiment of a PE are defined relative to the corresponding positions of SEQ ID NO: 1 and may represent different residue position numbers than the residue position numbers of SEQ ID NO: 1. Thus, for example, substitutions refer to a replacement of an amino acid residue in the amino acid sequence of a particular embodiment of a PE corresponding to the indicated position of the 613-amino acid sequence of SEQ ID NO: 1 with the understanding that the actual positions in the respective amino acid sequences may be different. For example, when the positions are as defined by SEQ ID NO: 1, the term "R490" refers to the arginine normally present at position 490 of SEQ ID NO: 1, "R490A" indicates that the arginine normally present at position 490 of SEQ ID NO: 1 is replaced by an alanine, while "K590Q" indicates that the lysine normally present at position 590 of SEQ ID NO: 1 has been replaced with a glutamine. In the event of multiple substitutions at two or more positions, the two or more substitutions may be the same or different, i.e., each amino acid residue of the two or more amino acid residues being substituted can be substituted with the same or different amino acid residue unless explicitly indicated otherwise.

The terms "*Pseudomonas* exotoxin" and "PE" as used herein include PE that has been modified from the native protein to reduce or to eliminate immunogenicity. Such modifications may include, but are not limited to, elimination of domain Ia, various amino acid deletions in domains Ib, II, and III, single amino acid substitutions and the addition of one or more sequences at the carboxyl terminus such as DEL and REDL (SEQ ID NO: 7). See Siegall et al., *J. Biol. Chem.*, 264: 14256-14261 (1989). Such modified PEs may be further modified to include any of the inventive substitution(s) for one or more amino acid residues within one or more T-cell and/or B-cell epitopes described herein. In an embodiment, the modified PE may be a cytotoxic fragment of native, wild-type PE. Cytotoxic fragments of PE may include those which are cytotoxic with or without subsequent proteolytic or other processing in the target cell (e.g., as a protein or pre-protein). In a preferred embodiment, the cytotoxic fragment of PE retains at least about 20%, preferably at least about 40%, more preferably about 50%, even more preferably 75%, more preferably at least about 90%, and still more preferably 95% of the cytotoxicity of native PE. In particularly preferred embodiments, the cytotoxic fragment has at least the cytotoxicity of native PE, and preferably has increased cytotoxicity as compared to native PE.

Modified PE that reduces or eliminates immunogenicity includes, for example, PE4E, PE40, PE38, PE25, PE38QQR, PE38KDEL, and PE35. In an embodiment, the PE may be any of PE4E, PE40, PE38, PE25, PE38QQR (in which PE38 has the sequence QQR added at the C-terminus), PE38KDEL (in which PE38 has the sequence KDEL (SEQ ID NO: 5) added at the C-terminus), PE-LR (resistance to lysosomal degradation), and PE35.

In an embodiment, the PE has been modified to reduce immunogenicity by deleting domain Ia as described in U.S. Pat. No. 4,892,827, which is incorporated herein by reference. The PE may also be modified by substituting certain residues of domain Ia. In an embodiment, the PE may be PE4E, which is a substituted PE in which domain Ia is present but in which the basic residues of domain Ia at positions 57, 246, 247, and 249 are replaced with acidic residues (e.g., glutamic acid), as disclosed in U.S. Pat. No. 5,512,658, which is incorporated herein by reference.

PE40 is a truncated derivative of PE (Pai et al., *Proc. Nat'l Acad. Sci. USA*, 88: 3358-62 (1991) and Kondo et al., *Biol. Chem.*, 263: 9470-9475 (1988)). PE35 is a 35 kD carboxyl-terminal fragment of PE in which amino acid residues 1-279 have been deleted and the molecule commences with a Met at position 280 followed by amino acids 281-364 and 381-613 of native PE. PE35 and PE40 are disclosed, for example, in U.S. Pat. Nos. 5,602,095 and 4,892,827, each of which is incorporated herein by reference. PE25 contains the 11-residue fragment from domain II and all of domain III. In some embodiments, the PE contains only domain III.

In a preferred embodiment, the PE is PE38. PE38 contains the translocating and ADP ribosylating domains of PE but not the cell-binding portion (Hwang J. et al., *Cell*, 48: 129-136 (1987)). PE38 is a truncated PE pro-protein composed of amino acids 253-364 and 381-613 (SEQ ID NO: 144) which is activated to its cytotoxic form upon processing within a cell (see e.g., U.S. Pat. No. 5,608,039, which is incorporated herein by reference, and Pastan et al., *Biochim. Biophys. Acta*, 1333: C1-C6 (1997)).

In another preferred embodiment, the PE is PE-LR. PE-LR contains a deletion of domain II except for a furin cleavage sequence (FCS) corresponding to amino acid residues 274-284 of SEQ ID NO: 1 (RHRQPRGWEQL (SEQ ID NO: 8)) and a deletion of amino acid residues 365-394 of domain Ib. Thus, PE-LR contains amino acid residues 274-284 and 395-613 of SEQ ID NO: 1. PE-LR is described in International Patent Application Publication WO 2009/032954, which is incorporated herein by reference. The PE-LR may, optionally, additionally comprise a GGS linking peptide between the FCS and amino acid residues 395-613 of SEQ ID NO: 1.

As noted above, alternatively or additionally, some or all of domain Ib may be deleted with the remaining portions joined by a bridge or directly by a peptide bond. Alternatively or additionally, some of the amino portion of domain II may be deleted. Alternatively or additionally, the C-terminal end may contain the native sequence of residues 609-613 (REDLK) (SEQ ID NO: 6), or may contain a variation that may maintain the ability of the PE to translocate into the cytosol, such as KDEL (SEQ ID NO: 5) or REDL (SEQ ID NO: 7), and repeats of these sequences. See, e.g., U.S. Pat. Nos. 5,854,044; 5,821,238; and 5,602,095 and International Patent Application Publication WO 1999/051643, which are incorporated herein by reference. Any form of PE in which immunogenicity has been eliminated or reduced can be used in combination with any of the inventive substitution(s) for one or more amino acid residues within one or more T-cell and/or B-cell epitopes described herein so long as it remains capable of cytotoxicity to targeted cells, e.g., by translocation and EF-2 ribosylation in a targeted cell.

An embodiment of the invention provides a Pseudomonas exotoxin A (PE), including any PE modified from the native protein as described herein, comprising an amino acid sequence having a substitution of one or more of amino acid residues L294, L297, Y298, L299, and R302, with the proviso that when the amino acid sequence comprises a substitution of alanine for the amino acid residue R302, at least one additional amino acid residue is substituted, wherein the amino acid residues L294, L297, Y298, L299, and R302 are defined by reference to SEQ ID NO: 1, optionally with a substitution of one or more amino acid residues within one or more B-cell epitopes of SEQ ID NO: 1 and/or a substitution of one or more amino acid residues within one or more T cell epitopes within amino acid residues R421, L422, L423, A425, R427, L429, Y439, H440, F443, L444, A446, A447, I450, 463-519, R551, L552, T554, I555, L556, and W558 of SEQ ID NO: 1. Preferably, the substitution of one or more amino acid residues within one or more T cell epitopes is a substitution of one or more amino acid residues at positions R421, L422, L423, A425, R427, L429, Y439, H440, F443, L444, A446, A447, I450, Y470, I471, A472, P475, A476, L477, I493, R494, N495, L498, L499, R500, V501, Y502, V503, R505, L508, P509, R551, L552, T554, I555, L556, and W558.

Another embodiment of the invention provides a Pseudomonas exotoxin A (PE), including any PE modified from the native protein as described herein, comprising an amino acid sequence having a substitution of one or more of amino acid residues L294, L297, Y298, L299, and R302, with the proviso that when the amino acid sequence comprises a substitution of alanine for the amino acid residue R302, at least one of amino acid residues L294, L297, Y298, and L299 is substituted, wherein the amino acid residues L294, L297, Y298, L299, and R302 are defined by reference to SEQ ID NO: 1, optionally with a substitution of one or more amino acid residues within one or more B-cell epitopes of SEQ ID NO: 1 and/or a substitution of one or more amino acid residues within one or more T cell epitopes within amino acid residues R421, L422, L423, A425, R427, L429, Y439, H440, F443, L444, A446, A447, I450, 463-519, R551, L552, T554, I555, L556, and W558 of SEQ ID NO: 1. It has been discovered that amino acid residues L294, L297, Y298, L299, and R302 are located within one or more T-cell epitopes of PE. Thus, a substitution of one or more of amino acid residues L294, L297, Y298, L299, and R302 may, advantageously, remove one or more T cell epitope(s). Accordingly, the inventive PEs may, advantageously, be less immunogenic than an unsubstituted (e.g., wild-type) PE.

The substitution of one or more of amino acid residues L294, L297, Y298, L299, and R302 may be a substitution of any amino acid residue for one or more of amino acid residues L294, L297, Y298, L299, and R302. In an embodiment of the invention, the substitution of one or more of amino acid residues L294, L297, Y298, L299, and R302 is a substitution of alanine, glycine, serine, or glutamine in place of one or more of amino acid residues L294, L297, Y298, L299, and R302.

In an embodiment of the invention, the PE comprises $X_1VAX_2X_3X_4AAX_5LSW$ (SEQ ID NO: 2), wherein $X_1$, $X_2$, and $X_4$ are independently leucine, alanine, glycine, serine, or glutamine; $X_3$ is tyrosine, alanine, glycine, serine, or glutamine; and $X_5$ is arginine, alanine, glycine, serine, or glutamine; with the proviso that the PE does not comprise LVALYLAARLSW (SEQ ID NO: 3) and that when $X_5$ is alanine, at least one of $X_1$, $X_2$, $X_3$, and $X_4$ is alanine, glycine, serine, or glutamine.

Another embodiment of the invention provides a Pseudomonas exotoxin A (PE) comprising a PE amino acid sequence having a substitution of one or more of amino acid residues D463, Y481, and L516 as defined by reference to SEQ ID NO: 1, with the proviso that when the amino acid residue at position 516 is substituted with alanine, at least one of amino acid residues D463 and Y481 is substituted, wherein the PE optionally has a further substitution of one or more amino acid residues within one or more B cell epitopes and/or a further substitution of one or more amino acid residues within one or more T-cell epitopes, and/or a deletion of one or more continuous amino acid residues of residues 1-273 and 285-394 as defined by SEQ ID NO: 1. Preferably, the substitution of one or more of amino acid residues D463, Y481, and L516 is a substitution of, independently, alanine, glycine, serine, or glutamine in place of one or more of amino acid residues D463, Y481, and L516. It has been discovered that amino acid residues D463, Y481, and L516 are located within one or more B-cell epitopes of PE. Thus, a substitution of one or more of amino acid residues D463, Y481, and L516 may, advantageously, remove one or more T-cell and/or B-cell epitope(s). Accordingly, the inventive PEs may, advantageously, be less immunogenic than an unsubstituted (e.g., wild-type) PE.

In an embodiment of the invention, the further substitution of an amino acid within one or more B-cell epitopes is a substitution of one or more of amino acid residues E282, E285, P290, R313, N314, P319, D324, E327, E331, Q332, D403, D406, R412, R427, E431, R432, R458, D461, R467, R490, R505, R513, E522, R538, E548, R551, R576, Q592, and L597, as defined by reference to SEQ ID NO: 1. Preferably, the further substitution of an amino acid within one or more B-cell epitopes is a substitution of, independently, alanine, glycine, or serine in place of one or more amino acid residues R427, R458, R467, R490, R505, and R538. In an especially preferred embodiment, the substitution of one or more of amino acid residues D463, Y481, and L516 is a substitution of alanine in place of amino acid residue D463 and the further substitution of an amino acid within one or more B-cell epitopes is: (a) a substitution of alanine for amino acid residue R427; (b) a substitution of alanine for amino acid residue R458; (c) a substitution of alanine for amino acid residue R467; (d) a substitution of alanine for amino acid residue R490; (e) a substitution of alanine for amino acid residue R505; and (f) a substitution of alanine for amino acid residue R538, as defined by reference to SEQ ID NO: 1.

In addition to the substitution(s) for one or more amino acid residues within one or more PE T-cell and/or B-cell epitopes described herein, the inventive PE may, optionally, also include additional substitution(s) for one or more amino acid residues within one or more B-cell epitopes of SEQ ID NO: 1. In this regard, in an embodiment of the invention, the PE has a substitution of one or more amino acids within one or more B-cell epitopes of SEQ ID NO: 1. In a preferred embodiment of the invention, the substitution of one or more amino acid within one or more B-cell epitopes of SEQ ID NO: 1 includes a substitution of alanine, glycine, serine, or glutamine for one or more amino acids within one or more B-cell epitopes of SEQ ID NO: 1. The substitution(s) within one or more B-cell epitopes may, advantageously, further reduce immunogenicity by the removal of one or more B-cell epitopes. The substitution(s) may be located within any suitable PE B-cell epitope. Exemplary B-cell epitopes are disclosed in, for example, International Patent Application Publications WO 2007/016150, WO 2009/032954, and WO 2011/032022, each of which is incorporated herein by reference. In a preferred embodiment, the substitution of one or more amino acids within one or more B-cell epitopes of SEQ ID NO: 1 is a substitution of alanine, glycine, serine, or glutamine, independently, in place of one or more of amino acid residues E282, E285, P290, R313, N314, P319, D324, E327, E331, Q332, D403, D406, R412, R427, E431, R432, R458, D461, D463, R467, Y481, R490, R505, R513, L516, E522, R538, E548, R551, R576, K590, Q592, and L597, wherein the amino acid residues E282, E285, P290, R313, N314, P319, D324, E327, E331, Q332, D403, D406, R412, R427, E431, R432, R458, D461, D463, R467, Y481, R490, R505, R513, L516, E522, R538, E548, R551, R576, K590, Q592, and L597 are defined by reference to SEQ ID NO: 1. In a particularly preferred embodiment, the substitution of an amino acid within one or more B-cell epitopes of SEQ ID NO: 1 is a substitution of alanine, glycine, or serine in place of one or more amino acid residues D406, R432, R467, R490, R513, E548, K590, and Q592. In an especially preferred embodiment, the substitution of an amino acid within one or more B-cell epitopes of SEQ ID NO: 1 is: (a) a substitution of alanine for amino acid residue D406; (b) a substitution of glycine for amino acid residue R432; (c) a substitution of alanine for amino acid residue R467; (d) a substitution of alanine for amino acid residue R490; (e) a substitution of alanine for amino acid residue R513; (f) a substitution of serine for amino acid residue E548; (g) a substitution of serine for amino acid residue K590; and (h) a substitution of alanine for amino acid residue Q592.

In an embodiment of the invention, the PE comprises an amino acid sequence having a substitution of one or more amino acid residues at positions R421, L422, L423, A425, R427, L429, Y439, H440, F443, L444, A446, A447, I450, 463-519, R551, L552, T554, 555, L556, and W558 of SEQ ID NO: 1 alone or in combination with any of the other substitutions described herein. In an embodiment of the invention, the substitution of one or more amino acid residues at positions R421, L422, L423, A425, R427, L429, Y439, H440, F443, L444, A446, A447, I450, 463-519, R551, L552, T554, I555, L556, and W558 of SEQ ID NO: 1 is a substitution of one or more amino acid residues at positions R421, L422, L423, A425, R427, L429, Y439, H440, F443, L444, A446, A447, I450, Y470, I471, A472, P475, A476, L477, I493, R494, N495, L498, L499, R500, V501, Y502, V503, R505, L508, P509, R551, L552, T554, I555, L556, and W558.

The substitution of one or more amino acid residues at positions R421, L422, L423, A425, R427, L429, Y439, H440, F443, L444, A446, A447, I450, 463-519, R551, L552, T554, I555, L556, and W558 of SEQ ID NO: 1 may be a substitution of any amino acid residue in place of an amino acid residue at any one or more of positions R421, L422, L423, A425, R427, L429, Y439, H440, F443, L444, A446, A447, I450, 463-519, R551, L552, T554, I555, L556, and W558 of SEQ ID NO:1. The substitution of one or more amino acid residues at positions R421, L422, L423, A425, R427, L429, Y439, H440, F443, L444, A446, A447, I450, 463-519, R551, L552, T554, I555, L556, and W558 of SEQ ID NO: 1 may include, e.g., a substitution of alanine, glycine, serine, or glutamine in place of one or more amino acid residues at position 421, 422, 423, 425, 427, 429, 439, 440, 443, 444, 446, 447, 450, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 551, 552, 554, 555, 556, and 558 of SEQ ID NO: 1. In a preferred embodiment, the substitution of one or more amino acid residues at positions R421, L422, L423, A425, R427, L429, Y439, H440, F443, L444, A446, A447, I450, 463-519, R551, L552, T554, I555, L556, and W558 of SEQ ID NO: 1 is a substitution of alanine, glycine, serine, or glutamine in place of one or more of amino acid residues R421, L422, L423, A425, R427, L429, Y439, H440, F443, L444, A446, A447, I450, Y470, I471, A472, P475, A476, L477, I493, R494, N495, L498, L499, R500, V501, Y502, V503, R505, L508, P509, R551, L552, T554, I555, L556, and W558. One or more substitutions in one or more T cell epitopes located at positions R421, L422, L423, A425, R427, L429, Y439, H440, F443, L444, A446, A447, I450, 463-519, R551, L552, T554, I555, L556, and W558 of PE as defined by reference to SEQ ID NO: 1 may further reduce immunogenicity of PE. In an embodiment, the amino acid sequence does not have a substitution of one or more amino acid residues at positions 427, 467, 485, 490, 505, 513, 516, and 551.

In another embodiment of the invention, the PE comprises an amino acid sequence having a substitution of one or more amino acid residues at positions R421, L422, L423, A425, R427, L429, Y439, H440, F443, L444, A446, A447, I450, 463-519, R551, L552, T554, I555, L556, and W558 of SEQ ID NO: 1; with the proviso that when the amino acid residue at position Q485 or L516 is substituted with alanine, at least one additional amino acid residue is substituted, and when the amino acid residue at position R427, R467, R490, R505, R513, or R551 is substituted with alanine, glycine, serine, or glutamine or when the amino acid residue at position R490 is substituted with valine, leucine, or isoleucine, at least one additional amino acid residue is substituted which does not include a substitution of alanine, glycine, seine, or glutamine for an amino acid residue at position 282, 285, 290, 313, 314, 319, 324, 327, 331, 332, 403, 406, 412, 427, 431, 432, 458, 461, 467, 490, 505, 513, 522, 538, 548, 551, 576, 590, 592, or 597 or a substitution of valine, leucine, or isoleucine for an amino acid residue at position 490, wherein the amino acid residues 282, 285, 290, 302, 313, 314, 319, 324, 327, 331, 332, 403, 406, 412, 427, 431, 432, 458, 461, 463-519, 522, 538, 548, 551, 576, 590, 592, and 597 are defined by reference to SEQ ID NO: 1.

In yet another embodiment of the invention, the PE comprises an amino acid sequence having a substitution of one or more amino acid residues at positions R421, L422, L423, A425, R427, L429, Y439, H440, F443, L444, A446, A447, I450, 463-519, R551, L552, T554, I555, L556, and W558 of SEQ ID NO: 1; with the proviso that when the amino acid residue at position Q485 or L516 is substituted with alanine, at least one additional amino acid residue at positions R421, L422, L423, A425, R427, L429, Y439, H440, F443, L444, A446, A447, I450, 463-519, R551, L552, T554, I555, L556, and W558 of SEQ ID NO: 1 is substituted, and when the amino acid residue at position R427, R467, R490, R505, R513, or R551 is substituted with alanine, glycine, serine, or glutamine or when the amino acid residue at position R490 is substituted with valine, leucine, or isoleucine, at least one additional amino acid residue at positions R421, L422, L423, A425, R427, L429, Y439, H440, F443, L444, A446, A447, I450, 463-519, R551, L552, T554, I555, L556, and W558 of SEQ ID NO: 1 is substituted which does not include a substitution of alanine, glycine, serine, or glutamine for an amino acid residue at position R427, R467, R490, R505, R513, R551 or a substitution of valine, leucine, or isoleucine for an amino acid residue at position R490, wherein the amino acid residues R421, L422, L423, A425, R427, L429, Y439, H440, F443, L444, A446, A447, I450, 463-519, R551, L552, T554, I555, L556, and W558 are defined by reference to SEQ ID NO: 1.

Preferably, the PE comprises one or more substitutions that increase cytotoxicity as disclosed, for example, in International Patent Application Publication WO 2007/016150, which is incorporated herein by reference. In this regard, an embodiment of the invention provides PE with a substitution of an amino acid within one or more B-cell epitopes of SEQ ID NO: 1 and the substitution of an amino acid within one or more B-cell epitopes of SEQ ID NO: 1 is a substitution of valine, leucine, or isoleucine in place of amino acid residue R490, wherein the amino acid residue R490 is defined by reference to SEQ ID NO: 1. In an embodiment of the invention, substitution of one or more amino acid residues at positions 313, 327, 331, 332, 431, 432, 505, 516, 538, and 590 defined by reference to SEQ ID NO: 1 with alanine or glutamine may provide a PE with an increased cytotoxicity as disclosed, for example, in International Patent Application Publication WO 2007/016150, which is incorporated herein by reference. Increased cytotoxic activity and decreased immunogenicity can occur simultaneously, and are not mutually exclusive. Substitutions that both increase cytotoxic activity and decrease immunogenicity, such as substitutions of R490 to glycine or, more preferably, alanine, are especially preferred.

In an embodiment of the invention, the PE comprises an amino acid sequence comprising Formula I:

FCS-R$^1_m$R$^2_p$—R$^3_n$-PE functional domain III  (Formula I)

wherein:
m, n, and p are, independently, 0 or 1;
FCS comprises a furin cleavage sequence of amino acid residues, which sequence is cleavable by furin;
R$^1$ comprises 1 or more continuous amino acid residues of residues 285-293 of SEQ ID NO: 1;
R$^2$ comprises X$_1$VAX$_2$X$_3$X$_4$AAX$_5$LSW (SEQ ID NO: 2), wherein X$_1$, X$_2$, and X$_4$ are independently leucine, alanine, glycine, serine, or glutamine; X$_3$ is tyrosine, alanine, glycine, serine, or glutamine; and X$_5$ is arginine, alanine, glycine, serine, or glutamine; with the proviso that the PE does not comprise LVALYLAARLSW (SEQ ID NO: 3) and that when X$_5$ is alanine, at least one of X$_1$, X$_2$, X$_3$, and X$_4$ is alanine, glycine, serine, or glutamine;
R$^3$ comprises 1 or more continuous amino acid residues of residues 306-394 of SEQ ID NO: 1; and
PE functional domain III comprises residues 395-613 of SEQ ID NO: 1 optionally with a substitution of one or more amino acid residues within one or more B-cell epitopes of SEQ ID NO: 1 and/or a substitution of one or more amino acid residues within one or more T cell epitopes within amino acid residues R421, L422, L423, A425, R427, L429, Y439, H440, F443, L444, A446, A447, I450, 463-519, R551, L552, T554, I555, L556, and W558 of SEQ ID NO: 1. In an embodiment, the substitution of one or more amino acid residues R421, L422, L423, A425, R427, L429, Y439, H440, F443, L444, A446, A447, I450, 463-519, R551, L552, T554, I555, L556, and W558 of SEQ ID NO: 1 is a substitution of one or more amino acid residues R421, L422, L423, A425, R427, L429, Y439, H440, F443, L444, A446, A447, I450, Y470, I471, A472, P475, A476, L477, I493, R494, N495, L498, L499, R500, V501, Y502, V503, R505, L508, P509, R551, L552, T554, I555, L556, and W558.

In an embodiment of the invention, m, n, and/or p of Formula I are 0. In an embodiment of the invention, when m, n, and p are each 0, the PE of Formula I may further comprise a GGS linking peptide between FCS and PE functional domain III.

Without being bound by a particular theory or mechanism, it is believed that PEs containing the furin cleavage sequence (FCS) undergo proteolytic processing inside target cells, thereby activating the cytotoxic activity of the toxin. The FCS of the inventive PEs may comprise any suitable furin cleavage sequence of amino acid residues, which sequence is cleavable by furin. Exemplary furin cleavage sequences are described in Duckert et al., *Protein Engineering, Design & Selection,* 17 (1): 107-112 (2004) and International Patent Application Publication WO 2009/032954, each of which is incorporated herein by reference. In an embodiment of the invention, FCS comprises residues 274-284 of SEQ ID NO: 1 (i.e., RHRQPRGWEQL (SEQ ID NO: 8)), wherein the substitution of an amino acid within one or more B-cell epitopes of SEQ ID NO: 1 is a substitution of alanine, glycine, serine, or glutamine for amino acid residue E282 of SEQ ID NO: 1. Other suitable FCS amino acid sequences include, but are not limited to: R—X$_1$—X$_2$—R, wherein X$_1$ is any naturally occurring amino acid and X$_2$ is any naturally occurring amino acid (SEQ ID NO: 9), RKKR (SEQ ID NO: 10), RRRR (SEQ ID NO: 11), RKAR (SEQ ID NO: 12), SRVARS (SEQ ID NO: 13), TSSRKRRFW (SEQ ID NO: 14), ASRRKARSW (SEQ ID NO: 15), RRVKKRFW (SEQ ID NO: 16), RNVVRRDW (SEQ ID NO: 17), TRAVRRRSW (SEQ ID NO: 18), RQPR (SEQ ID NO: 19), RHRQPRGW (SEQ ID NO: 20), RHRQPRGWE (SEQ ID NO: 21), HRQPRGWEQ (SEQ ID NO: 22), RQPRGWE (SEQ ID NO: 23), RHRSKRGWEQL (SEQ ID NO: 24), RSKR (SEQ ID NO: 25), RHRSKRGW (SEQ ID NO: 26), HRSKRGWE (SEQ ID NO: 27), RSKRGWEQL (SEQ ID NO: 28), HRSKRGWEQL (SEQ ID NO: 29), RHRSKR (SEQ ID NO: 30), and R—X$_1$—X$_2$—R, wherein X$_1$ is any naturally occurring amino acid and X$_2$ is arginine or lysine (SEQ ID NO: 4).

In an embodiment of the invention, m of Formula I is 1 and R$^1$ of Formula I comprises residues 285-293 of SEQ ID NO: 1, wherein the substitution of an amino acid within one or more B-cell epitopes of SEQ ID NO: 1 includes a substitution of alanine, glycine, serine, or glutamine for amino acid residue E285 and/or P290 of SEQ ID NO: 1.

In another embodiment of the invention, n of Formula I is 1 and R$^3$ of Formula I comprises residues 306-394 of SEQ ID NO: 1, wherein the substitution of an amino acid within one or more B-cell epitopes of SEQ ID NO: 1 includes a substitution of alanine, glycine, serine, or glutamine for one or more of amino acid residues R313, N314, P319, D324, E327, E331, and Q332 of SEQ ID NO: 1.

In still another embodiment of the invention, PE functional domain III comprises residues 395-613 of SEQ ID NO: 1, wherein the substitution of an amino acid within one or more B-cell epitopes of SEQ ID NO: 1 includes a substitution of alanine, glycine, serine, or glutamine for one or more of amino acid residues D403, D406, R412, R427, E431, R432, R458, D461, D463, R467, Y481, R490, R505, R513, R516, E522, R538, E548, R551, R576, K590, Q592, and L597 of SEQ ID NO: 1. In a preferred embodiment of the invention, PE functional domain III comprises SEQ ID NO: 142. In an especially preferred embodiment of the invention, PE functional domain III comprises SEQ ID NO: 143.

The inventive PE may be less immunogenic than an unsubstituted PE in accordance with the invention if the immune response to the inventive PE is diminished, quantitatively or qualitatively, as compared to the immune response to an unsubstituted PE. A quantitative decrease in immunogenicity encompasses a decrease in the magnitude or degree of the immune response. The magnitude or degree of immunogenicity can be measured on the basis of any number of known parameters, such as a decrease in the level of cytokine (e.g., antigen-specific cytokine) production (cytokine concentration), a decrease in the number of lymphocytes activated (e.g., proliferation of lymphocytes (e.g., antigen-specific lymphocytes)) or recruited, and/or a decrease in the production of antibodies (antigen-specific antibodies), etc. A qualitative decrease in immunogenicity encompasses any change in the nature of the immune response that renders the immune response less effective at mediating the reduction of the cytotoxic activity of the PE. Methods of measuring immunogenicity are known in the art. For example, measuring the types and levels of cytokines produced can measure immunogenicity. Alternatively or additionally, measuring the binding of PE to antibodies (e.g., antibodies previously exposed to PE) and/or measuring the ability of the PE to induce antibodies when administered to a mammal (e.g., humans, mice, and/or mice in which the mouse immune system is replaced with a human immune system) can measure immunogenicity. A less immunogenic PE may be characterized by a decrease in the production of cytokines such as any one or more of IFN-γ, TNF-α, and granzyme B, and/or a reduced stimulation of a cell-mediated immune response, such as a decrease in the proliferation and activation of T-cells and/or macrophages specific for PE as compared to that obtained with an unsubstituted PE. Alternatively or additionally, less immunogenic PE may be characterized by an increase in the production of TGF-beta and/or IL-10 as compared to that obtained with an unsubstituted PE. In a preferred embodiment, reduced immunogenicity is characterized by any one or more of a decrease in T cell stimulation, a decrease in T cell proliferation, and a decrease in T cell IFNγ and/or granzyme B secretion. Alternatively or additionally, a less immunogenic PE may be characterized by a decrease in the stimulation and/or activation of B-cells specific for PE as compared to that obtained with an unsubstituted PE. For example, less immunogenic PE may be characterized by a decrease in the differentiation of B cells into antibody-secreting plasma cells and/or memory cells as compared to that obtained with an unsubstituted PE. Reduced immunogenicity may be characterized by any one or more of a decrease in B cell stimulation, a decrease in B cell proliferation, and a decrease in anti-PE antibody secretion. Qualitative and quantitative diminishment of immunogenicity can occur simultaneously and are not mutually exclusive.

One of ordinary skill in the art will readily appreciate that the inventive PEs can be modified in any number of ways, such that the therapeutic or prophylactic efficacy of the inventive PEs is increased through the modification. For instance, the inventive PEs can be conjugated or fused either directly or indirectly through a linker to a targeting moiety. In this regard, an embodiment of the invention provides a chimeric molecule comprising (a) a targeting moiety conjugated or fused to (b) any of the inventive PEs described herein. The practice of conjugating compounds, e.g., inventive PEs, to targeting moieties is known in the art. See, for instance, Wadwa et al., *J. Drug Targeting*, 3: 111 (1995), and U.S. Pat. No. 5,087,616.

The term "targeting moiety" as used herein, refers to any molecule or agent that specifically recognizes and binds to a cell-surface marker, such that the targeting moiety directs the delivery of the inventive PE to a population of cells on which surface the receptor is expressed. Targeting moieties include, but are not limited to, antibodies (e.g., monoclonal antibodies), or fragments thereof, peptides, hormones, growth factors, cytokines, and any other natural or non-natural ligands.

The term "antibody," as used herein, refers to whole (also known as "intact") antibodies or antigen binding portions thereof that retain antigen recognition and binding capability. The antibody or antigen binding portions thereof can be a naturally-occurring antibody or antigen binding portion thereof, e.g., an antibody or antigen binding portion thereof isolated and/or purified from a mammal, e.g., mouse, rabbit, goat, horse, chicken, hamster, human, etc. The antibody or antigen binding portion thereof can be in monomeric or polymeric form. Also, the antibody or antigen binding portion thereof can have any level of affinity or avidity for the cell surface marker. Desirably, the antibody or antigen binding portion thereof is specific for the cell surface marker, such that there is minimal cross-reaction with other peptides or proteins.

The antibody may be monoclonal or polyclonal and of any isotype, e.g., IgM, IgG (e.g. IgG, IgG2, IgG3 or IgG4), IgD, IgA or IgE. Complementarity determining regions (CDRs) of an antibody or single chain variable fragments (Fvs) of an antibody against a target cell surface marker can be grafted or engineered into an antibody of choice to confer specificity for the target cell surface marker upon that antibody. For example, the CDRs of an antibody against a target cell surface marker can be grafted onto a human antibody framework of a known three dimensional structure (see, e.g., International Patent Application Publications WO 1998/045322 and WO 1987/002671; U.S. Pat. Nos. 5,859,205; 5,585,089; and 4,816,567; European Patent Application Publication 0173494; Jones et al., *Nature*, 321: 522 (1986); Verhoeyen et al., *Science*, 239: 1534 (1988), Riechmann et al., *Nature*, 332: 323 (1988); and Winter & Milstein, *Nature*, 349: 293 (1991)) to form an antibody that may raise little or no immunogenic response when administered to a human. In a preferred embodiment, the targeting moiety is a monoclonal antibody.

The antigen binding portion can be any portion that has at least one antigen binding site, such as, e.g., the variable regions or CDRs of the intact antibody. Examples of antigen binding portions of antibodies include, but are not limited to, a heavy chain, a light chain, a variable or constant region of a heavy or light chain, a single chain variable fragment (scFv), or an Fc, Fab, Fab', Fv, or F(ab)$_2$' fragment; single domain antibodies (see, e.g., Wesolowski, *Med Microbiol Immunol.*, 198 (3): 157-74 (2009); Saerens et al., *Curr. Opin. Pharmacol.*, 8 (5):6 00-8 (2008); Harmsen and de Haard, *Appl. Microbiol. Biotechnol.*, 77 (1): 13-22 (2007), helix-stabilized antibodies (see, e.g., Arndt et al., *J. Mol. Biol.*, 312: 221-228 (2001); triabodies; diabodies (European Patent Application Publication 0404097; International Patent Application Publication WO 1993/011161; and Hollinger et al., *Proc. Natl. Acad. Sci. USA*, 90: 6444-6448 (1993)); single-chain antibody molecules ("scFvs," see, e.g., U.S. Pat. No. 5,888,773); disulfide stabilized antibodies ("dsFvs," see, e.g., U.S. Pat. Nos. 5,747,654 and 6,558,672), and domain antibodies ("dAbs," see, e.g., Holt et al., *Trends Biotech*, 21 (11):484-490 (2003), Ghahroudi et al., *FEBS Lett.*, 414:521-526 (1997), Lauwereys et al., *EMBO J* 17:3512-3520 (1998), Reiter et al., *J. Mol. Biol.* 290:685-698 (1999); and Davies and Riechmann, *Biotechnology*, 13:475-479 (2001)).

Methods of testing antibodies or antigen binding portions thereof for the ability to bind to any cell surface marker are known in the art and include any antibody-antigen binding assay, such as, for example, radioimmunoassay (RIA) ELISA, Western blot, immunoprecipitation, and competitive inhibition assays (see, e.g., Janeway et al., infra, and U.S. Patent Application Publication 2002/0197266 A1).

Suitable methods of making antibodies are known in the art. For instance, standard hybridoma methods are described in, e.g., Köhler and Milstein, *Eur. J. Immunol.*, 5, 511-519 (1976), Harlow and Lane (eds.), *Antibodies: A Laboratory Manual*, CSH Press (1988), and C. A. Janeway et al. (eds.), *Immunobiology*, 5$^{th}$ Ed., Garland Publishing, New York, N.Y. (2001)). Alternatively, other methods, such as EBV-hybridoma methods (Haskard and Archer, *J. Immunol. Methods*, 74 (2), 361-67 (1984), and Roder et al., *Methods Enzymol.*, 121, 140-67 (1986)), and bacteriophage vector expression systems (see, e.g., Huse et al., *Science*, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication 2002/0197266 A1.

Phage display also can be used to generate the antibody that may be used in the chimeric molecules of the invention. In this regard, phage libraries encoding antigen-binding variable (V) domains of antibodies can be generated using standard molecular biology and recombinant DNA techniques (see, e.g., Sambrook et al. (eds.), *Molecular Cloning, A Laboratory Manual*, 3$^{rd}$ Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Alternatively, antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Alternatively, the antibody can be a genetically-engineered antibody, e.g., a humanized antibody or a chimeric antibody. Humanized antibodies advantageously provide a lower risk of side effects and can remain in the circulation longer. Methods for generating humanized antibodies are known in the art and are described in detail in, for example, Janeway et al., supra, U.S. Pat. Nos. 5,225,539, 5,585,089 and 5,693,761, European Patent 0239400 B1, and United Kingdom Pat. No. 2188638. Humanized antibodies can also be generated using the antibody resurfacing technology described in, for example, U.S. Pat. No. 5,639,641 and Pedersen et al., *J. Mol. Biol.*, 235, 959-973 (1994).

The targeting moiety may specifically bind to any suitable cell surface marker. The choice of a particular targeting moiety and/or cell surface marker may be chosen depending on the particular cell population to be targeted. Cell surface markers are known in the art (see, e.g., Mufson et al., *Front. Biosci.*, 11:337-43 (2006); Frankel et al., *Clin. Cancer Res.*, 6:326-334 (2000); and Kreitman et al., *AAPS Journal*, 8 (3): E532-E551 (2006)) and may be, for example, a protein or a carbohydrate. In an embodiment of the invention, the targeting moiety is a ligand that specifically binds to a receptor on a cell surface. Exemplary ligands include, but are not limited to, vascular endothelial growth factor (VEGF), Fas, TNF-related apoptosis-inducing ligand (TRAIL), a cytokine (e.g., IL-2, IL-15, IL-4, IL-13), a lymphokine, a hormone, and a growth factor (e.g., transforming growth factor (TGFa), neuronal growth factor, epidermal growth factor).

The cell surface marker can be, for example, a cancer antigen. The term "cancer antigen" as used herein refers to any molecule (e.g., protein, peptide, lipid, carbohydrate, etc.) solely or predominantly expressed or over-expressed by a tumor cell or cancer cell, such that the antigen is associated with the tumor or cancer. The cancer antigen can additionally be expressed by normal, non-tumor, or non-cancerous cells. However, in such cases, the expression of the cancer antigen by normal, non-tumor, or non-cancerous cells is not as robust as the expression by tumor or cancer cells. In this regard, the tumor or cancer cells can over-express the antigen or express the antigen at a significantly higher level, as compared to the expression of the antigen by normal, non-tumor, or non-cancerous cells. Also, the cancer antigen can additionally be expressed by cells of a different state of development or maturation. For instance, the cancer antigen can be additionally expressed by cells of the embryonic or fetal stage, which cells are not normally found in an adult host. Alternatively, the cancer antigen can be additionally expressed by stem cells or precursor cells, which cells are not normally found in an adult host.

The cancer antigen can be an antigen expressed by any cell of any cancer or tumor, including the cancers and tumors described herein. The cancer antigen may be a cancer antigen of only one type of cancer or tumor, such that the cancer antigen is associated with or characteristic of only one type of cancer or tumor. Alternatively, the cancer antigen may be a cancer antigen (e.g., may be characteristic) of more than one type of cancer or tumor. For example, the cancer antigen may be expressed by both breast and prostate cancer cells and not expressed at all by normal, non-tumor, or non-cancer cells.

Exemplary cancer antigens to which the targeting moiety may specifically bind include, but are not limited to mucin 1 (MUC1), melanoma associated antigen (MAGE), preferentially expressed antigen of melanoma (PRAME), carcinoembryonic antigen (CEA), prostate-specific antigen (PSA), prostate specific membrane antigen (PSMA), granulocyte-macrophage colony-stimulating factor receptor (GM-CSFR), CD56, human epidermal growth factor receptor 2 (HER2/neu) (also known as erbB-2), CD5, CD7, tyrosinase tumor antigen, tyrosinase related protein (TRP)1, TRP2, NY-ESO-1, telomerase, and p53. In a preferred embodiment, the cell surface marker, to which the targeting moiety specifically binds, is selected from the group consisting of cluster of differentiation (CD) 19, CD21, CD22, CD25, CD30, CD33, CD79b, transferrin receptor, EGF receptor, mesothelin, cadherin, and Lewis Y. Mesothelin is expressed in, e.g., ovarian cancer, mesothelioma, non-small cell lung cancer, lung adenocarcinoma, fallopian tube cancer, head and neck cancer, cervical cancer, and pancreatic cancer. CD22 is expressed in, e.g., hairy cell leukemia, chronic lymphocytic leukemia (CLL), prolymphocytic leukemia (PLL), non-Hodgkin's lymphoma, small lymphocytic lymphoma (SLL), and acute lymphatic leukemia (ALL). CD25 is expressed in, e.g., leukemias and lymphomas, including hairy cell leukemia and Hodgkin's lymphoma. Lewis Y antigen is expressed in, e.g., bladder cancer, breast cancer, ovarian cancer, colorectal cancer, esophageal cancer, gastric cancer, lung cancer, and pancreatic cancer. CD33 is expressed in, e.g., acute myeloid leukemia (AML), chronic myelomonocytic leukemia (CML), and myeloproliferative disorders.

In an embodiment of the invention, the targeting moiety is an antibody that specifically binds to a cancer antigen. Exemplary antibodies that specifically bind to cancer antigens include, but are not limited to, antibodies against the transferrin receptor (e.g., HB21 and variants thereof), antibodies against CD22 (e.g., RFB4 and variants thereof), antibodies against CD25 (e.g., anti-Tac and variants thereof), antibodies against mesothelin (e.g., SS1, MORAb-009, SS, HN1, HN2, MN, MB, and variants thereof) and antibodies against Lewis Y antigen (e.g., B3 and variants thereof). In this regard, the targeting moiety may be an antibody selected from the group consisting of B3, RFB4, SS, SS1, MN, MB, HN1, HN2, HB21, and MORAb-009, and antigen binding portions thereof. Further exemplary targeting moieties suitable for use in the inventive chimeric molecules are disclosed e.g., in U.S. Pat. No. 5,242,824 (anti-transferrin receptor); U.S. Pat. No. 5,846,535 (anti-CD25); U.S. Pat. No. 5,889,157 (anti-Lewis Y); U.S. Pat. No. 5,981,726 (anti-Lewis Y); U.S. Pat. No. 5,990,296 (anti-Lewis Y); U.S. Pat. No. 7,081,518 (anti-mesothelin); U.S. Pat. No. 7,355,012 (anti-CD22 and anti-CD25); U.S. Pat. No. 7,368,110 (anti-mesothelin); U.S. Pat. No. 7,470,775 (anti-CD30); U.S. Pat. No. 7,521,054 (anti-CD25); and U.S. Pat. No. 7,541,034 (anti-CD22); U.S. Patent Application Publication 2007/0189962 (anti-CD22); Frankel et al., Clin. Cancer Res., 6: 326-334 (2000), and Kreitman et al., AAPS Journal, 8 (3): E532-E551 (2006), each of which is incorporated herein by reference. In another embodiment, the targeting moiety may include the targeting moiety of immunotoxins known in the art. Exemplary immunotoxins include, but are not limited to, LMB-2 (Anti-Tac(Fv)-PE38), BL22 and HA22 (RFB4(dsFv)-PE38), SS1P (SS 1 (dsFv)-PE38), HB21-PE40, and variants thereof. In a preferred embodiment, the targeting moiety is the antigen binding portion of HA22. HA22 comprises a disulfide-linked Fv anti-CD22 antibody fragment conjugated to PE38. HA22 and variants thereof are disclosed in International Patent Application Publications WO 2003/027135 and WO 2009/032954, which are incorporated herein by reference.

In an embodiment of the invention, the chimeric molecule comprises a linker. The term "linker" as used herein, refers to any agent or molecule that connects the inventive PE to the targeting moiety. One of ordinary skill in the art recognizes that sites on the inventive PE, which are not necessary for the function of the inventive PE, are ideal sites for attaching a linker and/or a targeting moiety, provided that the linker and/or targeting moiety, once attached to the inventive PE, do(es) not interfere with the function of the inventive PE, i.e., cytotoxic activity, inhibit growth of a target cell, or to treat or prevent cancer. The linker may be capable of forming covalent bonds to both the PE and the targeting moiety. Suitable linkers are known in the art and include, but are not limited to, straight or branched-chain carbon linkers, heterocyclic carbon linkers, and peptide linkers. Where the PE and the targeting moiety are polypeptides, the linker may be joined to the amino acids through side groups (e.g., through a disulfide linkage to cysteine). Preferably, the linkers will be joined to the alpha carbon of the amino and carboxyl groups of the terminal amino acids.

Included in the scope of the invention are functional portions of the inventive PEs and chimeric molecules described herein. The term "functional portion" when used in reference to a PE or chimeric molecule refers to any part or fragment of the PE or chimeric molecule of the invention, which part or fragment retains the biological activity of the PE or chimeric molecule of which it is a part (the parent PE or chimeric molecule). Functional portions encompass, for example, those parts of a PE or chimeric molecule that retain the ability to specifically bind to and destroy or inhibit the growth of target cells or treat or prevent cancer, to a similar extent, the same extent, or to a higher extent, as the parent PE or chimeric molecule. In reference to the parent PE or chimeric molecule, the functional portion can comprise, for instance, about 10% or more, about 25% or more, about 30% or more, about 50% or more, about 68% or more, about 80% or more, about 90% or more, or about 95% or more, of the parent PE or chimeric molecule.

The functional portion can comprise additional amino acids at the amino or carboxy terminus of the portion, or at both termini, which additional amino acids are not found in the amino acid sequence of the parent PE or chimeric molecule. Desirably, the additional amino acids do not interfere with the biological function of the functional portion, e.g., specifically binding to and destroying or inhibiting the growth of target cells, having the ability to treat or prevent cancer, etc. More desirably, the additional amino acids enhance the biological activity, as compared to the biological activity of the parent PE or chimeric molecule.

Included in the scope of the invention are functional variants of the inventive PEs and chimeric molecules described herein. The term "functional variant" as used herein refers to a PE or chimeric molecule having substantial or significant sequence identity or similarity to a parent PE or chimeric molecule, which functional variant retains the biological activity of the PE or chimeric molecule of which it is a variant. Functional variants encompass, for example, those variants of the PE or chimeric molecule described herein (the parent PE or chimeric molecule) that retain the ability to specifically bind to and destroy or inhibit the growth of target cells to a similar extent, the same extent, or to a higher extent, as the parent PE or chimeric molecule. In reference to the parent PE or chimeric molecule, the functional variant can, for instance, be about 30% or more, about 50% or more, about 75% or more, about 80% or more, about 90% or more, about 95% or more, about 96% or more, about 97% or more, about 98% or more, or about 99% or more identical in amino acid sequence to the parent PE or chimeric molecule.

The functional variant can, for example, comprise the amino acid sequence of the parent PE or chimeric molecule with at least one conservative amino acid substitution. Conservative amino acid substitutions are known in the art and include amino acid substitutions in which one amino acid having certain chemical and/or physical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent PE or chimeric molecule with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent PE or chimeric molecule.

The PE or chimeric molecule of the invention can consist essentially of the specified amino acid sequence or sequences described herein, such that other components of the functional variant, e.g., other amino acids, do not materially change the biological activity of the functional variant.

The PE or chimeric molecule of the invention (including functional portions and functional variants) of the invention can comprise synthetic amino acids in place of one or more naturally-occurring amino acids. Such synthetic amino acids are known in the art and include, for example, aminocyclohexane carboxylic acid, norleucine, α-amino n-decanoic acid, homoserine, S-acetyl aminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexyglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The PE or chimeric molecule of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

An embodiment of the invention provides a method of producing the inventive PE comprising (a) recombinantly expressing the PE and (b) purifying the PE. The PEs and chimeric molecules of the invention (including functional portions and functional variants) can be obtained by methods of producing proteins and polypeptides known in the art. Suitable methods of de novo synthesizing polypeptides and proteins are described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; and U.S. Pat. No. 5,449,752. Also, the PEs and chimeric molecules of the invention can be recombinantly expressed using the nucleic acids described herein using standard recombinant methods. See, for instance, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994.

The method further comprises purifying the PE. Once expressed, the inventive PEs may be purified in accordance with purification techniques known in the art. Exemplary purification techniques include, but are not limited to, ammonium sulfate precipitation, affinity columns, and column chromatography, or by procedures described in, e.g., R. Scopes, *Protein Purification*, Springer-Verlag, NY (1982).

Another embodiment of the invention provides a method of producing the inventive chimeric molecule comprising (a) recombinantly expressing the chimeric molecule and (b) purifying the chimeric molecule. The chimeric molecule may be recombinantly expressed and purified as described herein with respect to other aspects of the invention. In an embodiment of the invention, recombinantly expressing the chimeric molecule comprises inserting a nucleotide sequence encoding a targeting moiety and a nucleotide sequence encoding a PE into a vector. The method may comprise inserting the nucleotide sequence encoding the targeting moiety and the nucleotide sequence encoding the PE in frame so that it encodes one continuous polypeptide including a functional targeting moiety region and a functional PE region. In an embodiment of the invention, the method comprises ligating a nucleotide sequence encoding the PE to a nucleotide sequence encoding a targeting moiety so that, upon expression, the PE is located at the carboxyl terminus of the targeting moiety. In an alternative embodiment, the method comprises ligating a nucleotide sequence encoding the PE to a nucleotide sequence encoding a targeting moiety so that, upon expression, the PE is located at the amino terminus of the targeting moiety.

Still another embodiment of the invention provides a method of producing the inventive chimeric molecule comprising (a) recombinantly expressing the inventive PE, (b) purifying the PE, and (c) covalently linking a targeting moiety to the purified PE. The inventive PE may be recombinantly expressed as described herein with respect to other aspects of the invention. The method further comprises covalently linking a targeting moiety to the purified PE. The method of attaching a PE to a targeting moiety may vary according to the chemical structure of the targeting moiety. For example, the method may comprise reacting any one or more of a variety of functional groups e.g., carboxylic acid (COOH), free amine (—NH$_2$), or sulfhydryl (—SH) groups present on the PE with a suitable functional group on the targeting moiety, thereby forming a covalent bind between the PE and the targeting moiety. Alternatively or additionally, the method may comprise derivatizing the targeting moiety or PE to expose or to attach additional reactive functional groups. Derivatizing may also include attaching one or more linkers to the targeting moiety or PE.

In another embodiment of the invention, the inventive PEs and chimeric molecules may be produced using non-recombinant methods. For example, the inventive PEs and chimeric molecules described herein (including functional portions and functional variants) can be commercially synthesized by companies, such as Synpep (Dublin, Calif.), Peptide Technologies Corp. (Gaithersburg, Md.), and Multiple Peptide Systems (San Diego, Calif.). In this respect, the inventive PEs and chimeric molecules can be synthetic, recombinant, isolated, and/or purified.

It may be desirable, in some circumstances, to free the PE from the targeting moiety when the chimeric molecule has reached one or more target cells. In this regard, the inventive chimeric molecules may comprise a cleavable linker. The linker may be cleavable by any suitable means, e.g., enzymatically. For example, when the target cell is a cancer (e.g., tumor) cell, the chimeric molecule may include a linker cleavable under conditions present at the tumor site (e.g. when exposed to tumor-associated enzymes or acidic pH).

An embodiment of the invention provides a nucleic acid comprising a nucleotide sequence encoding any of the inventive PEs or the inventive chimeric molecules described herein. The term "nucleic acid," as used herein, includes "polynucleotide," "oligonucleotide," and "nucleic acid molecule," and generally means a polymer of DNA or RNA, which can be single-stranded or double-stranded, which can be synthesized or obtained (e.g., isolated and/or purified) from natural sources, which can contain natural, non-natural or altered nucleotides, and which can contain a natural, non-natural, or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches, from a random sequence that happened to have only a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive PEs or chimeric molecules. It is generally appreciated that conditions can be rendered more stringent by the addition of increasing amounts of formamide.

The invention also provides a nucleic acid comprising a nucleotide sequence that is about 70% or more, e.g., about 80% or more, about 90% or more, about 91% or more, about 92% or more, about 93% or more, about 94% or more, about 95% or more, about 96% or more, about 97% or more, about 98% or more, or about 99% or more identical to any of the nucleic acids described herein.

The nucleic acids of the invention can be incorporated into a recombinant expression vector. In this regard, the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, which can be synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The recombinant expression vector of the invention can be any suitable recombinant expression vector, and can be used to transform or transfect any suitable host cell. Suitable vectors include those designed for propagation and expansion or for expression or for both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM, and pMAMneo (Clontech). Preferably, the recombinant expression vector is a viral vector, e.g., a retroviral vector.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the inventive PE or chimeric molecule (including functional portions and functional variants), or to the nucleotide sequence which is complementary to or which hybridizes to the nucleotide sequence encoding the PE or chimeric molecule. The selection of promoters, e.g., strong, weak, inducible, tissue-specific, and developmental-specific, is within the ordinary skill of the artisan. Similarly, the combining of a nucleotide sequence with a promoter is also within the ordinary skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell, an adherent cell or a suspended cell, i.e., a cell that grows in suspension. For purposes of producing a recombinant inventive PE or chimeric molecule, the host cell is preferably a prokaryotic cell, e.g., an *E. coli* cell.

Also provided by the invention is a population of cells comprising at least one host cell described herein. The population of cells can be a heterogeneous population comprising the host cell comprising any of the recombinant expression vectors described, in addition to at least one other cell, e.g., a host cell which does not comprise any of the recombinant expression vectors. Alternatively, the population of cells can be a substantially homogeneous population, in which the population comprises mainly (e.g., consisting essentially of) host cells comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population of host cells comprising a recombinant expression vector as described herein.

The inventive PEs, chimeric molecules (including functional portions and functional variants), nucleic acids, recombinant expression vectors, host cells (including populations thereof), and populations of cells can be isolated and/or purified. The teen "isolated" as used herein means having been removed from its natural environment. The term "purified" as used herein means having been increased in purity, wherein "purity" is a relative term, and not to be necessarily construed as absolute purity. For example, the purity can be about 50% or more, about 60% or more, about 70% or more, about 80% or more, about 90% or more, or about 100%. The purity preferably is about 90% or more (e.g., about 90% to about 95%) and more preferably about 98% or more (e.g., about 98% to about 99%).

The inventive PEs, chimeric molecules (including functional portions and functional variants), nucleic acids, recombinant expression vectors, host cells (including populations thereof), and populations of cells, all of which are collectively referred to as "inventive PE materials" hereinafter, can be formulated into a composition, such as a pharmaceutical composition. In this regard, the invention provides a pharmaceutical composition comprising any of the PEs, chimeric molecules (including functional portions and functional variants), nucleic acids, recombinant expression vectors, host cells (including populations thereof), and populations of cells, and a pharmaceutically acceptable carrier. The inventive pharmaceutical composition containing any of the inventive PE materials can comprise more than one inventive PE material, e.g., a polypeptide and a nucleic acid, or two or more different PEs. Alternatively, the pharmaceutical composition can comprise an inventive PE material in combination with one or more other pharmaceutically active agents or drugs, such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used and is limited only by chemico-physical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive PE material, as well as by the particular method used to administer the inventive PE material. Accordingly, there are a variety of suitable formulations of the pharmaceutical composition of the invention. The following formulations for parenteral (e.g., subcutaneous, intravenous, intraarterial, intramuscular, intradermal, interperitoneal, and intrathecal), oral, and aerosol administration are exemplary and are in no way limiting. More than one route can be used to administer the inventive PE materials, and in certain instances, a particular route can provide a more immediate and more effective response than another route.

Topical formulations are well-known to those of skill in the art. Such formulations are particularly suitable in the context of the invention for application to the skin.

Formulations suitable for oral administration can include (a) liquid solutions, such as an effective amount of the inventive PE material dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the inventive PE material in a flavor, usually sucrose and acacia or tragacanth, as well as pastilles comprising the inventive PE material in an inert base, such as gelatin and glycerin, or sucrose and acacia, emulsions, gels, and the like additionally containing such excipients as are known in the art.

The inventive PE material, alone or in combination with other suitable components, can be made into aerosol formulations to be administered via inhalation. These aerosol formulations can be placed into pressurized acceptable propellants, such as dichlorodifluoromethane, propane, nitrogen, and the like. The aerosol formulations also may be formulated as pharmaceuticals for non-pressured preparations, such as in a nebulizer or an atomizer. Such spray formulations also may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inventive PE material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the inventive PE material in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. The requirements for effective pharmaceutical carriers for parenteral compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

It will be appreciated by one of skill in the art that, in addition to the above-described pharmaceutical compositions, the inventive PE materials of the invention can be formulated as inclusion complexes, such as cyclodextrin inclusion complexes, or liposomes.

For purposes of the invention, the amount or dose of the inventive PE material administered should be sufficient to effect a desired response, e.g., a therapeutic or prophylactic response, in the mammal over a reasonable time frame. For example, the dose of the inventive PE material should be sufficient to inhibit growth of a target cell or treat or prevent cancer in a period of from about 2 hours or longer, e.g., 12 to 24 or more hours, from the time of administration. In certain embodiments, the time period could be even longer. The dose will be determined by the efficacy of the particular inventive PE material and the condition of the mammal (e.g., human), as well as the body weight of the mammal (e.g., human) to be treated.

Many assays for determining an administered dose are known in the art. An administered dose may be determined in vitro (e.g., cell cultures) or in vivo (e.g., animal studies). For example, an administered dose may be determined by determining the $IC_{50}$ (the dose that achieves a half-maximal inhibition of symptoms), $LD_{50}$ (the dose lethal to 50% of the population), the $ED_{50}$ (the dose therapeutically effective in 50% of the population), and the therapeutic index in cell culture and/or animal studies. The therapeutic index is the ratio of $LD_{50}$ to $ED_{50}$ (i.e., $LD_{50}/ED_{50}$).

The dose of the inventive PE material also will be determined by the existence, nature, and extent of any adverse side effects that might accompany the administration of a particular inventive PE material. Typically, the attending physician will decide the dosage of the inventive PE material with which to treat each individual patient, taking into consideration a variety of factors, such as age, body weight, general health, diet, sex, inventive PE material to be administered, route of administration, and the severity of the condition being treated. By way of example and not intending to limit the invention, the dose of the inventive PE material can be about 0.001 to about 1000 mg/kg body weight of the subject being treated/day, from about 0.01 to about 10 mg/kg body weight/day, about 0.01 mg to about 1 mg/kg body weight/day, from about 1 to about to about 1000 mg/kg body weight/day, from about 5 to about 500 mg/kg body weight/day, from about 10 to about 250 mg/kg body weight/day, about 25 to about 150 mg/kg body weight/day, or about 10 mg/kg body weight/day.

Alternatively, the inventive PE materials can be modified into a depot form, such that the manner in which the inventive PE material is released into the body to which it is administered is controlled with respect to time and location within the body (see, for example, U.S. Pat. No. 4,450,150). Depot forms of inventive PE materials can be, for example, an implantable composition comprising the inventive PE materials and a porous or non-porous material, such as a polymer, wherein the inventive PE materials is encapsulated by or diffused throughout the material and/or degradation of the non-porous material. The depot is then implanted into the desired location within the body and the inventive PE materials are released from the implant at a predetermined rate.

The inventive PE materials may be assayed for cytoxicity by assays known in the art. Examples of cytotoxicity assays include a WST assay, which measures cell proliferation using the tetrazolium salt WST-1 (reagents and kits available from Roche Applied Sciences), as described in International Patent Application Publication WO 2011/032022.

It is contemplated that the inventive pharmaceutical compositions, PEs, chimeric molecules, nucleic acids, recombinant expression vectors, host cells, or populations of cells can be used in methods of treating or preventing cancer. Without being bound by a particular theory or mechanism, it is believed that the inventive PEs destroy or inhibit the growth of cells through the inhibition of protein synthesis in eukaryotic cells, e.g., by the inactivation of the ADP-ribosylation of elongation factor 2 (EF-2). Without being bound to a particular theory or mechanism, the inventive chimeric molecules recognize and specifically bind to cell surface markers, thereby delivering the cytotoxic PE to the population of cells expressing the cell surface marker with minimal or no cross-reactivity with cells that do not express the cell surface marker. In this way, the cytoxicity of PE can be targeted to destroy or inhibit the growth of a particular population of cells, e.g., cancer cells. In this regard, the invention provides a method of treating or preventing cancer in a mammal comprising administering to the mammal any of the PEs, chimeric molecules, nucleic acids, recombinant expression vectors, host cell, population of cells, or pharmaceutical compositions described herein, in an amount effective to treat or prevent cancer in the mammal.

The terms "treat" and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

For purposes of the inventive methods, wherein host cells or populations of cells are administered, the cells can be cells that are allogeneic or autologous to the host. Preferably, the cells are autologous to the host.

With respect to the inventive methods, the cancer can be any cancer, including any of adrenal gland cancer, sarcomas (e.g., synovial sarcoma, osteogenic sarcoma, leiomyosarcoma uteri, angiosarcoma, fibrosarcoma, rhabdomyosarcoma, liposarcoma, myxoma, rhabdomyoma, fibroma, lipoma, and teratoma), lymphomas (e.g., small lymphocytic lymphoma, Hodgkin lymphoma, and non-Hodgkin lymphoma), hepatocellular carcinoma, glioma, head cancers (e.g., squamous cell carcinoma), neck cancers (e.g., squamous cell carcinoma), acute lymphocytic cancer, leukemias (e.g., hairy cell leukemia, myeloid leukemia (acute and chronic), lymphatic leukemia (acute and chronic), pro-lymphocytic leukemia (PLL), myelomonocytic leukemia (acute and chronic), and lymphocytic leukemia (acute and chronic)), bone cancer (osteogenic sarcoma, fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochondroma (osteocartilaginous exostoses), benign chondroma, chondroblastoma, chondromyxoid fibroma, osteoid osteoma, and giant cell tumors), brain cancer (astrocytoma, medulloblastoma, glioma, ependymoma, germinoma (pinealoma), glioblastoma multiforme, oligodendroglioma, schwannoma, and retinoblastoma), fallopian tube cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva (e.g., squamous cell carcinoma, intraepithelial carcinoma, adenocarcinoma, and fibrosarcoma), myeloproliferative disorders (e.g., chronic myeloid cancer), colon cancers (e.g., colon carcinoma), esophageal cancer (e.g., squamous cell carcinoma, adenocarcinoma, leiomyosarcoma, and lymphoma), cervical cancer (cervical carcinoma and pre-invasive cervical dysplasia), gastric cancer, gastrointestinal carcinoid tumor, hypopharynx cancer, larynx cancer, liver cancers (e.g., hepatocellular carcinoma, cholangiocarcinoma, hepatoblastoma, angiosarcoma, hepatocellular adenoma, and hemangioma), lung cancers (e.g., bronchogenic carcinoma (squamous cell, undifferentiated small cell, undifferentiated large cell, and adenocarcinoma), alveolar (bronchiolar) carcinoma, bronchial adenoma, chondromatous hamartoma, small cell lung cancer, non-small cell lung cancer, and lung adenocarcinoma), malignant mesothelioma, skin cancer (e.g., melanoma, basal cell carcinoma, squamous cell carcinoma, Kaposi's sarcoma, nevi, dysplastic nevi, lipoma, angioma, dermatofibroma, and keloids), multiple myeloma, nasopharynx cancer, ovarian cancer (e.g., ovarian carcinoma (serous cystadenocarcinoma, mucinous cystadenocarcinoma, endometrioid carcinoma, and clear cell adenocarcinoma), granulosa-theca cell tumors, Sertoli-Leydig cell tumors, dysgerminoma, and malignant teratoma), pancreatic cancer (e.g., ductal adenocarcinoma, insulinoma, glucagonoma, gastrinoma, carcinoid tumors, and VIPoma), peritoneum, omentum, mesentery cancer, pharynx cancer, prostate cancer (e.g., adenocarcinoma and sarcoma), rectal cancer, kidney cancer (e.g., adenocarcinoma, Wilms tumor (nephroblastoma), and renal cell carcinoma), small intestine cancer (adenocarcinoma, lymphoma, carcinoid tumors, Kaposi's sarcoma, leiomyoma, hemangioma, lipoma, neurofibroma, and fibroma), soft tissue cancer, stomach cancer (e.g., carcinoma, lymphoma, and leiomyosarcoma), testicular cancer (e.g., seminoma, teratoma, embryonal carcinoma, teratocarcinoma, choriocarcinoma, sarcoma, Leydig cell tumor, fibroma, fibroadenoma, adenomatoid tumors, and lipoma), cancer of the uterus (e.g., endometrial carcinoma), thyroid cancer, and urothelial cancers (e.g., squamous cell carcinoma, transitional cell carcinoma, adenocarcinoma, ureter cancer, and urinary bladder cancer).

As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

Also provided is a method of inhibiting the growth of a target cell comprising contacting the cell with the PE of any of the PEs, chimeric molecules, nucleic acids, recombinant expression vectors, host cell, population of cells, or pharmaceutical compositions described herein, in an amount effective to inhibit growth of the target cell. The growth of the target cell may be inhibited by any amount, e.g., by about 10% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 100%. The target cell may be provided in a biological sample. A biological sample may be obtained from a mammal in any suitable manner and from any suitable source. The biological sample may, for example, be obtained by a blood draw, leukapheresis, and/or tumor biopsy or necropsy. The contacting step can take place in vitro or in vivo with respect to the mammal. Preferably, the contacting is in vitro.

In an embodiment of the invention, the target cell is a cancer cell. The target cell may be a cancer cell of any of the cancers described herein. In an embodiment of the invention, the target cell may express a cell surface marker. The cell surface marker may be any cell surface marker described herein with respect to other aspects of the invention. The cell surface marker may be, for example, selected from the group consisting of CD19, CD21, CD22, CD25, CD30, CD33, CD79b, transferrin receptor, EGF receptor, mesothelin, cadherin, and Lewis Y.

The following examples further illustrate the invention but, of course, should not be construed as in any way limiting its scope.

Example 1

This example demonstrates the frequency of HLA class 2 alleles in a naïve donor cohort as compared to that of the world population.

Peripheral blood mononuclear cells (PBMC) were isolated from 65 healthy donors obtained from the NIH blood bank and 50 patients undergoing treatment with immunotoxin at the NCI. PBMC were isolated from buffy coats by Ficoll density centrifugation. The HLA class I and class II haplotypes of the PBMC of patients and healthy donors were identified using a PCR-SSP/SSO-based tissue typing kit. PBMC were then frozen in heat-inactivated human AB serum and standard freezing media and stored in liquid nitrogen until used.

Figure 1:
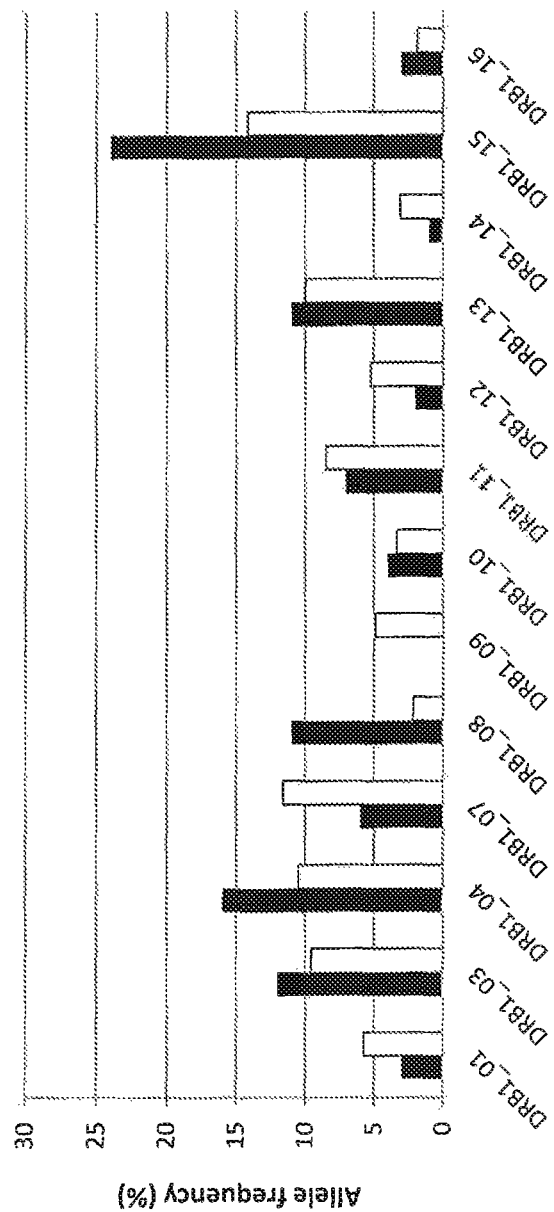

A cohort of 65 healthy donors was studied to provide information on the number and frequency of HLA DR allotypes expressed in the world population. Analysis of the allotypes expressed in the naïve donor cohort was compared with the world population (Middleton, D. et al., New Allele Frequency Database: <www.allelefrequencies.net>, *Tissue Antigens*, 61(5): 403-7(2003)), which showed that there was a reasonable representation of the major HLA class II DRB1 alleles in the naïve donor cohort. Statistical analysis showed a correlation between the world population and the donor cohort of $R^2=0.52$. FIG. 1 compares the frequency of the different types of HLA class 2 alleles in the world population with the naïve donor cohort. Table 1 shows the HLA class II DRB1 haplotypes of the donor population.

TABLE 1

| Donor No. | Donor ID | HLA II DRB1 alleles | |
|---|---|---|---|
| 1 | 10710aph | 1001 | 1501 |
| 2 | 021610aph | 15 | 1501 |
| 3 | 030210aph | 12 | 1602 |
| 4 | 030910aph | 0301 | 401 |
| 5 | 031810aph | 0301 | 1501 |
| 6 | 033010aph | 08 | 15 |
| 7 | 040110aph | 0804 | 13 |
| 8 | 040610aph | 3021 | 1503 |
| 9 | 040810aph | 0407 | 15 |
| 10 | 041310aph | 0101 | 301 |
| 11 | 080409aph | 0701 | 1302 |
| 12 | 081209aph | 1404 | 1501 |
| 13 | 111909aph | 1001 | 15 |
| 14 | 101909aph | 0401 | 0404 |
| 15 | 020210aph | 03 | 0401 |
| 16 | 020410aph | 0402 | 1101 |
| 17 | 122209aph | 12 | 1602 |
| 18 | 122910aph | 0301 | 1101 |
| 19 | 010510aph | 1301 | 1503 |
| 20 | 011410aph | 0301 | 03 |
| 21 | 111209aph | 0804 | 1101 |
| 22 | 110909aph | 1001 | 1602 |
| 23 | 030410aph | 0401 | 1501 |
| 24 | 011210aph | 0401 | 1304 |
| 25 | 101509aph | 0101 | 0301 |
| 26 | 102609aph | 0404 | 0802 |
| 27 | 100509aph | 07 | 07 |
| 28 | 082509aph | 0803 | 1502 |
| 29 | 120809aph | 1101 | 1302 |
| 30 | 030211aph | 03 | 11 |
| 31 | 090109aph | 0301 | 1303 |

TABLE 1-continued

| Donor No. | Donor ID | HLA II DRB1 alleles | |
|---|---|---|---|
| 32 | 092809aph | 0405 | 1303 |
| 33 | 032510aph | 07 | 1501 |
| 34 | 121709aph | 1101 | 1502 |
| 35 | 012110aph | 0401 | 07 |
| 36 | 082709aph | 0401 | 1302 |
| 37 | 021611aph | 04 | 13 |
| 38 | 100109aph | 0401 | 1502 |
| 39 | 031611aph | 804 | 1303 |
| 40 | 011910aph | 1001 | 15 |
| 41 | 032311aph | 1501 | 1502 |
| 42 | 041311aph | 0301 | 0701 |
| 43 | 072309aph | 0803 | 1502 |
| 44 | 071311aph | 01 | 07 |
| 45 | 073009aph | 0804 | 1503 |
| 46 | 042011aph | 0806 | 1501 |
| 47 | 060811aph | 01 | 13 |
| 48 | 061511aph | 0802 | 1503 |
| 49 | 051111aph | 0405 | 11 |
| 50 | 062911aph | 0404 | 15 |

Example 2

This example demonstrates the preparation of a peptide library to be used to stimulate T cells.

To determine the immunogenicity of the toxin moiety, a library of 111 peptides was designed, spanning the entire sequence of PE38. The peptides each had a size of 15 amino acids and overlapped by 12 amino acids with the exception of peptide SEQ ID NOs: 31 and 32, which overlapped by 11 amino acids. The peptides were synthesized at >95% purity as determined by high performance liquid chromatography (HPLC) (American Peptide Co. Inc., Sunnyvale, Calif.). The lyophilized synthetic peptides were dissolved in dimethyl sulfoxide (DMSO) to make 10 μM stock solutions.

The peptides were grouped into 22 pools as shown in Table 2. Table 2 shows the sequences, SEQ ID NOs, and pool numbers of the peptides used for epitope mapping.

TABLE 2

| SEQ ID NO: | Sequence | pool |
|---|---|---|
| 31 | PEGGSLAALTAHQAC | 1 |
| 32 | SLAALTAHQACHLPL | 1 |
| 33 | ALTAHQACHLPLETF | 1 |
| 34 | AHQACHLPLETFTRH | 1 |
| 35 | ACHLPLETFTRHRQP | 1 |
| 36 | LPLETFTRHRQPRGW | 2 |
| 37 | ETFTRHRQPRGWEQL | 2 |
| 38 | TRHRQPRGWEQLEQC | 2 |
| 39 | RQPRGWEQLEQCGYP | 2 |
| 40 | RGWEQLEQCGYPVQR | 2 |
| 41 | EQLEQCGYPVQRLVA | 3 |
| 42 | EQCGYPVQRLVALYL | 3 |
| 43 | GYPVQRLVALYLAAR | 3 |
| 44 | VQRLVALYLAARLSW | 3 |
| 45 | LVALYLAARLSWNQV | 3 |
| 46 | LYLAARLSWNQVDQV | 4 |
| 47 | AARLSWNQVDQVIRN | 4 |
| 48 | LSWNQVDQVIRNALA | 4 |
| 49 | NQVDQVIRNALASPG | 4 |
| 50 | DQVIRNALASPGSGG | 4 |
| 51 | IRNALASPGSGGDLG | 5 |
| 52 | ALASPGSGGDLGEAI | 5 |
| 53 | SPGSGGDLGEAIREQ | 5 |
| 54 | SGGDLGEAIREQPEQ | 5 |
| 55 | DLGEAIREQPEQARL | 5 |
| 56 | EAIREQPEQARLALT | 6 |
| 57 | REQPEQARLALTLAA | 6 |
| 58 | PEQARLALTLAAAES | 6 |
| 59 | ARLALTLAAAESERF | 6 |
| 60 | ALTLAAAESERFVRQ | 6 |
| 61 | LAAAESERFVRQGTG | 7 |
| 62 | AESERFVRQGTGNDE | 7 |
| 63 | ERFVRQGTGNDEAGA | 7 |
| 64 | VRQGTGNDEAGAANG | 7 |
| 65 | GTGNDEAGAANGPAD | 7 |
| 66 | NDEAGAANGPADSGD | 8 |
| 67 | AGAANGPADSGDALL | 8 |
| 68 | ANGPADSGDALLERN | 8 |
| 69 | PADSGDALLERNYPT | 8 |
| 70 | SGDALLERNYPTGAE | 8 |
| 71 | ALLERNYPTGAEFLG | 9 |
| 72 | ERNYPTGAEFLGDGG | 9 |
| 73 | YPTGAEFLGDGGDVS | 9 |
| 74 | GAEFLGDGGDVSFST | 9 |
| 75 | FLGDGGDVSFSTRGT | 9 |
| 76 | DGGDVSFSTRGTQNW | 10 |
| 77 | DVSFSTRGTQNWTVE | 10 |
| 78 | FSTRGTQNWTVERLL | 10 |
| 79 | RGTQNWTVERLLQAH | 10 |
| 80 | QNWTVERLLQAHRQL | 10 |
| 81 | TVERLLQAHRQLEER | 11 |
| 82 | RLLQAHRQLEERGYV | 11 |

TABLE 2-continued

| SEQ ID NO: | Sequence | pool |
|---|---|---|
| 83 | QAHRQLEERGYVFVG | 11 |
| 84 | RQLEERGYVFVGYHG | 11 |
| 85 | EERGYVFVGYHGTFL | 11 |
| 86 | GYVFVGYHGTFLEAA | 12 |
| 87 | FVGYHGTFLEAAQSI | 12 |
| 88 | YHGTFLEAAQSIVFG | 12 |
| 89 | TFLEAAQSIVFGGVR | 12 |
| 90 | EAAQSIVFGGVRARS | 12 |
| 91 | QSIVFGGVRARSQDL | 13 |
| 92 | VFGGVRARSQDLDAI | 13 |
| 93 | GVRARSQDLDAIWRG | 13 |
| 94 | ARSQDLDAIWRGFYI | 13 |
| 95 | QDLDAIWRGFYIAGD | 13 |
| 96 | DAIWRGFYIAGDPAL | 14 |
| 97 | WRGFYIAGDPALAYG | 14 |
| 98 | FYIAGDPALAYGYAQ | 14 |
| 99 | AGDPALAYGYAQDQE | 14 |
| 100 | PALAYGYAQDQEPDA | 14 |
| 101 | AYGYAQDQEPDARGR | 15 |
| 102 | YAQDQEPDARGRIRN | 15 |
| 103 | DQEPDARGRIRNGAL | 15 |
| 104 | PDARGRIRNGALLRV | 15 |
| 105 | RGRIRNGALLRVYVP | 15 |
| 106 | IRNGALLRVYVPRSS | 16 |
| 107 | GALLRVYVPRSSLPG | 16 |
| 108 | LRVYVPRSSLPGFYR | 16 |
| 109 | YVPRSSLPGFYRTSL | 16 |
| 110 | RSSLPGFYRTSLTLA | 16 |
| 111 | LPGFYRTSLTLAAPE | 17 |
| 112 | FYRTSLTLAAPEAAG | 17 |
| 113 | TSLTLAAPEAAGEVE | 17 |
| 114 | TLAAPEAAGEVERLI | 17 |
| 115 | APEAAGEVERLIGHP | 17 |
| 116 | AAGEVERLIGHPLPL | 18 |
| 117 | EVERLIGHPLPLRLD | 18 |
| 118 | RLIGHPLPLRLDAIT | 18 |
| 119 | GHPLPLRLDAITGPE | 18 |
| 120 | LPLRLDAITGPEEEG | 18 |
| 121 | RLDAITGPEEEGGRL | 19 |
| 122 | AITGPEEEGGRLETI | 19 |
| 123 | GPEEEGGRLETILGW | 19 |
| 124 | EEGGRLETILGWPLA | 19 |
| 125 | GRLETILGWPLAERT | 19 |
| 126 | ETILGWPLAERTVVI | 20 |
| 127 | LGWPLAERTVVIPSA | 20 |
| 128 | PLAERTVVIPSAIPT | 20 |
| 129 | ERTVVIPSAIPTDPR | 20 |
| 130 | VVIPSAIPTDPRNVG | 20 |
| 131 | PSAIPTDPRNVGGDL | 21 |
| 132 | IPTDPRNVGGDLDPS | 21 |
| 133 | DPRNVGGDLDPSSIP | 21 |
| 134 | NVGGDLDPSSIPDKE | 21 |
| 135 | GDLDPSSIPDKEQAI | 21 |
| 136 | DPSSIPDKEQAISAL | 22 |
| 137 | SIPDKEQAISALPDY | 22 |
| 138 | DKEQAISALPDYASQ | 22 |
| 139 | QAISALPDYASQPGK | 22 |
| 140 | SALPDYASQPGKPPR | 22 |
| 141 | PDYASQPGKPPREDL | 22 |

Example 3

This example demonstrates that in vitro expansion of naïve donor T cells improves the sensitivity and response level of the T cells to peptide pools.

In order to mimic the immune response that occurs in patients following treatment and to overcome the low sensitivity and unresponsiveness in naïve donor samples in the short term assay, a 17 day in vitro expansion step was employed to expand the specific T cell population (Oseroff et al., *J. Immunol.*, 185 (2): 943-55 (2010)). The cells were incubated for 14-17 days after stimulation with immunotoxin. For stimulation, immunotoxin LMB9 or B3 (dsFv)-PE38 targeting LeY (Brinkmann et al., *Proc. Natl. Acad. Sci. USA*, 90 (16): 7538-42 (1993)), an antigen not present on human immune cells, was used. On day 14-17, the cells were harvested and assayed by an interleukin (IL)-2 ELISpot assay using the 22 peptide pools of Table 2. The addition of the in vitro expansion step improved the sensitivity and response level of the ELISpot assay (e.g., more spot forming cells (SFC) were observed). The in vitro expansion step allowed the detection of a CD4-specific response from volunteer donors and also reduced the number of cells used for each assay.

Figure 2A:
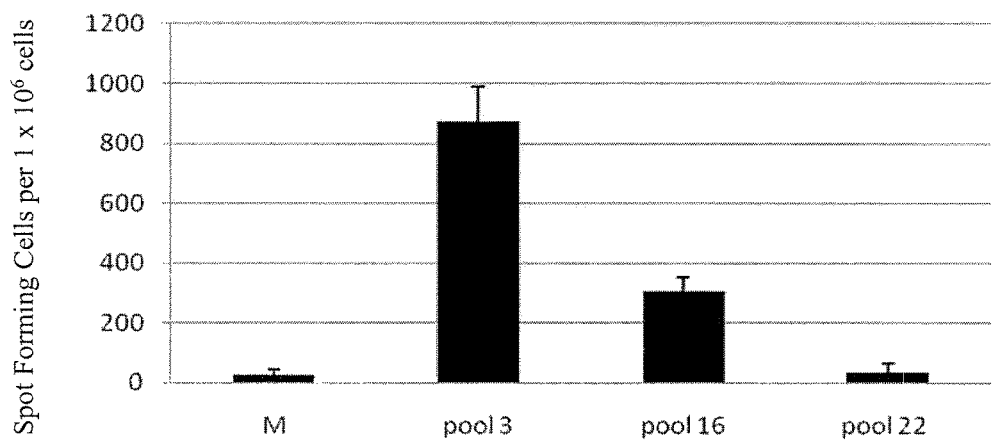
Figure 2B:
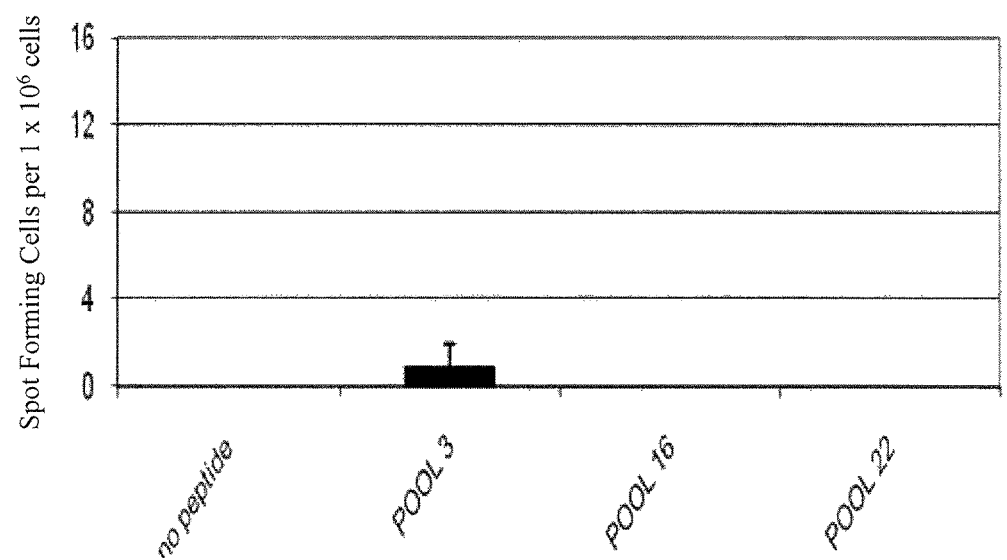

Representative data are shown in FIGS. 2A and 2B. FIG. 2A shows the enumeration of IL-2 ELISpot wells indicating a response of naïve donor 031810aph T cells to initial stimulation of LMB9 (1.6 µg/ml) followed by restimulation with media alone (no peptide) (M) or peptide pools 3, 16, or 22 after 17 days of in vitro expansion. FIG. 2B shows the enumeration of IL-2 ELISpot wells indicating a response of naïve donor 031810aph T cells to initial stimulation of LMB9 (1.6 µg/ml) followed by restimulation with media alone (no peptide) (M) or peptide pools 3, 16, or 22 without in vitro expansion.

Without wishing to be bound to a particular theory or mechanism, it is believed that this approach mimicked the immune response because, as in vivo, the whole recombinant immunotoxin (RIT) was internalized by the antigen presenting cell (APC), processed, and presented during the first few days of culture. The specific T cells that responded to the naturally presented peptides were maintained and expanded using IL-2. The epitopes that those T cells recognized after the 17 days of expansion were naturally processed and naturally presented peptides.

Example 4

This example demonstrates that LVALYLAARLSW (SEQ ID NO: 3) stimulates a T-cell response for most donors.

Following initial stimulation with immunotoxin and 14 days of expansion, half of the cells were harvested and exposed to the peptide pools for an initial pool screen with IL-2 ELISpot. On day 17, the remaining cells were used to repeat the pool screen and a fine screen for the positive pools observed was performed. Different response patterns were observed for the 28 donors on day 14 of the assay. Some donor screens revealed a response to a single pool (e.g., donors 1, 4, 7, and 8) while other donors (e.g., donors 15, 16, and 23) revealed responses to 3-4 pools. Because the peptides overlapped, there was also an overlap between pools such as, for example, cases in which sequential pools had responses (e.g., the response to pools 15 and 16 for donors 15 and 18). A threshold was determined to be 85 SFC/(1× $10^6$). This threshold was determined because for values under 85 SFC/(1×$10^6$), none of the responses from day 14 were reproducible on day 17 or when the in vitro expansion was repeated. Responses over 85 SFC/(1×$10^6$) were reproducible.

Four donors (donors 25-28) had no response (over the determined threshold) to any pool and were considered to be non-responsive. Out of the initial 28 donors that were fully screened, 24 donors had a response to at least one pool. Different donors had different maximal response levels. Some donors (e.g., donors 2, 7, and 10) had a high maximum response (over 1100 SFC for pool 3), while other donors (e.g., donors 3 and 9) had a response of 250-320 SFC to the same pool.

Figure 3:
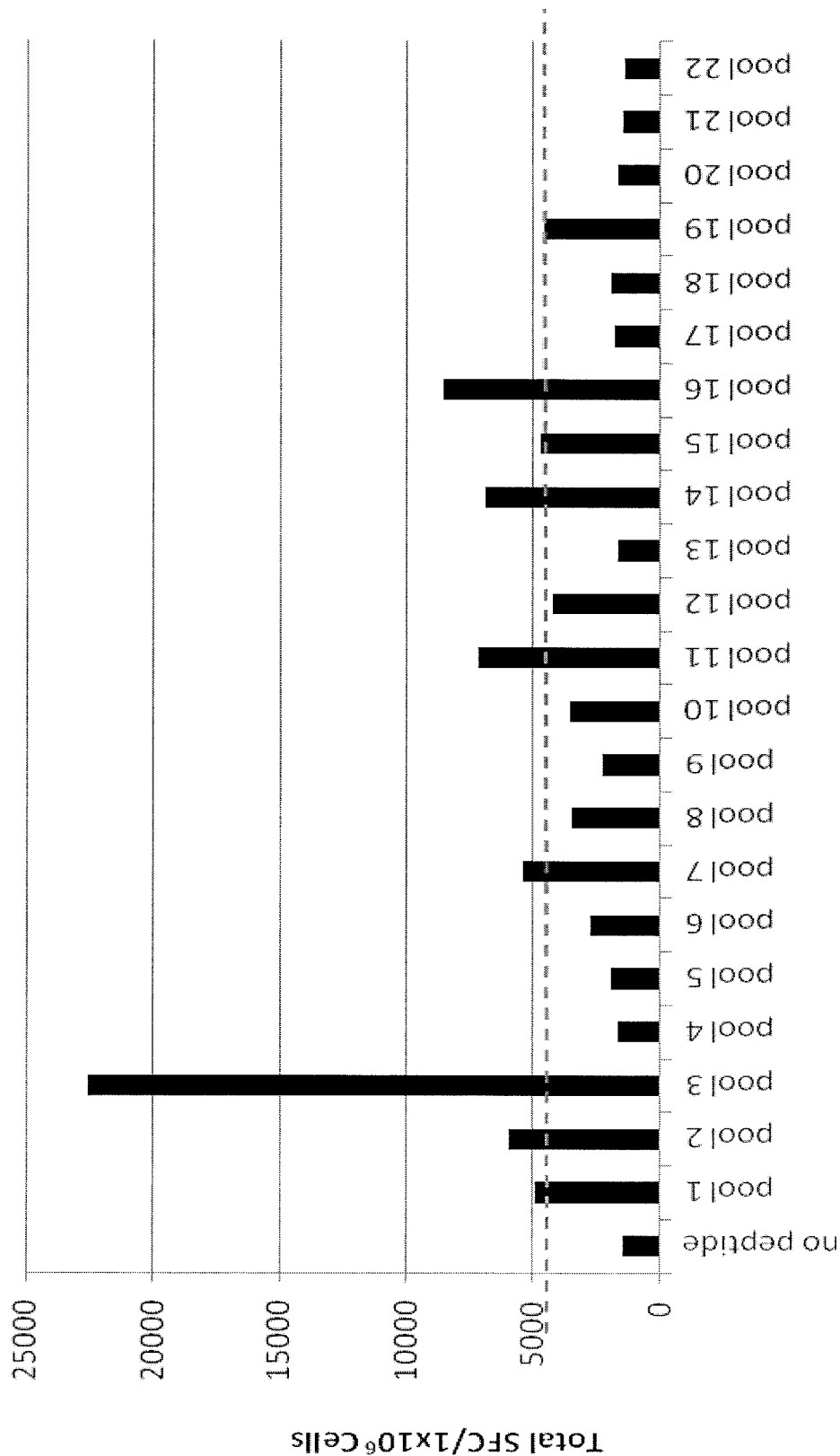

The number of donors screened was increased to 50. The number of spot forming cells observed among all 50 donors was totaled for each of the 22 peptide pools. The results are shown in Table 3 and FIG. 3. An analysis of all 50 donors shows that pool 3 (in PE domain II) gave the most responses (Table 3; FIG. 3). The results suggest that pool 3 was an immunodominant pool, having stimulated responses from many donors with different HLAs.

TABLE 3

| Peptide | Total spots (n = 50) in Spot Forming Cells/1 million cells |
|---|---|
| no peptide | 1434.5 |
| pool 1 | 4947.5 |
| pool 2 | 5952.5 |

TABLE 3-continued

| Peptide | Total spots (n = 50) in Spot Forming Cells/1 million cells |
|---|---|
| pool 3 | 22555 |
| pool 4 | 1667.5 |
| pool 5 | 1925 |
| pool 6 | 2742.5 |
| pool 7 | 5415 |
| pool 8 | 3472.5 |
| pool 9 | 2245 |
| pool 10 | 3572.5 |
| pool 11 | 7147.5 |
| pool 12 | 4235 |
| pool 13 | 1660 |
| pool 14 | 6880 |
| pool 15 | 4750 |
| pool 16 | 8555 |
| pool 17 | 1792.5 |
| pool 18 | 1965 |
| pool 19 | 4597.5 |
| pool 20 | 1680 |
| pool 21 | 1435 |
| pool 22 | 1360 |

A fine screen of pool 3 to find the immunodominant region(s) showed that for most donors, peptide SEQ ID NOs: 44 and 45 were responsible for the response within pool 3 (FIG. 4). FIG. 4 shows that peptide SEQ ID NOs: 44 and 45 contained a common region (LVALYLAARLSW) (SEQ ID NO: 3) for stimulating T cells in most of the patients despite having a different HLA status.

Example 5

This example demonstrates that the substitutions L294A, L297A, Y298A, L299A, or R302A in LVALYLAARLSW (SEQ ID NO: 3) reduces immunogenicity of LVALYLAARLSW (SEQ ID NO: 3).

Peptide SEQ ID NOs: 44 and 45 (within pool 3) have 12 amino acids in common. This common area, LVALYLAARLSW (SEQ ID NO: 3), corresponds to amino acid residue positions 294-305 of SEQ ID NO: 1 and contains both the MHC binding site as well as the T cell receptor binding site. Each amino acid in LVALYLAARLSW (SEQ ID NO: 3) was substituted with alanine. Samples from 9 naïve donors and 2 patients were stimulated with LMB9 for 17 days and assayed using IL-2 ELISpot as described in Example 3. Table 4 summarizes the data from screening 11 samples against the substituted peptides. For 10 out of the 11 samples, one substitution or more diminished the response to under 7% of the response to wild-type (WT). For all donors but one, substitution L297A reduced the response to 7% or less. Y298A reduced the response in 9 out of the 11 samples, and R302A reduced the response in 7 out of the 11 samples. Table 4 shows the percent response of the response obtained with WT peptide.

TABLE 4

|  | Patient 091510 | Patient 012810 | d010710 | d021610 | d031810 | d033010 | d040610 | d010510 | d111909 | d030410 | d122209 |
|---|---|---|---|---|---|---|---|---|---|---|---|
| Media | 0% | 2% | 0% | 1% | 10% | 3% | 1% | 14% | 0% | 0% | 13% |
| WT 15 | 100% | 100% | 100% | 100% | 100% | 100% | 100% | 100% | 100% | 100% | 100% |
| L294A | 5% | 21% | 26% | 6% | 26% | 1% | 7% | 23% | 21% | 3% | 49% |
| L297A | 0% | 2% | 6% | 2% | 6% | 1% | 6% | 6% | 7% | 5% | 52% |
| Y298A | 0% | 0% | 3% | 2% | 17% | 2% | 1% | 3% | 0% | 3% | 19% |
| L299A | 5% | 112% | 1% | 28% | 6% | 78% | 45% | 19% | 14% | 24% | 44% |
| R302A | 14% | 63% | 3% | 6% | 22% | 3% | 7% | 14% | 7% | 5% | 11% |
| L303A | 71% | 356% | 78% | 27% | 46% | 50% | 59% | 28% | 117% | 70% | 85% |
| S304A | 133% | 305% | 82% | 26% | 106% | 69% | 56% | 43% | 117% | 64% | 109% |
| W305A | 186% | 628% | 76% | 58% | 104% | 101% | 64% | 45% | 117% | 132% | 87% |

Without being bound to a particular theory or mechanism, it is believed that the diminished response following a change in a single amino acid may be attributed to an interruption of the binding of the peptide to the groove(s) of the HLA molecule or an inability of the T cell receptor to recognize the changed peptide. In either case, substituted peptides L279A and Y298A caused a diminished response and, therefore, may be considered to be provide reduced immunogenicity.

Example 6

This example demonstrates that the substitution R302A does not create any new T cell epitopes and provides a reduced T cell response.

Figure 5:
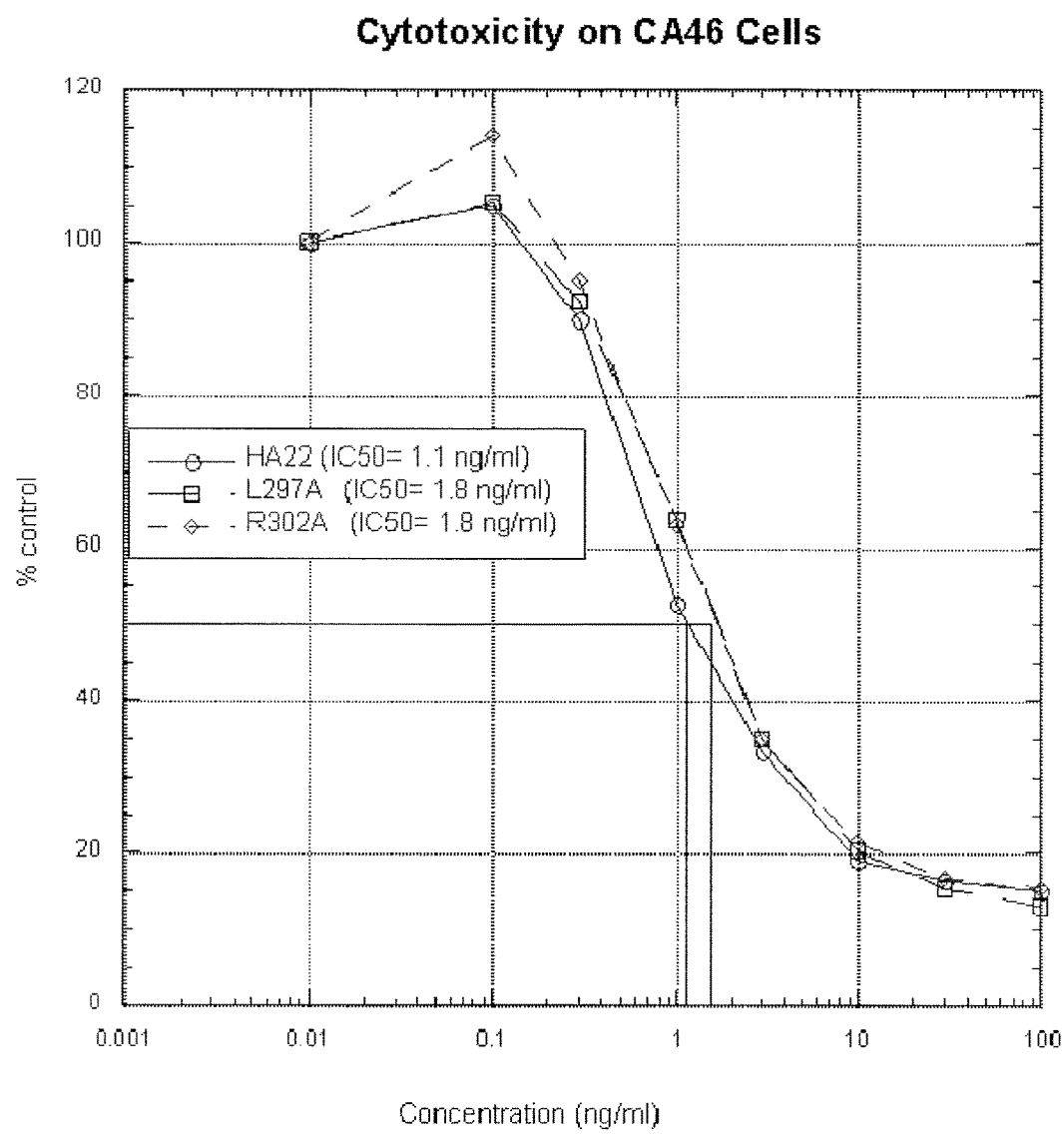
FIG. 5 is a graph showing the cytotoxic activity (% control) (y axis) relative to concentration of wild-type HA22 (a disulfide-linked Fv anti-CD22 antibody fragment conjugated to PE38) (circles), L297A HA22 (squares), or R302A HA22 (diamonds) (ng/ml) (x axis) on CA46 cells.

Site-directed mutagenesis was used to prepare RIT R302 HA22 and L297A HA22 as described previously (Pastan et al., Methods Mol. Biol., 248: 503-18 (2004)). Cytotoxic activity on CA46 cells was compared to that of HA22 wild type (FIG. 5). FIG. 5 shows that HA22 constructs with substitution L297 or R302A were cytotoxic. The IC50 of HA22, L297A HA22, and R302A HA22 was 1.1, 1.8, and 1.8 ng/ml, respectively.

Figure 6A:
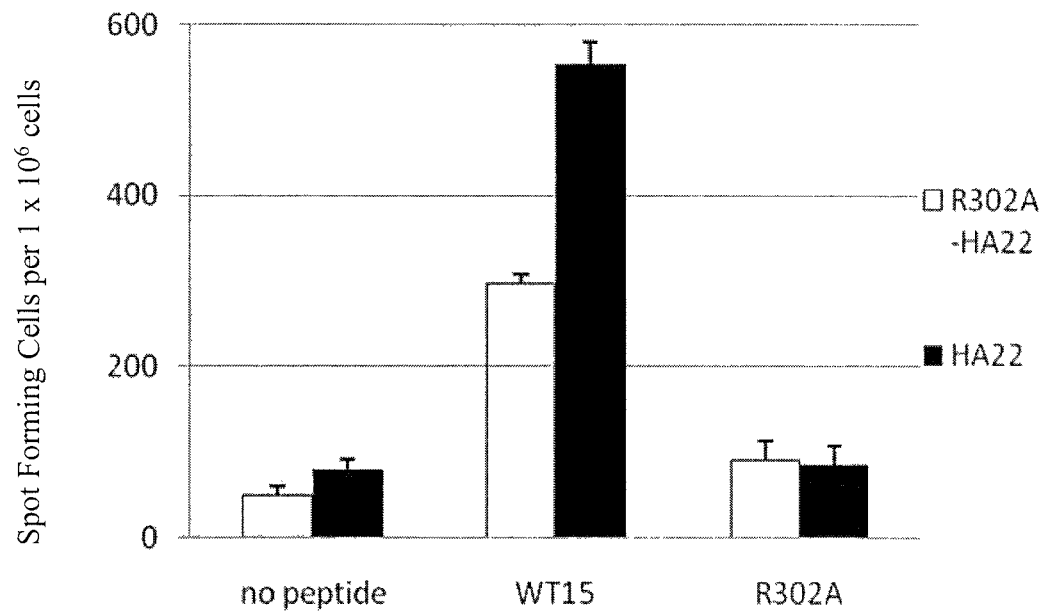
FIG. 6A is a graph showing the T cell response for donor 010710 (SFC per $1 \times 10^6$ cells) (y axis) upon restimulation with no peptide, wild-type peptide (WT15), or R302A (y axis) following culture for 14 days with wild-type HA22 (shaded bars) or R302A HA22 (unshaded bars).
Figure 6B:
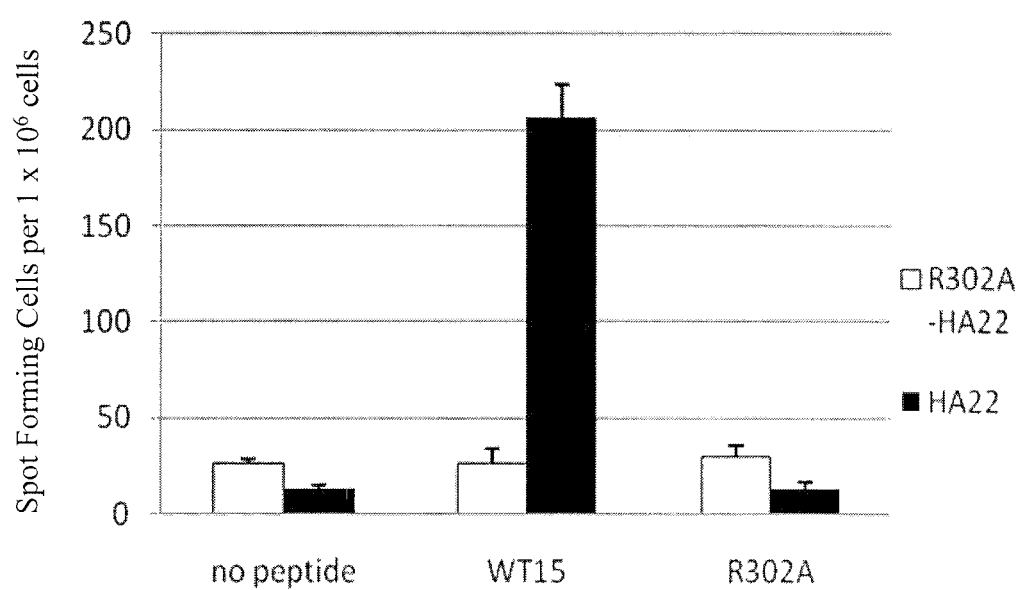
FIG. 6B is a graph showing the T cell response for donor 111909 (SFC per $1 \times 10^6$ cells) (y axis) upon restimulation with no peptide, wild-type peptide (WT15), or R302A (y axis) following culture for 14 days with wild-type HA22 (shaded bars) or R302A HA22 (unshaded bars).

PBMC from donors 010710 and 111909 were cultured for 14 days with either WT HA22 or with HA22-R302A and assayed for T cell response upon restimulation with no peptide, wild-type peptide LVALYLAARLSWNQV (SEQ ID NO: 45) (WT15), or LVALYLAAALSWNQV (SEQ ID NO: 145) (R302A). For both of donors 010710 (FIG. 6A) and 111909 (FIG. 6B), no new epitopes were observed, and the T cell response to the substituted peptide was diminished.

Example 7

This example demonstrates that deletion of the portion of domain II containing the immunodominant epitope reduces the T cell response to the peptides of PE38.

As shown in Example 4, domain II contains an immunodominant and promiscuous epitope (contained in SEQ ID NOs: 44 and 45 of pool 3). PE-LR (resistance to lysosomal degradation) (also known as LR or LR RIT) contains a deletion of domain II except for the furin cleavage sequence RHRQPRGWEQL (SEQ ID NO: 8), which is present in SEQ ID NOs: 37 and 38. Thus, LR RIT contains amino acid residues 274-284 and 395-613 of SEQ ID NO: 1.

The response of donor T cells that were stimulated by HA22 (containing PE38) to the 22 peptide pools of Table 2 was compared to that of donor T cells that were stimulated by PE-LR (that completely lacks the immunodominant epitope).

On Day 0, T cells from three donors (Donor 031510, Donor 021610, or Donor 101509) were plated in 6-well plates and stimulated with 10 µg/ml of either HA22 or PE-LR. On day 14, the cells were harvested and plated in an IL-2 ELISpot plate and incubated with the peptides of one of each of the 22 pools of Table 2 in replicas of 4. Controls included ceftazidime (CEFT)-grown cells, cells with no antigen stimulation on day 0 and no antigen stimulation on day 14 ("M line"), and cells with LMB9 stimulation on day 0 and no antigen stimulation on day 14 ("no peptide").

The results are shown in FIGS. 7A (Donor 031510), 7B (Donor 021610), and 7C (Donor 101509). The T cells from all three donors demonstrated a response upon stimulation with HA22 (containing PE38) and restimulation with the peptides of pool 3. No response was observed for cells that were stimulated with PE-LR.

Example 8

This example demonstrates the identification of T-cell epitopes in PE domain III.

Following initial stimulation with immunotoxin and 14 days of expansion, T cells from 20 donors were harvested and exposed to the peptide pools for an initial pool screen with IL-2 ELISpot as described in Example 4. On day 17, the remaining cells were used to repeat the pool screen and a fine screen with peptides SEQ ID NOs: 102-111 was performed. The results are shown in FIG. 8. The peptides that stimulated IL-2 production by the T cells from each of donors 1-20 are shaded in FIG. 8.

Example 9

This example demonstrates that a substitution of alanine in place of I493, R494, N495, G496, L498, L499, R500, V501 or Y502 reduces the T cell response, as measured by IL-2 production, as compared to the response to wild-type (WT) peptide.

Each non-alanine amino acid in the wild-type peptide IRNGALLRVYVPRSS (SEQ ID NO: 106) was substituted with alanine. Samples from naïve donors were stimulated with LMB9 for 17 days and assayed using IL-2 ELISpot as described in Example 3. Table 5 summarizes the data from screening six samples against the substituted peptides.

TABLE 5

| peptide | \multicolumn{6}{c}{Donors} |
|---|---|---|---|---|---|---|
| | 071509wb | 091510aph | 050710aph | 101910aph | 121709aph | 030211aph |
| WT SEQ ID NO: 106 | 100% | 100% | 100% | 100% | 100% | 100% |
| I493A | 86% | 13% | 0% | 111% | 5% | 6% |
| R494A | 133% | 0% | 2% | 62% | 2% | 12% |
| N495A | 117% | 25% | 2% | 67% | 1% | 35% |
| G496A | 97% | 58% | 18% | 35% | 14% | 18% |
| L498A | 24% | 4% | 0% | 57% | 5% | 0% |
| L499A | 30% | 0% | 0% | 26% | 9% | 6% |
| R500A | 1% | 4% | 24% | 38% | 13% | 24% |
| V501A | 43% | 0% | 7% | 31% | 27% | 0% |
| Y502A | 3% | 4% | 18% | 37% | 37% | 12% |
| V503A | 62% | 58% | 47% | 37% | 36% | 41% |
| P504A | 53% | 125% | 49% | 32% | 56% | 206% |
| R505A | 36% | 83% | 87% | 21% | 95% | 147% |
| S506A | 114% | 138% | 44% | 54% | 55% | 312% |
| S507A | 119% | 96% | 51% | 40% | 100% | 235% |

As shown in Table 5, for all six samples, one substitution or more diminished the response to 10-30% of the response to WT. For five out of six samples, one substitution or more diminished the response to less than 10% of the response to WT. Substitution I493A, R494A, N495A, G496A, L498A, L499A, R500A, V501A or Y502A reduces the T cell response by 70% or more as compared to the response to WT in at least three out of the six samples. Table 5 shows the percent response of the response obtained with WT peptide.

Example 10

This example demonstrates that SEQ ID NOs: 38, 39, 44, 45, 81, 82, 86-88, 97, 98, 105-108, and 123-125 contain T cell epitopes.

Fine screens of all positive pools for 50 donors were performed to determine immunodominant region(s). For each donor, the number of SFC was totaled, and each peptide's relative share of the total number of SFC was calculated and normalized according to the formula (I) below, wherein D represents donor, and x represents one of the 50 donors, P represents peptide, y represents one of the peptides SEQ ID NOs: 31-141, and $S_y$ represents the number of SFC for peptide y:

$$\text{For each } D_x{:}P_y = S_y/\Sigma_{y=1}^{111} S_y \quad \text{(I).}$$

The normalized value represents the level of immunogenicity of each peptide, and the tally of these relative values for 50 donors is shown in FIG. 9. FIG. 9 shows that the following peptides contain T cell epitopes: SEQ ID NOs: 38, 39, 44, 45, 81, 82, 86, 87, 88, 97, 98, 105, 106, 107, 108, 123, 124, and 125.

The most immunogenic peptides in domain III were selected based on the data set forth in FIG. 9. The peptides, the number of donors and patients that responded to the peptide, and the sequences common to the peptides are set forth in Table 6. The patients in Table 6 were previously treated with PE38, and the response shown in Table 6 is a memory response. In Table 6, a response is defined as 5% of a donor's or patient's SFC responding to the peptide.

TABLE 6

| Epitope # | pool | Number of donors that responded to the peptide (n = 50) | Number of patients that responded to the peptide (n = 12) | Sequence | Common sequence |
|---|---|---|---|---|---|
| 1 | 15 | 3 | 6 | RGRIRNGALLRVYVP (SEQ ID NO: 105) | IRNGALLRVYVP |
| | 16 | 5 | 5 | IRNGALLRVYVPRSS (SEQ ID NO: 106) | (SEQ ID NO: 190) |
| | | 4 | 6 | GALLRVYVPRSSLPG (SEQ ID NO: 107) | |
| | | 5 | 7 | LRVYVPRSSLPGFYR (SEQ ID NO: 108) | LRVYVPRSSLPG (SEQ ID NO: 191) |
| 2 | 14 | 4 | 5 | WRGFYIAGDPALAYG (SEQ ID NO: 97) | FYIAGDPALAYG |
| | | 5 | 3 | FYIAGDPALAYGYAQ (SEQ ID NO: 98) | (SEQ ID NO: 192) |
| 3 | 11 | 4 | 4 | TVERLLQAHRQLEER (SEQ ID NO: 81) | RLLQAHRQLEER |
| | | 3 | 4 | RLLQAHRQLEERGYV (SEQ ID NO: 2) | (SEQ ID NO: 193) |
| 4 | 19 | 1 | 0 | GPEEEGGRLETILGW (SEQ ID NO: 123) | EEGGRLETILGW |
| | | 2 | 4 | EEGGRLETILGWPLA (SEQ ID NO: 124) | (SEQ ID NO: 194) |
| | | 2 | 4 | GRLETILGWPLAERT (SEQ ID NO: 125) | GRLETILGWPLA (SEQ ID NO: 195) |

TABLE 6-continued

| Epitope # | pool | Number of donors that responded to the peptide (n = 50) | Number of patients that responded to the peptide (n = 12) | Sequence | | Common sequence |
|---|---|---|---|---|---|---|
| 5 | 12 | 4 | 4 | GYVFVGYHGTFLEAA | (SEQ ID NO: 86) | FVGYHGTFLEAA |
|   |    | 2 | 5 | FVGYHGTFLEAAQSI | (SEQ ID NO: 87) | (SEQ ID NO: 196) |
|   |    | 3 | 3 | YHGTFLEAAQSIVFG | (SEQ ID NO: 88) | YHGTFLEAAQSI |
|   |    |   |   |   |   | (SEQ ID NO: 197) |

Example 11

This example demonstrates that the substitutions R421A, L422A, L423A, A425G, R427A, L429A, Y470A, I471A, A472G, P475A, A476G, L477A, I493A, N495A, R494A, L498A, L499A, R500A, V501A, Y502A, V503A, R505A, L508A, or P509A as defined by reference to SEQ ID NO: 1, reduce immunogenicity of PE.

SEQ ID NO: 106 corresponds to amino acid residue positions 493-507 of SEQ ID NO: 1, SEQ ID NO: 107 corresponds to amino acid residue positions 496-510 of SEQ ID NO: 1, SEQ ID NO: 97 corresponds to amino acid residue positions 466-480 of SEQ ID NO: 1, and SEQ ID NO: 81 corresponds to amino acid residue positions 418-432 of SEQ ID NO: 1. Each amino acid in SEQ ID NO: 106 and SEQ ID NO: 107 was substituted with alanine. Samples from donors and patients were stimulated with LMB9 for 17 days and assayed using IL-2 ELISpot as described in Example 3. Table 7 (SEQ ID NO: 106), Table 8 (SEQ ID NO: 107), Table 9 (SEQ ID NO: 97), and Table 10 (SEQ ID NO: 81) summarize the data (% of the response to wild-type (WT) peptide) from screening the samples against the substituted peptides.

TABLE 7

(SEQ ID NO: 106)

| Donor | Patient | | | | | | | | | | | |
|---|---|---|---|---|---|---|---|---|---|---|---|---|
|  | 1 | 2 | 3 | 4 | 5 | 6 | 7 | 8 | 9 | 10 | 11 | 12 |
| No peptide | 0% | 0% | 0% | 4% | 0% | 9% | 42% | 0% | 1% | 17% | 1% | 0% |
| WT76 | 100% | 100% | 100% | 100% | 100% | 100% | 100% | 100% | 100% | 100% | 100% | 100% |
| I493A | 86% | 13% | 0% | 5% | 6% | 20% | 32% | 110% | 36% | 71% | 76% | 0% |
| R494A | 133% | 0% | 2% | 2% | 12% | 26% | 23% | 111% | 2% | 88% | 94% | 1% |
| N495A | 117% | 25% | 2% | 1% | 35% | 40% | 42% | 102% | 31% | 72% | 72% | 1% |
| G496A | 97% | 58% | 18% | 14% | 18% | 37% | 39% | 96% | 63% | 44% | 99% | 8% |
| L498A | 24% | 4% | 0% | 5% | 0% | 80% | 23% | 6% | 4% | 16% | 31% | 1% |
| L499A | 30% | 0% | 0% | 9% | 6% | 31% | 39% | 30% | 1% | 15% | 57% | 1% |
| R500A | 1% | 4% | 24% | 13% | 24% | 26% | 19% | 1% | 2% | 20% | 6% | 1% |
| V501A | 43% | 0% | 7% | 27% | 0% | 46% | 94% | 25% | 13% | 27% | 48% | 4% |
| Y502A | 3% | 4% | 18% | 37% | 12% | 23% | 42% | 5% | 23% | 20% | 0% | 6% |
| V503A | 62% | 58% | 47% | 36% | 41% | 63% | 55% | 35% | 68% | 27% | 43% | 33% |
| P504A | 53% | 125% | 49% | 56% | 206% | 60% | 55% | 35% | 122% | 26% | 18% | 63% |
| R505A | 36% | 83% | 87% | 95% | 147% | 131% | 123% | 36% | 127% | 23% | 30% | 83% |
| S506A | 114% | 138% | 44% | 55% | 312% | 214% | 104% | 101% | 107% | 55% | 82% | 56% |
| S507A | 119% | 96% | 51% | 100% | 235% | 137% | 97% | 71% | 69% | 83% | 84% | 45% |

TABLE 8

(SEQ ID NO: 107)

| | % of WT | | | | | | |
|---|---|---|---|---|---|---|---|
| | 1 | 2 | 3 | 4 | 5 | 6 | 7 |
| No peptide | 0% | 0% | 7% | 0% | 18% | 9% | 1% |
| wt 77 | 100% | 100% | 100% | 100% | 100% | 100% | 100% |
| G496A | 29% | 51% | 123% | 126% | 58% | 112% | 37% |
| A497G | 103% | 68% | 126% | 102% | 108% | 129% | 71% |
| L498A | 61% | 38% | 140% | 7% | 20% | 13% | 43% |
| L499A | 46% | 24% | 61% | 33% | 26% | 73% | 1% |
| R500A | 59% | 31% | 124% | 1% | 16% | 1% | 6% |
| V501A | 7% | 18% | 28% | 18% | 26% | 49% | 15% |
| Y502A | 14% | 1% | 9% | 4% | 25% | 8% | 0% |
| V503A | 17% | 1% | 9% | 15% | 39% | 49% | 1% |
| P504A | 46% | 32% | 41% | 38% | 43% | 12% | 36% |
| R505A | 7% | 1% | 22% | 28% | 24% | 39% | 2% |
| S506A | 68% | 42% | 50% | 107% | 93% | 122% | 48% |
| S507A | 35% | 37% | 224% | 86% | 106% | 96% | 60% |
| L508A | 8% | 0% | 15% | 73% | 99% | 88% | 46% |
| P509A | 10% | 4% | 16% | 87% | 101% | 119% | 72% |
| G510A | 113% | 144% | 210% | 116% | 114% | 114% | 104% |

As shown in Table 7, substitution I493A, R494A, N495A, L498A, L499A, R500A Y502A, V501A, or Y502A reduces the T cell response by 70% or more as compared to the response to WT peptide.

As shown in Table 8, substitution L498A, L499A, R500A, V501A, Y502A, V503A, R505A, L508A, or P509A reduces the T cell response by 70% or more as compared to the response to WT peptide.

TABLE 9

(SEQ ID NO: 97)

| | % from WT | | | | | | | | | | |
|---|---|---|---|---|---|---|---|---|---|---|---|
| | 1 | 2 | 3 | 4 | 5 | 6 | 7 | 9 | 11 | 12 | 13 |
| No peptide | 0% | 6% | 13% | 1% | 13% | 43% | 26% | 0% | 29% | 47% | 0% |
| WT 67 | 100% | 100% | 100% | 100% | 100% | 100% | 100% | 100% | 100% | 100% | 100% |
| F469A | 80% | 11% | 104% | 35% | 97% | 60% | 88% | 53% | 68% | 60% | 81% |
| Y470A | 61% | 6% | 48% | 67% | 29% | 29% | 16% | 15% | 97% | 92% | 68% |
| I471A | 17% | 7% | 20% | 20% | 22% | 25% | 12% | 17% | 43% | 55% | 35% |
| A472G | 37% | 20% | 84% | 75% | 46% | 31% | 19% | 0% | 60% | 76% | 60% |
| P475A | 72% | 73% | 34% | 57% | 15% | 59% | 16% | 60% | 40% | 70% | 38% |
| A476G | 75% | 110% | 207% | 26% | 67% | 47% | 35% | 24% | 122% | 115% | 32% |
| L477A | 54% | 92% | 25% | 42% | 26% | 43% | 16% | 15% | 67% | 71% | 52% |
| A478G | 80% | 96% | 134% | 24% | 63% | 41% | 98% | 33% | 84% | 66% | 58% |
| Y479A | 114% | 250% | 108% | 117% | 71% | 82% | 21% | 58% | 110% | 94% | 138% |

As shown in Table 9, substitution Y470A, I471A, A472G, P475A, A476G, or L477A reduces the T cell response by 70% or more as compared to the response to WT peptide.

TABLE 10

(SEQ ID NO: 81)

| | % from WT | | | | | | | |
|---|---|---|---|---|---|---|---|---|
| | 1 | 2 | 3 | 4 | 5 | 6 | 7 | 8 |
| No peptide | 13% | 14% | 7% | 0% | 1% | 0% | 1% | 2% |
| WT51 | 100% | 100% | 100% | 100% | 100% | 100% | 100% | 100% |
| R421A | 22% | 12% | 26% | 23% | 87% | 2% | 5% | 19% |
| L422A | 31% | 10% | 16% | 29% | 18% | 0% | 1% | 30% |
| L423A | 8% | 10% | 6% | 47% | 21% | 11% | 3% | 7% |
| A425G | 57% | 16% | 68% | 105% | 51% | 4% | 6% | 112% |
| R427A | 37% | 10% | 35% | 78% | 81% | 1% | 2% | 54% |
| L429A | 28% | 19% | 124% | 63% | 64% | 38% | 36% | 163% |
| E430A | 112% | 26% | 99% | 100% | 100% | 242% | 73% | 112% |
| R432A | 65% | 57% | 142% | 105% | 92% | 87% | 69% | 228% |

As shown in Table 10, substitution R421A, L422A L423A, A425G, R427A, or L429A reduces the T cell response by 70% or more as compared to the response to WT peptide.

Example 12

This example demonstrates that the substitutions Y439A, H440A, F443A, L444A, L446G, A447A, I450A, R551A, L552A, T554A, I555A, L556A or W558A, as defined by reference to SEQ ID NO: 1, reduce immunogenicity of PE.

An 18-mer peptide (GPEEEGGRLETILGWPLA) (SEQ ID NO:198) was synthesized to include amino acid residues from both SEQ ID NOs: 123 and 124. An 18-mer peptide (FVGYHGTFLEAAQSIVFG) (SEQ ID NO: 199) was synthesized to include amino acid residues from both SEQ ID NOs: 87 and 88. SEQ ID NO: 198 corresponds to amino acid residue positions 544-561 of SEQ ID NO: 1, and SEQ ID NO: 199 corresponds to amino acid residue positions 436-453 of SEQ ID NO: 1. Each amino acid in SEQ ID NO: 198 and 199 was substituted with alanine. Samples from donors and patients were stimulated with LMB9 for 17 days and assayed using IL-2 ELISpot as described in Example 3. Table 11 (SEQ ID NO: 198) and Table 12 (SEQ ID NO: 199) summarize the data (% of the response to wild-type (WT) peptide) from screening the samples against the substituted peptides.

TABLE 11

| | % from WT | | | | | | |
|---|---|---|---|---|---|---|---|
| | 1 | 2 | 3 | 4 | 5 | 6 | 7 |
| No peptide | 9% | 2% | 3% | 4% | 3% | 35% | 25% |
| WT 93-94 | 100% | 100% | 100% | 100% | 100% | 100% | 100% |
| E547A | 18% | 254% | 73% | 120% | 122% | 73% | 106% |
| E548A | 24% | 170% | 58% | 98% | 86% | 102% | 207% |
| R551A | 6% | 2% | 62% | 70% | 42% | 40% | 67% |
| L552A | 44% | 10% | 54% | 35% | 11% | 85% | 51% |
| T554A | 9% | 5% | 77% | 133% | 130% | 110% | 95% |
| I555A | 176% | 119% | 111% | 25% | 15% | 63% | 36% |
| L556A | 235% | 3% | 24% | 10% | 13% | 35% | 83% |
| W558A | 200% | 13% | 20% | 26% | 7% | 46% | 54% |
| P559A | 197% | 208% | 24% | 69% | 37% | 65% | 121% |
| L560A | 321% | 162% | 81% | 132% | 117% | 46% | 138% |

As shown in Table 11, substitution R551A, L552A, T554A, I555A, L556A and W558A reduces the T cell response by 70% or more as compared to the response to WT peptide.

TABLE 12

| | % from WT | | | | | | | | | | |
|---|---|---|---|---|---|---|---|---|---|---|---|
| | 1 | 2 | 3 | 4 | 5 | 6 | 7 | 8 | 9 | 10 | 11 |
| No peptide | 0% | 4% | 0% | 0% | 1% | 2% | 10% | 9% | 0% | 1% | 18% |
| WT 57-58 | 100% | 100% | 100% | 100% | 100% | 100% | 100% | 100% | 100% | 100% | 100% |
| F436A | 98% | 7% | 57% | 159% | 89% | 67% | 41% | 123% | 103% | 103% | 94% |
| V437A | 78% | 81% | 84% | 130% | 96% | 77% | 102% | 148% | 97% | 95% | 103% |
| G438A | 52% | 79% | 67% | 78% | 118% | 81% | 98% | 68% | 71% | 88% | 97% |
| Y439A | 96% | 17% | 22% | 21% | 125% | 88% | 110% | 154% | 79% | 97% | 111% |
| H440A | 12% | 6% | 11% | 95% | 108% | 80% | 90% | 102% | 46% | 113% | 105% |
| T442A | 84% | 31% | 77% | 151% | 93% | 77% | 59% | 127% | 48% | 102% | 79% |

TABLE 12-continued

| | % from WT | | | | | | | | | | |
|---|---|---|---|---|---|---|---|---|---|---|---|
| | 1 | 2 | 3 | 4 | 5 | 6 | 7 | 8 | 9 | 10 | 11 |
| F443A | 0% | 7% | 2% | 40% | 1% | 13% | 20% | 7% | 5% | 2% | 17% |
| L444A | 54% | 140% | 69% | 74% | 55% | 11% | 14% | 0% | 9% | 4% | 32% |
| A446G | 40% | 119% | 80% | 47% | 107% | 97% | 69% | 16% | 80% | 37% | 120% |
| A447G | 104% | 103% | 65% | 57% | 118% | 73% | 43% | 7% | 19% | 28% | 98% |
| S449A | 126% | 104% | 98% | 93% | 128% | 116% | 163% | 200% | 23% | 65% | 87% |
| I450A | 159% | 124% | 138% | 130% | 108% | 42% | 31% | 11% | 2% | 66% | 20% |
| V451A | 127% | 121% | 119% | 162% | 142% | 94% | 137% | 50% | 82% | 117% | 119% |
| F452A | 126% | 156% | 119% | 154% | 103% | 169% | 104% | 123% | 99% | 104% | 116% |

As shown in Table 12, substitution Y439A, H440A, F443A, L444A, A446G, A447A, or I450A reduces the T cell response by 70% or more as compared to the response to WT peptide.

Example 13

This example demonstrates the identification of T-cell epitopes in PE.

Based on the results obtained in Examples 4-12, the amino acid sequences set forth in Table 13 were identified as T-cell epitopes of PE.

TABLE 13

| SEQ ID NO: | Amino acid residues with reference to SEQ ID NO: 1 | Sequence |
|---|---|---|
| 200 | 276-287 | RQPRGWEQLEQC |
| 3 | 294-305 | LVALYLAARLSW |
| 193 | 421-432 | RLLQAHRQLEER |
| 199 | 436-453 | FVGYHGTFLEAAQSIVFG |
| 192 | 469-480 | FYIAGDPALAYG |
| 201 | 493-510 | IRNGALLRVYVPRSSLPG |
| 202 | 547-560 | EEGGRLETILGWPL |

Examples 14-16

The following materials and methods were used for Examples 14-16:

Patient's Whole Blood Sample Collection, Storage, and RNA Isolation:

Blood samples were obtained from 6 patients who were treated with recombinant immunotoxins (RITs). 2.5 ml blood samples were collected in PAXGENE tubes containing a cationic detergent and additive salts (PreAnalytiX GmbH, Hombrechtikon, Switzerland), mixed thoroughly by inverting the tube gently 4-6 times and incubated at room temperature 10 hours, and then stored at −80° C. Intracellular RNA from patient's whole blood samples was purified using the PAXGENE Blood RNA Kit (PreAnalytiX) according to the manufacturer's instructions and stored at −80° C.

Heavy Chain and Light Chain cDNA Synthesis, PCR Amplification and Assembly of scFv Genes:

A restriction enzyme site or vector linker was connected (Table 15) to some primers. Heavy chain repertoires and light chain repertoires were prepared separately and connected with a linker to provide ScFv formation. Heavy chain repertoires were prepared from IgG having mature B lymphocytes. The first-strand cDNA synthesis was performed by using a first-strand cDNA synthesis kit (GE Healthcare, NJ) with an IgG constant region primer: HuIgG1-4CH1FOR (Table 15). Light chain repertoires were prepared from Vκ genes using a κ constant region primer: HuGκFOR (Table 15). 40 pmol primers were added into 15 reaction mixture for cDNA synthesis.

$V_H$ and Vκ genes were amplified separately by a three-step process using the first-strand cDNA synthesis production. The IgG constant region primer: HuIgG1-4CH1FOR and an equimolar mixture of the appropriate family-based human $V_H$ back primers (Table 15) were used at the first-step PCR to cover the $V_H$ gene in the intracellular RNA from patient's whole blood samples. A κ constant region primer: HuGκFOR and the appropriate family based human Vκ back primers (Table 15) were used for the Vκ gene. First-step PCR was carried out using high-fidelity polymerase PHUSION (New England Biolabs, Ipswich, Mass.) in a final volume of 500 reaction mixture with 10 pmol of each primer according to the manufacturer's recommendation.

High-fidelity polymerase PRIMESTAR (Takara, Kyoto, Japan) was used for the second step PCR, Splicing by Overlapping Extension (SOE) PCR, and the last step for insert preparation with 10 pmol of each primer according to the manufacturer's recommendation. The sequence of 5'-GCC CAG CCG GCCATGGCC-3' (SEQ ID NO: 185) including an NcoI site (underlined) was connected to human $V_H$ back primers for human $V_H$ back nco primers (Table 15). The pCANTAB vector was used for phage library construction. The sequence of 5'-ACC TCC AGA TCC GCC ACC ACC GGA TCC GCC TCC GCC-3' (SEQ ID NO: 186) including a pCANTAB linker was connected to human $J_H$ forward primers for human $J_H$ forward linker primers. Human $V_H$ back nco primers and human $J_H$ forward linker primers were used in the second PCR to add a Nco I site at the back of the $V_H$ gene and a pCANTAB linker forward of the $V_H$ gene.

At the second step for amplifying the Vκ gene, the sequence of 5'-GGA TCC GGT GGT GGC GGA TCT GGA GGT GGC GGA AGC-3' (SEQ ID NO: 187) including a pCANTAB linker was connected to human Vκ back primers for human Vκ back linker primers. The sequence of 5'-GAG TCA TTC TCG ACT TGCGGCCGC-3' (SEQ ID NO: 184) including a NotI site (double under lined) was connected to human Jκ forward primers for human Jκ forward Not primers. Human Vκ back primers and human Jκ forward primers were used at the second PCR to add a Not I site forward and a pCANTAB linker at the back of Vκ gene.

$V_H$ and Vκ genes were prepared at the third step separately using (a) the primer pair of human $V_H$ back Nco primers and a pCANTAB linker primer of R' linker (Table 15) for the $V_H$ gene, and (b) the primer pair of human Jκ forward not primers and a pCANTAB linker primer of the F' linker (Table 15) for the Vκ gene.

The primers of R' linker and F' linker which were used at the third step were complementary primers. $V_H$ and Vκ genes were combined to provide a ScFv formation using SOE-PCR. Finally, the ScFv library fragment was amplified using the primers of VHIgGFOR and VLREV (Table 15) for insert preparation.

Phage Library Construction:

The amplified ScFv fragment was digested with NcoI and NotI, and subcloned into pCANTAB 5E digested with the same enzymes to construct ScFv library using T4 ligase. The ligation solution was purified by extraction with QIA-QUICK spin column (Qiagen, Valencia, Calif.), and resuspended in water. The resulting concentration was approximately 50 ng/ml. 4 μl samples were electroporated into 50 μl TG1 electrocompetent cells (Lucigen, WI) by using a gene pulser and pulse controller unit (Bio-Rad Laboratories) and repeated 6 times for a large sized library. Cells were incubated in 6 ml of SOC (Invitrogen, Carlsbad, Calif.) for 1 hr at 37° C. with shaking at approximately 250 rpm. A 20 μl sample was collected, diluted, and plated on a TYE ampicillin plate to calculate the library size. 2YT medium in an amount of 6 ml with 200 μg/ml ampicillin and 4% glucose was added and incubated another 1 hr. The medium was made up to 200 ml with 2YT medium with 100 mg/ml ampicillin and 2% glucose. Cells were grown $OD_{600}$=0.4 and infected by $10^{11}$ pfu M13K07 helper phage (New England Biolaboratories) with shaking at 250 rpm for 30 min after standing 30 min. Cells were collected for 5 min at 5,000 rpm in a GSA rotor and resuspended in 2YT medium in an amount of 100 ml with 100 μg/ml ampicillin and 50 μg/ml kanamycin overnight at 30° C. with shaking at 250 rpm.

The phages were precipitated from the supernatant with ⅕ volume of PEG/NaCl (20% polyethylene glycol 6000, 2.5 M NaCl) and resuspended with 2YT medium. The titer of phage library was determined by making serial dilutions of 10 μl of phage and adding 90 μl of TG1 cells, $OD_{600}$=0.4, plated on LB agar supplemented with 100 μg/ml of Amp and 1% glucose. The number of colonies was determined after overnight growth, and the titer was calculated.

Phage Library Panning:

LMB-9 (B3(dsFv)—PE38, specific for a LewisY antigen) was used as antigen for phage library panning. LMB9 was biotinylated using EZ-Link sulfo-NHS-Biotin (Thermo Scientific, Rockford, Ill.) at a molar ratio of 50:1, and the number of biotin groups on each LMB9—biotin was determined using the biotin quantitation kit (Thermo Scientific, Rockford, Ill.) in accordance with the manufacturer's instructions. 350 ml phage and streptavidin modified magnetic beads (DYNABEADS MYONE Streptavidin T1, diameter 1 μm, binding capacity of biotinylated Ig 40-50 μg $mg^{-1}$, hydrophobic, tosyl activated beads (Invitrogen)) were pre-blocked in 3% BSA/PBST (0.1% tween-20). Phage was applied to de-selection with beads.

A magnetic rack was used to separate the beads from the liquid phase causing the beads to become immobilized along the side of the tube. The blocking buffer was removed, and beads were resuspended in phage solution and incubated at room temperature on rotor for 30 min. Phage solution was moved to another tube with pre-blocked beads for additional de-selection. De-selection was repeated with 1 mg beads for two times and 2 mg beads one time. Phage was moved to a pre-blocked tube, and biotinylated LMB9-biotin antigen was added to allow phage-antigen-biotin complexes to form with LMB9-biotin in an amount of 10 μg for the first-round and 5 μg for subsequent rounds. Reaction solution was incubated at room temperature on rotor for 2 hr and removed to a tube with 2 mg beads for an additional 45 min incubation on rotor. The supernatant was removed, and beads were washed 12 times by using PBST. Phage was released from beads by the addition of cold 0.1 M HCl in an amount of 1 μl, and the pH was neutralized with 200 μl Tris-HCl solution (pH 8.0). This is the output of panning, and it was rescued for additional panning rounds, and the titer calculated. The output phage in an amount of 0.6 μl was used to infect 5 ml TG1 (OD600=0.4) for rescue.

Phage ELISA and Phage Clone Sequencing:

Following three or four rounds of panning and phage rescue, 198 single clones from the final round of panning were selected for further analysis. A signal clone was removed to a round-bottom 96-well plate with 150 μl 2YT medium (100 μg/ml ampicillin, 2% glucose) for 4 hr at 37° C. with shaking at 250 rpm, and $10^8$ pfu M13K07 help phage in 50 μl 2YT medium (100 μg/ml ampicillin, 2% glucose) was added into the well with shaking at 250 rpm for 30 min after standing 30 min. Cells were collected by 2700 rpm for 10 min with inserts for 96-well plates and resuspended in 2YT medium in an amount of 200 μl with 100 μg/ml ampicillin and 50μ/ml kanamycin overnight at 30° C. with shaking at 250 rpm. The pellet was resuspended with 100 μl 2YT medium with 100 μg/ml ampicillin, 2% glucose, and 30% glycerol and stored at −80° C. for stock. The phages were precipitated from the supernatant for phage ELISA by 2700 rpm for 10 min. A 96-well flat bottom NUNC MAXISORP plate (Nunc USA, Rochester, N.Y.) was coated with LMB9 (5 μg/ml in PBS) overnight at 4° C. The plate was washed and blocked with 2% nonfat milk (cell signaling). The supernatant with phage (50 μl) and 2% milk (50 μl) were added and incubated for 1 hr at room temperature. The plate was washed 3 times with PBST, and the peroxidase-conjugated anti-M13 (1:1000, GE Healthcare, Waukesha, Wis.) was added for 1 hr at room temperature. The plate was washed 3 times with Phosphate Buffered Saline and Tween 20 (PBST), and 3,3',5,5'-tetramethylbenzidine (TMB) substrate (Thermo Scientific, Rockford, Ill.) was added for 15 min. The results were read in a spectrophotometer at 450 nm to determine the positive and negative clones. The positive clone was picked up for small-scale phage isolation from the appropriate well of stock plate, and the sequencing was performed by using BIGDYE Terminator v1.1 Cycle Sequencing Kit (Applied Biosystems, Foster City, Calif.). The clones with the same sequence were removed, and the resulting sequences were aligned with the IMGT/V-Quest (<www.imgt.org/IMGT_vquest/vquest>).

Competition ICC-ELISA:

The phage-antibody was made with the above mentioned method with a 20 ml scale culture. The dilution of phage-antibody was determined with ELISA. SS1P antibody 50 μl/well, 1 μg/ml in 2% nonfat milk, was added to ELISA plates coated overnight at 4° C. with rFc-mesothelin in an amount of 50 μl/well at a concentration of 4 μg/ml in PBS. The plate was washed 3 times with PBST; phage-antibody with various dilutions was added and detected by using HRP-conjugated anti-M13 and TMB substrate. The dilution of phage-antibody was determined by a dilution curve, and the desired A450 was set at about 1.0. A competition ICC-ELISA assay was conducted to determine the phage-antibody-binding epitope of the PE38 antigen by using patient serum, PE38 without Fv, or the signal mutation in PE38. The phage-antibody was mixed with serial dilutions of the single mutant overnight at 4° C. and added to SS1P-rFc-Mesothelin combination ELISA plate. The competition of the single mutant for the binding of phage-antibody to SS1P was determined by measuring the remaining binding of phage-antibody using HRP-conjugated anti-M13. The competition effect was normalized to the binding to HA22-LR in which PE38 lacked a substitution.

Serum Antigenicity:

The binding of HA22 or substituted HA22 to antibodies in human sera was analyzed in a displacement assay. Human sera were obtained under protocol 1000066. Mesothelin-rFc was added to the ELISA plate (100 ng in 50 μl PBS/well) and incubated overnight 4° C. After washing, an antimesothelin/SS1P (100 ng in 50 μl blocking buffer/well) was added for 1 h to capture unbound human anti-PE38 antibodies. In separate tubes, sera (97- to 30658-fold dilutions) was mixed with 2 μg/ml of HA22 or substituted HA22 and incubated overnight at 4° C. After washing the plate, 50 μl of immunotoxin-antibody mixtures were transferred to each well. The human antibodies not bound to HA22 or substituted HA22 were captured by SS1P and detected by HRP-conjugated rabbit anti-human IgG Fc (Jackson ImmunoResearch Laboratories, West Grove, Pa.), followed by TMB substrate kit (Thermo Scientific Inc., Waltham, Mass.). Binding curves were fitted using a four-parametric logistic curve model by SoftMaxPro 4.0 (Molecular Devices). The $IC_{50}$ values indicate the concentration of RIT that inhibit 50% of the antibody reactivity with SS1P.

Statistics:

Mann-Whitney nonparametric method was used; $p<0.05$ was considered statistically significant.

Example 14

This example demonstrates the isolation and sequencing of human ScFv specific for PE38.

Blood samples were obtained from 6 patients who were treated with different recombinant immunotoxins (RITs) containing PE38 (Table 14). RNA was isolated from blood samples using PAXGENE Blood RNA Kits (PreAnalytiX GmbH, Hombrechtikon, Switzerland). First strand cDNA was synthesized from RNA using primers with the appropriate constant region (Table 15). Single bands of the correct size for $V_H$ and Vκ cDNA were obtained by using first strand cDNA as template. $V_H$ and $V_L$ fragments were amplified individually in three steps. Restriction enzyme site and linker were added into the fragment. 100 ng of the $V_H$ and $V_L$ fragments were combined in a Splicing by Overlapping Extension Polymerase Chain Reaction (SOE-PCR) for scFv formation. The scFv fragment was digested with Nco I and Not I, and subcloned into pCANTAB 5E digested with the same enzymes to construct a scFv library.

TABLE 14

| Library | Disease | Used RITs | Library size × $10^8$ independent clone | Phage library size × $10^{13}$ fpu/ml | Rate of positive clone after fourth round | DNA sequence analysis | Independent clone |
|---|---|---|---|---|---|---|---|
| L1 | ATL | LMB2 | 1.08 | 2.35 | 174/188 | 170 | 14 |
| L2 | HCL | HA22 | 1.27 | 2.3 | 177/188 | 176 | 20 |
| L6 | HCL | BL22 | 1.15 | 2.44 | 14/211 | 14 | 3 |
| L7 | Pleural Mesothelioma | SS1P | 1.05 | 2.06 | 172/190 | 172 | 4 |
| L8 | Pleural Mesothelioma | SS1P | 0.73 | 2.15 | 98/190 | 98 | 63 |
| L9 | Lung cancer | SS1P | 0.86 | 2.29 | 80/190 | 80 | 2 |
| | | | | | | Total: 710 | 103 |

TABLE 15

| SEQ ID NO: | First-strand cDNA synthesis |
|---|---|
| | Human heavy chain constant region primer |
| 146 | HuIgG1-4CH1FOR 5' GTC CAC CTT GGT GTT GCT GGG CTT 3' |
| | Human κ constant region primer |
| 147 | HuGκFOR 5' AGA CTC TCC CCT GTT GAA GCT CTT 3' |
| | First-step PCR |
| | Human VH back primers |
| 148 | HuVH1aBACK 5' CAG GTG CAG CTG GTG CAG TCT GG 3' |
| 149 | HuVH2aBACK 5' CAG GTC AAC TTA AGG GAG TCT GG 3' |
| 150 | HuVH3aBACK 5' GAG GTG CAG CTG GTG GAG TCT GG 3' |
| 151 | HuVH4aBACK 5' CAG GTG CAG CTG CAG GAG TCG GG 3' |
| 152 | HuVH5aBACK 5' GAG GTG CAG CTG TTG CAG TCT GC 3' |
| 153 | HuVH6aBACK 5' CAG GTA CAG CTG CAG CAG TCA GG 3' |
| | Human Vκ back primers |
| 154 | HuVκ 1aBACK 5' GAC ATC CAG ATG ACC CAG TCT CC 3' |
| 155 | HuVκ 2aBACK 5' GAT GTT GTG ATG ACT CAG TCT CC 3' |
| 156 | HuVκ 3aBACK 5' GAA ATT GTG TTG ACG CAG TCT CC 3' |
| 157 | HuVκ 4aBACK 5' GAC ATC GTG ATG ACC CAG TCT CC 3' |
| 158 | HuVκ 5aBACK 5' GAA ACG ACA CTC ACG CAG TCT CC 3' |
| 159 | HuVκ 6aBACK 5' GAA ATT GTG CTG ACT CAG TCT CC 3' |

TABLE 15-continued

| SEQ ID NO: | First-strand cDNA synthesis |
|---|---|
| | Second-step PCR |
| | Human $V_H$ back Nco primers |
| 160 | HuVH1aBACKnco 5' GCC CAG CCG GCC ATG GCC CAG GTG CAG CTG GTG CAG TCT GG 3' |
| 161 | HuVH2aBACKnco 5' GCC CAG CCG GCC ATG GCC CAG GTC AAC TTA AGG GAG TCT GG 3' |
| 162 | HuVH3aBACKnco 5' GCC CAG CCG GCC ATG GCC GAG GTG CAG CTG GTG GAG TCT GG 3' |
| 163 | HuVH4aBACKnco 5' GCC CAG CCG GCC ATG GCC CAG GTG CAG CTG CAG GAG TCG GG 3' |
| 164 | HuVH5aBACKnco 5' GCC CAG CCG GCC ATG GCC GAG GTG CAG CTG TTG CAG TCT GC 3' |
| 165 | HuVH6aBACKnco 5' GCC CAG CCG GCC ATG GCC CAG GTA CAG CTG CAG CAG TCA GG 3' |
| | Human $J_H$ forward linker primers |
| 166 | linkerHuJH12FOR 5' ACC TCC AGA TCC GCC ACC ACC GGA TCC GCC TCC GCC TGA GGA GAC GGT GAC CAG GGT GCC 3' |
| 167 | linkerHuJH3FOR 5' ACC TCC AGA TCC GCC ACC ACC GGA TCC GCC TCC GCC TGA AGA GAC GGT GAC CAT TGT CCC 3' |
| 168 | linkerHulH45FOR 5' ACC TCC AGA TCC GCC ACC ACC GGA TCC GCC TCC GCC TGA GGA GAC GGT GAC CAG GGT TCC 3' |
| 169 | linkerHuJH6FOR 5' ACC TCC AGA TCC GCC ACC ACC GGA TCC GCC TCC GCC TGA GGA GAC GGT GAC CGT GGT CCC 3' |
| | Human Vκ back linker primers |
| 170 | linkerHuVκ 1 aBACK 5' GGA TCC GGT GGT GGC GGA TCT GGA GGT GGC GGA AGC GAC ATC CAG ATG ACC CAG TCT CC 3' |
| 171 | linkerHuVκ 2aBACK 5' GGA TCC GGT GGT GGC GGA TCT GGA GGT GGC GGA AGC GAT GTT GTG ATG ACT CAG TCT CC 3' |
| 172 | linkerHuVκ 3aBACK 5' GGA TCC GGT GGT GGC GGA TCT GGA GGT GGC GGA AGC GAA ATT GTG TTG ACG CAG TCT CC 3' |
| 173 | linkerHuVκ 4aBACK 5' GGA TCC GGT GGT GGC GGA TCT GGA GGT GGC GGA AGC GAC ATC GTG ATG ACC CAG TCT CC 3' |
| 174 | linkerHuVκ 5aBACK 5' GGA TCC GGT GGT GGC GGA TCT GGA GGT GGC GGA AGC GAA ACG ACA CTC ACG CAG TCT CC 3' |
| 175 | linkerHuVκ 6aBACK 5' GGA TCC GGT GGT GGC GGA TCT GGA GGT GGC GGA AGC GAA ATT GTG CTG ACT CAG TCT CC 3' |
| | Human Jκ forward not primers |
| 176 | HuJκ BACKNot 5' GAG TCA TTC TCG ACT TGC GGC CGC ACG TTT GAT TTC CAC CTT GGT CCC 3' |
| 177 | HuJκ 2BACKNot 5' GAG TCA TTC TCG ACT TGC GGC CGC ACG TTT GAT CTC CAG CTT GGT CCC 3' |
| 178 | HuJκ 3BACKNot 5' GAG TCA TTC TCG ACT TGC GGC CGC ACG TTT GAT ATC CAC TTT GGT CCC 3' |
| 179 | HuJκ 4BACKNot 5' GAG TCA TTC TCG ACT TGC GGC CGC ACG TTT GAT CTC CAC CTT GGT CCC 3' |
| 180 | HuJκ 5BACKNot 5' GAG TCA TTC TCG ACT TGC GGC CGC ACG TTT AAT CTC CAG TCG TGT CCC 3' |
| | Third-step PCR |
| 181 | R'linker 5' GCT TCC GCC ACC TCC AGA TCC GCC ACC ACC GGA TCC GCC TCC GCC 3' |
| 182 | F'linker 5' GGC GGA GGC GGA TCC GGT GGT GGC GGA TCT GGA GGT GGC GGA AGC 3' |
| | ScFv fragment preparation |
| 183 | VHIgGFOR 5' GTC CTC GCA ACT GCG GCC CAG CCG GCC ATG GCC 3' |
| 184 | VLREV 5' GAG TCA TTC TCG ACT TGC GGC CGC 3' |

Biotinylated immunotoxin LMB-9 (B3-Fv-PE38) was used as the antigen for selection of phage expressing Fvs that bound to PE38. Each LMB-9 molecule contained 6 biotins. 6 human antibody libraries were obtained by electroporations into *Escherichia coli* (*E. coli*.) TG1 containing $7.3\times10^7$-$1.27\times10^8$ VH-VL scFv clones (Table 15). The phage library was rescued by superinfection with helper phage (Table 15), and 350 ml of each library obtained about $7\times10^{12}$ scFv fragments displayed on the surface of phage.

710 Fv containing phage clones were obtained and sequenced. Sequencing revealed that there were 103 unique human heavy chain and human kappa light chain sequences present except for 2 clones that had the same light chain sequence. To show that the Fvs were derived from B cells making anti-immunotoxin antibodies, competition studies were performed and showed that immune anti-sera blocked the binding of the phage to the PE38 portion of LMB-9, and none of the clones bound to the Fv portion of the immunotoxin. The strength of binding was then measured using an ICC-ELISA. 47 clones had weak binding and were not studied further. The other 56 clones were used to determine the human-specific epitopes in PE38.

Example 15

This example demonstrates the location of human B cell epitopes.

LMB-9 contains both domains II and III of PE. To identify the phage which only binds to domain III, the binding of each clone to HA22-LR, which only had domain III and lacks domain II, was measured. Fifteen of the 56 phage clones could not bind to HA22-LR, indicating that the epitopes recognized by these 15 phage clones were located on domain II. The remaining 41 phage clones were used to identify the residues that make up the B-cell epitopes in domain III by measuring their binding to substituted proteins in which individual amino acids on the surface of domain III of the protein were changed from a large bulky amino acid to alanine or glycine. These substitutions eliminated the large bulky side chains that are involved in antibody recognition and binding. The data are shown in FIG. 10 where clones with poor binding (<10%) are shown in black cells, and substituted proteins with normal reactivity are shown with blank cells. The results show that a single substitution decreased the binding of many clones, thereby indicating that they are in the same epitope group.

The location of residues that, when substituted, reduced phage binding by >90% to various epitopes are shown in Table 16. Amino acids associated with each human (H1, H2, H3, H4, H5 and H6) and mouse (2c, 4a, 4b, 5,6a, 6b, and 7) epitope are shown in Table 16. Human epitope H1 contained D403, R427, and E431. R427 and E431 belonged to mouse epitope 4a, and these residues were involved in both mouse and human antibody binding. Human epitope H2 contained residues R467 and D463, which belonged to mouse epitope 2c, and E548 which belonged to mouse epitope 6a. Y481, L516, E522, and R551 were human specific epitopes. Human H3 epitope contained only R458 that belonged to mouse epitope 4b. Human epitope H4 contained R432 and R505. R432 belonged to mouse epitope 4a and R505 was a human specific residue. Human epitope H5 was composed of R490 and R576, which belonged to mouse epitope 5. Human epitope H6 included R538. R538 belongs to mouse epitope 2c. D406, R412, R513, L597, Q592, and K590 were mouse specific epitopes and not involved in human epitope binding.

TABLE 16

| Human epitopes | |
|---|---|
| H1 | D403, R427, E431 |
| H2 | R551, E548, L516, E522, D463, D461, Y481, R467 |
| H3 | R458 |
| H4 | R505, R432 |
| H5 | R490, R576 |
| H6 | R538 |
| Mouse epitopes | |
| 2c | D463, R467, R538 |
| 4a | R427, E431, R432 |
| 4b | R406, R458 |
| 5 | R412, R490, R576 |
| 6a | L597, R513, E548 |
| 6b | Q592 |
| 7 | K590 |

Phage clones reacting with epitope H1 were affected by substitutions at residues D403, R427, and E431. A substitution of any of these residues with alanine greatly affected the binding of many phages that recognized the epitope (FIG. 10). As expected for substitutions that make up an epitope, these residues were spatially adjacent on domain III. Epitope H2 was complex. The phages reacting with epitope H2 were affected by substitutions at 8 residues. Substituting R467 with alanine destroyed binding of six of the eight phages that defined epitope H2. Substituting residue D463 prevented the binding of four phages, substituting Y481 prevented the binding of three phages, substituting R551 prevented the binding of two phages and, and substituting residues D461, L516, E522, or E548 prevented the binding of one phage. Structurally, these residues resided in a restricted area and made up a cluster. Epitope H3 was recognized by 2 phages that bind to R458. Epitope H4 was recognized by 11 phages and binding was destroyed by a R505A substitution. A substitution at R432, which was close to R505, affected the binding of 1 of the 11 phages. Epitope H5 was recognized by 4 phages. Binding to all four was affected by a substitution at R490 and a substitution at R576 affected binding of three of four phages. These residues were spatially adjacent on domain III, even though they were separated by 86 amino acids in the sequence. A substitution at R538 eliminated binding of one of two phages. In summary, substituting highly exposed surface residues with alanine identified the residues that bind to the phages that bind to domain III, showing that the epitopes were located at distinct sites on the surface of domain III.

Example 16

This example demonstrates the production of a low antigenic recombinant immunotoxin (RIT) for humans.

The identification of individual residues that were involved in binding to human antisera was used to design and construct immunotoxins with substitutions that eliminated reactivity with the human anti-sera yet retained cytotoxic activity and could be produced in sufficient amounts to be useful. In most cases, residues were replaced with alanine, because its small side chain reacts poorly with antibodies and it usually does not affect protein folding. Serine was also used to substantially avoid an especially hydrophobic surface.

Based on the information in the epitope mapping studies, substitutions selected from the different amino acids that destroyed the binding of the human Fvs to domain III of HA22-LR were combined. The substitutions are shown in Table 17 below. LR05 had all the substitutions present in HA22-LR-8M and 4 new substitutions, LR06 had only 2 substitutions from HA22-LR-8M and 4 new substitutions, and LO10 was like LR06 but had an additional 463A substitution (Table 17).

TABLE 17

| LO5: | 406A, 432G, 467A, 490A, 513A, 548S, 590S, 592A, 8M SUBSTITUTION |
|---|---|
| | 427A, 505A, 538A, 458A human epitope |
| LO6: | 467A, 490A, human & mice |
| | 427A, 505A, 538A, 458A human epitope |
| LO10: | 467A, 490A, 427A, 505A, 538A, 458A, 463A |
| LR-LO10R: | 467A, 490A, 427A, 505A, 538A, 463A |

TABLE 18

| Substituted Protein | Substituted residue in domain III | | | | | | | | | | | | | Yield (mg) | Activity (%) |
|---|---|---|---|---|---|---|---|---|---|---|---|---|---|---|---|
| | 406 | 427 | 432 | 458 | 463 | 467 | 490 | 505 | 513 | 538 | 548 | 590 | 592 | | |
| LR-8M | X | | X | | | X | X | | X | | X | X | X | | 100 |
| LO5 | X | X | X | X | | X | X | X | X | X | X | X | X | 3 | 16 |
| LO6 | | X | | X | | X | X | X | | X | | | | 4.3 | 41 |
| LO10 | | X | | X | X | X | X | X | | X | | | | 3 | 60 |
| LR-LO10R | | X | | | X | X | X | X | | X | | | | 5.8 | 141 |

The substituted proteins were expressed and purified. SDS gel analysis showed that the substituted proteins were more than 95% homogeneous. The purified proteins were then analyzed for cytotoxic activity on several CD22 positive cell lines and for antigenicity in terms of their ability to bind to antibodies present in the serum of patients who had made neutralizing antibodies to immunotoxins containing PE38. 25 sera from patients who had received several different immunotoxins (LMB-9, SS1P and HA22) were analyzed.

The data in Table 19 show that all 3 new immunotoxins were active on CD22 positive lymphoma lines with an IC$_{50}$ around 1 ng/ml, but less active than HA22-LR. The most active was HA22-LO10, which was 60% as active as HA22-LR on Daudi cells, 27% as active on Raji cells, and 29% as active on CA46 cells. These new immunotoxins were CD22 specific and had no activity on the A431 cells that do not express CD22 (Table 19).

TABLE 19

| | IC$_{50}$ (ng/ml) | | | |
|---|---|---|---|---|
| | HA22-LR | HA22-LO5 | HA22-LO6 | HA22-LO10 |
| Raji | 0.41 | 3.74 | 2.23 | 1.5 (27%) |
| CA46 | 0.11 | 2.08 | 0.53 | 0.38 (29%) |
| Daudi | 0.18 | 1.25 | 0.57 | 0.3 (60%) |
| A431 | >100 | >100 | >100 | >100 (0%) |

Antigenicity is defined as the binding of immunogens to preexisting antibodies. To assess the antigenicity of the substituted HA22-LO with human patient sera, competition experiments were carried out in which the concentration of each of the substituted immunotoxins that reduced the level of antibodies reacting with HA22 by 50% was measured. Typical competition results with two patient sera are shown in FIGS. 11A and 11B. FIG. 11A shows that the concentration of HA22, HA22-LR, HA22-LO5, HA22-LO6, HA22-LR-8M, and HA22-LO10 at which binding to PE38 was inhibited by 50% (IC$_{50}$) was 84.8, 38.1, 4580, 1440, 3610, >396000 nM, respectively. The binding (IC$_{50}$) ratio of HA22 to HA22-LR, HA22-LO5, HA22-LO6, HA22-LR-8M, and HA22-LO10 was 223, 1.85, 5.89, 2.35, and <0.0214%, respectively. FIG. 11B shows that the concentration of HA22, HA22-LR, HA22-LO5, HA22-LO6, HA22-LR-8M, and HA22-LO10 at which binding to PE38 was inhibited by 50% (IC$_{50}$) was 50.9, 67700, >396000, >396000, >396000, >396000 nM, respectively. The binding (IC$_{50}$) ratio of HA22 to HA22-LR, HA22-LO5, HA22-LO6, HA22-LR-8M, and HA22-LO10 was 0.752, <0.0129, <0.0129, <0.0129, and <0.0129%.

Overall sera from 32 patients who were treated for more than 10 years with PE38 containing immunotoxins SS1P, HA22, and LMB9 were analyzed. The binding ratios using the substituted immunotoxins are shown in Table 20. It was found that the antigenicity of HA22-LR-LO10 with human sera was substantially reduced compared to HA22, HA22-LR, and HA22-LR8M. FIG. 12 is a graph showing percent binding of antibodies to HA22, HA22-LR-8M, HA22-LRLO10, or HA22-LR-LO10R in the sera of patients treated using PE38. HA22-LR-LO10R is similar to HA22-LO10 except that HA22-LR-LO10R lacks the R458A substitution that is present in HA22-LO10 (Tables 17 and 18). FIG. 12 shows that twenty-three of thirty-two patients demonstrated binding (antigenicity) that was reduced by more than 100-fold (100-10000-fold). Only in four of the thirty-two patients could a decrease in antigenicity not be detected.

TABLE 20

| Patient | ITs | Dilution | Binding (%) | | |
|---|---|---|---|---|---|
| | | | HA22 | LR | LO10 | LO10R |
| 1 | BL22 | 1192 | 100 | 1.2072 | 0.0118 | 0.0241 |
| 2 | BL22 | 2057 | 100 | 372.4138 | 493.1507 | 3000.0000 |
| 3 | BL22 | 1231 | 100 | 528.0992 | 358.9888 | 1228.8462 |
| 4 | BL22 | 9485 | 100 | 202.3988 | 431.3099 | 2947.5983 |
| 5 | BL22 | 4187 | 100 | 5.9797 | 0.0021 | 0.0031 |
| 6 | BL22 | 1430 | 100 | 2.2597 | 0.0016 | 0.0033 |
| 7 | BL22 | 6673 | 100 | 50.1718 | 0.0057 | <0.00147 |
| 8 | SS1P | 1698 | 100 | <0.00187 | <0.00187 | <0.00187 |
| 9 | SS1P | 26789 | 100 | <0.0289 | <0.0289 | <0.0289 |
| 10 | SS1P | 3876 | 100 | <0.00686 | <0.00686 | <0.00686 |
| 11 | HA22 | 962 | 100 | <0.00194 | <0.00194 | <0.00194 |
| 12 | HA22 | 10127 | 100 | 0.0219 | <0.00120 | <0.00120 |
| 13 | HA22 | 1093 | 100 | 0.4298 | 0.0056 | <0.00555 |
| 14 | LMB9 | 38802 | 100 | 191.2500 | 0.0031 | 382.5000 |
| 15 | SS1P | 121598 | 100 | 0.0034 | <0.00274 | 0.0060 |
| 16 | SS1P | 379861 | 100 | 0.4770 | <0.00247 | 0.0047 |
| 17 | SS1P | 269987 | 100 | 0.0433 | 0.0019 | 0.0026 |
| 18 | SS1P | 63115 | 100 | 0.0040 | <0.00272 | <0.00272 |
| 19 | SS1P | 12938 | 100 | <0.0623 | <0.0623 | <0.0623 |
| 20 | SS1P | 132398 | 100 | <0.00583 | <0.00583 | 0.0093 |
| 21 | SS1P | 10634 | 100 | <0.00293 | <0.00293 | <0.00293 |
| 22 | SS1P | 17989 | 100 | <0.00893 | <0.00893 | <0.00893 |
| 23 | SS1P | 20184 | 100 | <0.0359 | <0.0359 | <0.0359 |
| 24 | SS1P | 29387 | 100 | <0.00185 | <0.00185 | 0.0019 |
| 25 | SS1P | 77031 | 100 | <0.00755 | <0.00755 | <0.00755 |
| 26 | SS1P | 131839 | 100 | <0.0133 | <0.0133 | <0.0133 |
| 27 | SS1P | 23165 | 100 | 30.4545 | 12.6415 | 26.5347 |
| 28 | SS1P | 1792 | 100 | 17.8081 | 113.0324 | 40.1708 |
| 29 | SS1P | 12443 | 100 | <0.00721 | <0.00721 | <0.00721 |
| 30 | SS1P | 12873 | 100 | <63.3 | <63.3 | <63.3 |
| 31 | SS1P | 4793 | 100 | 100.0000 | 100.0000 | 100.0000 |
| 32 | SS1P | 443961 | 100 | 41.5094 | 9.1667 | 36.3208 |
| Less reactive sera (%) | | | 100 | 59 | 75 | 72 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A *Pseudomonas* exotoxin A (PE) comprising the amino acid sequence of Formula I:

$$FCS\text{-}R^1{}_m\text{—}R^2{}_p\text{—}R^3{}_n\text{-PE functional domain III} \qquad \text{(Formula I)},$$

wherein:

m, n, and p are, independently, 0 or 1;

FCS comprises a furin cleavage amino acid sequence;

$R^1$ comprises 1 or more continuous amino acid residues of residues 285-293 of SEQ ID NO: 1;

$R^2$ comprises $X_1VAX_2X_3X_4AAX_5LSW$ (SEQ ID NO: 2), wherein $X_1$, $X_2$, and $X_4$ are independently leucine, alanine, glycine, serine, or glutamine; $X_3$ is tyrosine, alanine, glycine, serine, or glutamine; and $X_5$ is arginine, alanine, glycine, serine, or glutamine; with the proviso that the PE does not comprise LVALYLAARLSW (SEQ ID NO: 3) and that when $X_5$ is alanine, at least one of $X_1$, $X_2$, $X_3$, and $X_4$ is alanine, glycine, serine, or glutamine;

$R^3$ comprises 1 or more continuous amino acid residues of residues 306-394 of SEQ ID NO: 1; and PE functional domain III comprises residues 395-613 of SEQ ID NO: 1 with a substitution of amino acid residue D463, optionally with a substitution of one or more amino acid residues within one or more B-cell epitopes of SEQ ID NO: 1; and/or optionally with a substitution of one or more amino acid residues within one or more T cell epitopes within amino acid residues R421, L422, L423, A425, R427, L429, Y439, H440, F443, L444, A446, A447, I450, amino acid residues at positions 464-519, R551, L552, T554, I555, L556, and W558 of SEQ ID NO: 1.

2. The PE of claim 1, wherein the FCS comprises residues 274-284 of SEQ ID NO: 1, and wherein the optional substitution of an amino acid within one or more B-cell epitopes of SEQ ID NO: 1 is a substitution of alanine, glycine, serine, or glutamine for amino acid residue E282 of SEQ ID NO: 1.

3. The PE of claim 1, wherein m is 1 and $R^1$ comprises residues 285-293 of SEQ ID NO: 1, wherein the optional substitution of an amino acid within one or more B-cell epitopes of SEQ ID NO: 1 is a substitution of alanine, glycine, serine, or glutamine for amino acid residue E285 and/or P290 of SEQ ID NO: 1.

4. The PE of claim 1, wherein n is 1 and $R^3$ comprises residues 306-394 of SEQ ID NO: 1, wherein the optional substitution of an amino acid within one or more B-cell epitopes of SEQ ID NO: 1 is a substitution of alanine, glycine, serine, or glutamine for one or more of amino acid residues R313, N314, P319, D324, E327, E331, and Q332 of SEQ ID NO: 1.

5. The PE of claim 1, wherein the PE functional domain III comprises residues 395-613 of SEQ ID NO: 1 with a substitution of amino acid residue D463, and wherein the optional substitution of an amino acid within one or more B-cell epitopes of SEQ ID NO: 1 is a substitution of alanine, glycine, serine, or glutamine for one or more of amino acid residues D403, D406, R412, R427, E431, R432, R458, D461, R467, Y481, R490, R505, R513, L516, E522, R538, E548, R551, R576, K590, Q592, and L597 of SEQ ID NO: 1 and/or a substitution of valine, leucine, or isoleucine in place of amino acid residue R490 of SEQ ID NO: 1.

6. The PE of claim 1, wherein m, n, and p are 0.

7. The PE of claim 1, wherein amino acid residue D463 is substituted with alanine, glycine, serine, or glutamine.

8. The PE of claim 1, wherein amino acid residue D463 is substituted with alanine.

9. A pharmaceutical composition comprising (a) the PE of claim 1, and (b) a pharmaceutically acceptable carrier.

10. A chimeric molecule comprising (a) a targeting moiety conjugated or fused to (b) the PE of claim 1.

11. The chimeric molecule of claim 10, wherein the targeting moiety is a monoclonal antibody or an antigen binding portion thereof.

12. The chimeric molecule of claim 11, wherein the monoclonal antibody specifically binds to a cell surface marker selected from the group consisting of cluster of differentiation (CD) 19, CD21, CD22, CD25, CD30, CD33, CD79b, transferrin receptor, epidermal growth factor (EGF) receptor, mesothelin, cadherin, and Lewis Y.

13. The chimeric molecule of claim 11, wherein the targeting moiety is selected from the group consisting of B3, RFB4, SS, SS1, MN, MB, HN1, HN2, HB21, MORAb-009, and antigen binding portions thereof.

14. The chimeric molecule of claim 10, wherein the targeting moiety is the antigen binding portion of HA22.

15. A method of inhibiting the growth of a target cell, wherein the method comprises contacting the cell with the PE of claim 1 in an amount effective to inhibit growth of the target cell.

16. The method of claim 15, wherein the target cell is a cancer cell.

17. A method of producing the PE of claim 1, wherein the method comprises (a) recombinantly expressing the PE, and (b) purifying the PE.

18. A method of producing the chimeric molecule of claim 10, wherein the method comprises (a) recombinantly expressing the chimeric molecule, and (b) purifying the chimeric molecule.

* * * * *

```
                          SEQUENCE LISTING

<160> NUMBER OF SEQ ID NOS: 203

<210> SEQ ID NO 1
<211> LENGTH: 613
<212> TYPE: PRT
<213> ORGANISM: Pseudomonas aeruginosa

<400> SEQUENCE: 1

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
```

```
                245                 250                 255
Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Asn Ala Asp Val Val
        355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Ser Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610

<210> SEQ ID NO 2
<211> LENGTH: 12
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<222> LOCATION: (1)..(1)
<223> OTHER INFORMATION: Xaa at position 1 is Leu, Ala, Gly, Ser, or Gln
<220> FEATURE:
<221> NAME/KEY: MISC_FEATURE
<222> LOCATION: (4)..(4)
<223> OTHER INFORMATION: Xaa at position 4 is Leu, Ala, Gly, Ser, or Gln
<220> FEATURE:
<221> NAME/KEY: MISC_FEATURE
<222> LOCATION: (5)..(5)
<223> OTHER INFORMATION: Xaa at position 5 is Tyr, Ala, Gly, Ser, or Gln
<220> FEATURE:
<221> NAME/KEY: MISC_FEATURE
<222> LOCATION: (6)..(6)
<223> OTHER INFORMATION: Xaa at position 6 is Leu, Ala, Gly, Ser, or Gln
<220> FEATURE:
<221> NAME/KEY: MISC_FEATURE
<222> LOCATION: (9)..(9)
<223> OTHER INFORMATION: Xaa at position 9 is Arg, Ala, Gly, Ser, or Glu

<400> SEQUENCE: 2

Xaa Val Ala Xaa Xaa Xaa Ala Ala Xaa Leu Ser Trp
1               5                   10

<210> SEQ ID NO 3
<211> LENGTH: 12
<212> TYPE: PRT
<213> ORGANISM: Pseudomonas aeruginosa

<400> SEQUENCE: 3

Leu Val Ala Leu Tyr Leu Ala Ala Arg Leu Ser Trp
1               5                   10

<210> SEQ ID NO 4
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc
<222> LOCATION: (2)..(2)
<223> OTHER INFORMATION: Xaa at position 2 is any amino acid
<220> FEATURE:
<221> NAME/KEY: misc
<222> LOCATION: (3)..(3)
<223> OTHER INFORMATION: Xaa at position 3 is Arg or Lys

<400> SEQUENCE: 4

Arg Xaa Xaa Arg
1

<210> SEQ ID NO 5
<211> LENGTH: 4
<212> TYPE: PRT
<213> ORGANISM: Artificial Sequence
<220> FEATURE:
<223> OTHER INFORMATION: Synthetic

<400> SEQUENCE: 5

Lys Asp Glu Leu
1

<210> SEQ ID NO 6
<211> LENGTH: 5
<212> TYPE: PRT
<213> ORGANISM: Pseudomonas aeruginosa

<400> SEQUENCE: 6

Arg Glu Asp Leu Lys
```

```
<210> SEQ ID NO 7
<211> LENGTH: 4
<212> TYPE: PRT
<213> ORGANISM: Pseudomonas aeruginosa

<400> SEQUENCE: 7

Arg Glu Asp Leu
1

<210> SEQ ID NO 8
<211> LENGTH: 11
<212> TYPE: PRT
<213> ORGANISM: Pseudomonas aeruginosa

<400> SEQUENCE: 8

Arg His Arg Gln Pro Arg Gly Trp Glu Gln Leu
1               5                   10

<210> SEQ ID NO 9
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid

<400> SEQUENCE: 9

Arg Xaa Xaa Arg
1

<210> SEQ ID NO 10
<211> LENGTH: 4
<212> TYPE: PRT
<213> ORGANISM: Artificial Sequence
<220> FEATURE:
<223> OTHER INFORMATION: Synthetic

<400> SEQUENCE: 10

Arg Lys Lys Arg
1

<210> SEQ ID NO 11
<211> LENGTH: 4
<212> TYPE: PRT
<213> ORGANISM: Artificial Sequence
<220> FEATURE:
<223> OTHER INFORMATION: Synthetic

<400> SEQUENCE: 11

Arg Arg Arg Arg
1

<210> SEQ ID NO 12
<211> LENGTH: 4
<212> TYPE: PRT
<213> ORGANISM: Artificial Sequence
<220> FEATURE:
<223> OTHER INFORMATION: Synthetic

<400> SEQUENCE: 12

Arg Lys Ala Arg
1
```

```
<210> SEQ ID NO 13
<211> LENGTH: 6
<212> TYPE: PRT
<213> ORGANISM: Artificial Sequence
<220> FEATURE:
<223> OTHER INFORMATION: Synthetic

<400> SEQUENCE: 13

Ser Arg Val Ala Arg Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic

<400> SEQUENCE: 14

Thr Ser Ser Arg Lys Arg Arg Phe Trp
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic

<400> SEQUENCE: 15

Ala Ser Arg Arg Lys Ala Arg Ser Trp
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic

<400> SEQUENCE: 16

Arg Arg Val Lys Lys Arg Phe Trp
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic

<400> SEQUENCE: 17

Arg Asn Val Val Arg Arg Asp Trp
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Thr Arg Ala Val Arg Arg Arg Ser Trp
1               5
```

```
<210> SEQ ID NO 19
<211> LENGTH: 4
<212> TYPE: PRT
<213> ORGANISM: Artificial Sequence
<220> FEATURE:
<223> OTHER INFORMATION: Synthetic

<400> SEQUENCE: 19

Arg Gln Pro Arg
1

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Arg His Arg Gln Pro Arg Gly Trp
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic

<400> SEQUENCE: 21

Arg His Arg Gln Pro Arg Gly Trp Glu
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic

<400> SEQUENCE: 22

His Arg Gln Pro Arg Gly Trp Glu Gln
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic

<400> SEQUENCE: 23

Arg Gln Pro Arg Gly Trp Glu
1               5

<210> SEQ ID NO 24
<211> LENGTH: 11
<212> TYPE: PRT
<213> ORGANISM: Artificial Sequence
<220> FEATURE:
<223> OTHER INFORMATION: Synthetic

<400> SEQUENCE: 24

Arg His Arg Ser Lys Arg Gly Trp Glu Gln Leu
1               5                   10
```

<210> SEQ ID NO 25
<211> LENGTH: 4
<212> TYPE: PRT
<213> ORGANISM: Artificial Sequence
<220> FEATURE:
<223> OTHER INFORMATION: Synthetic

<400> SEQUENCE: 25

Arg Ser Lys Arg
1

<210> SEQ ID NO 26
<211> LENGTH: 8
<212> TYPE: PRT
<213> ORGANISM: Artificial Sequence
<220> FEATURE:
<223> OTHER INFORMATION: Synthetic

<400> SEQUENCE: 26

Arg His Arg Ser Lys Arg Gly Trp
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic

<400> SEQUENCE: 27

His Arg Ser Lys Arg Gly Trp Glu
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic

<400> SEQUENCE: 28

Arg Ser Lys Arg Gly Trp Glu Gln Leu
1               5

<210> SEQ ID NO 29
<211> LENGTH: 10
<212> TYPE: PRT
<213> ORGANISM: Artificial Sequence
<220> FEATURE:
<223> OTHER INFORMATION: Synthetic

<400> SEQUENCE: 29

His Arg Ser Lys Arg Gly Trp Glu Gln Leu
1               5                   10

<210> SEQ ID NO 30
<211> LENGTH: 6
<212> TYPE: PRT
<213> ORGANISM: Artificial Sequence
<220> FEATURE:
<223> OTHER INFORMATION: Synthetic

<400> SEQUENCE: 30

Arg His Arg Ser Lys Arg
1               5

<210> SEQ ID NO 31

```
<211> LENGTH: 15
<212> TYPE: PRT
<213> ORGANISM: Pseudomonas aeruginosa

<400> SEQUENCE: 31

Pro Glu Gly Gly Ser Leu Ala Ala Leu Thr Ala His Gln Ala Cys
1               5                   10                  15

<210> SEQ ID NO 32
<211> LENGTH: 15
<212> TYPE: PRT
<213> ORGANISM: Pseudomonas aeruginosa

<400> SEQUENCE: 32

Ser Leu Ala Ala Leu Thr Ala His Gln Ala Cys His Leu Pro Leu
1               5                   10                  15

<210> SEQ ID NO 33
<211> LENGTH: 15
<212> TYPE: PRT
<213> ORGANISM: Pseudomonas aeruginosa

<400> SEQUENCE: 33

Ala Leu Thr Ala His Gln Ala Cys His Leu Pro Leu Glu Thr Phe
1               5                   10                  15

<210> SEQ ID NO 34
<211> LENGTH: 15
<212> TYPE: PRT
<213> ORGANISM: Pseudomonas aeruginosa

<400> SEQUENCE: 34

Ala His Gln Ala Cys His Leu Pro Leu Glu Thr Phe Thr Arg His
1               5                   10                  15

<210> SEQ ID NO 35
<211> LENGTH: 15
<212> TYPE: PRT
<213> ORGANISM: Pseudomonas aeruginosa

<400> SEQUENCE: 35

Ala Cys His Leu Pro Leu Glu Thr Phe Thr Arg His Arg Gln Pro
1               5                   10                  15

<210> SEQ ID NO 36
<211> LENGTH: 15
<212> TYPE: PRT
<213> ORGANISM: Pseudomonas aeruginosa

<400> SEQUENCE: 36

Leu Pro Leu Glu Thr Phe Thr Arg His Arg Gln Pro Arg Gly Trp
1               5                   10                  15

<210> SEQ ID NO 37
<211> LENGTH: 15
<212> TYPE: PRT
<213> ORGANISM: Pseudomonas aeruginosa

<400> SEQUENCE: 37

Glu Thr Phe Thr Arg His Arg Gln Pro Arg Gly Trp Glu Gln Leu
1               5                   10                  15

<210> SEQ ID NO 38
<211> LENGTH: 15
<212> TYPE: PRT
```

<213> ORGANISM: Pseudomonas aeruginosa

<400> SEQUENCE: 38

Thr Arg His Arg Gln Pro Arg Gly Trp Glu Gln Leu Glu Gln Cys
1               5                   10                  15

<210> SEQ ID NO 39
<211> LENGTH: 15
<212> TYPE: PRT
<213> ORGANISM: Pseudomonas aeruginosa

<400> SEQUENCE: 39

Arg Gln Pro Arg Gly Trp Glu Gln Leu Glu Gln Cys Gly Tyr Pro
1               5                   10                  15

<210> SEQ ID NO 40
<211> LENGTH: 15
<212> TYPE: PRT
<213> ORGANISM: Pseudomonas aeruginosa

<400> SEQUENCE: 40

Arg Gly Trp Glu Gln Leu Glu Gln Cys Gly Tyr Pro Val Gln Arg
1               5                   10                  15

<210> SEQ ID NO 41
<211> LENGTH: 15
<212> TYPE: PRT
<213> ORGANISM: Pseudomonas aeruginosa

<400> SEQUENCE: 41

Glu Gln Leu Glu Gln Cys Gly Tyr Pro Val Gln Arg Leu Val Ala
1               5                   10                  15

<210> SEQ ID NO 42
<211> LENGTH: 15
<212> TYPE: PRT
<213> ORGANISM: Pseudomonas aeruginosa

<400> SEQUENCE: 42

Glu Gln Cys Gly Tyr Pro Val Gln Arg Leu Val Ala Leu Tyr Leu
1               5                   10                  15

<210> SEQ ID NO 43
<211> LENGTH: 15
<212> TYPE: PRT
<213> ORGANISM: Pseudomonas aeruginosa

<400> SEQUENCE: 43

Gly Tyr Pro Val Gln Arg Leu Val Ala Leu Tyr Leu Ala Ala Arg
1               5                   10                  15

<210> SEQ ID NO 44
<211> LENGTH: 15
<212> TYPE: PRT
<213> ORGANISM: Pseudomonas aeruginosa

<400> SEQUENCE: 44

Val Gln Arg Leu Val Ala Leu Tyr Leu Ala Ala Arg Leu Ser Trp
1               5                   10                  15

<210> SEQ ID NO 45
<211> LENGTH: 15
<212> TYPE: PRT
<213> ORGANISM: Pseudomonas aeruginosa

```
<400> SEQUENCE: 45

Leu Val Ala Leu Tyr Leu Ala Ala Arg Leu Ser Trp Asn Gln Val
1               5                   10                  15

<210> SEQ ID NO 46
<211> LENGTH: 15
<212> TYPE: PRT
<213> ORGANISM: Pseudomonas aeruginosa

<400> SEQUENCE: 46

Leu Tyr Leu Ala Ala Arg Leu Ser Trp Asn Gln Val Asp Gln Val
1               5                   10                  15

<210> SEQ ID NO 47
<211> LENGTH: 15
<212> TYPE: PRT
<213> ORGANISM: Pseudomonas aeruginosa

<400> SEQUENCE: 47

Ala Ala Arg Leu Ser Trp Asn Gln Val Asp Gln Val Ile Arg Asn
1               5                   10                  15

<210> SEQ ID NO 48
<211> LENGTH: 15
<212> TYPE: PRT
<213> ORGANISM: Pseudomonas aeruginosa

<400> SEQUENCE: 48

Leu Ser Trp Asn Gln Val Asp Gln Val Ile Arg Asn Ala Leu Ala
1               5                   10                  15

<210> SEQ ID NO 49
<211> LENGTH: 15
<212> TYPE: PRT
<213> ORGANISM: Pseudomonas aeruginosa

<400> SEQUENCE: 49

Asn Gln Val Asp Gln Val Ile Arg Asn Ala Leu Ala Ser Pro Gly
1               5                   10                  15

<210> SEQ ID NO 50
<211> LENGTH: 15
<212> TYPE: PRT
<213> ORGANISM: Pseudomonas aeruginosa

<400> SEQUENCE: 50

Asp Gln Val Ile Arg Asn Ala Leu Ala Ser Pro Gly Ser Gly Gly
1               5                   10                  15

<210> SEQ ID NO 51
<211> LENGTH: 15
<212> TYPE: PRT
<213> ORGANISM: Pseudomonas aeruginosa

<400> SEQUENCE: 51

Ile Arg Asn Ala Leu Ala Ser Pro Gly Ser Gly Gly Asp Leu Gly
1               5                   10                  15

<210> SEQ ID NO 52
<211> LENGTH: 15
<212> TYPE: PRT
<213> ORGANISM: Pseudomonas aeruginosa

<400> SEQUENCE: 52
```

```
Ala Leu Ala Ser Pro Gly Ser Gly Gly Asp Leu Gly Glu Ala Ile
1               5                   10                  15
```

<210> SEQ ID NO 53
<211> LENGTH: 15
<212> TYPE: PRT
<213> ORGANISM: Pseudomonas aeruginosa

<400> SEQUENCE: 53

```
Ser Pro Gly Ser Gly Gly Asp Leu Gly Glu Ala Ile Arg Glu Gln
1               5                   10                  15
```

<210> SEQ ID NO 54
<211> LENGTH: 15
<212> TYPE: PRT
<213> ORGANISM: Pseudomonas aeruginosa

<400> SEQUENCE: 54

```
Ser Gly Gly Asp Leu Gly Glu Ala Ile Arg Glu Gln Pro Glu Gln
1               5                   10                  15
```

<210> SEQ ID NO 55
<211> LENGTH: 15
<212> TYPE: PRT
<213> ORGANISM: Pseudomonas aeruginosa

<400> SEQUENCE: 55

```
Asp Leu Gly Glu Ala Ile Arg Glu Gln Pro Glu Gln Ala Arg Leu
1               5                   10                  15
```

<210> SEQ ID NO 56
<211> LENGTH: 15
<212> TYPE: PRT
<213> ORGANISM: Pseudomonas aeruginosa

<400> SEQUENCE: 56

```
Glu Ala Ile Arg Glu Gln Pro Glu Gln Ala Arg Leu Ala Leu Thr
1               5                   10                  15
```

<210> SEQ ID NO 57
<211> LENGTH: 15
<212> TYPE: PRT
<213> ORGANISM: Pseudomonas aeruginosa

<400> SEQUENCE: 57

```
Arg Glu Gln Pro Glu Gln Ala Arg Leu Ala Leu Thr Leu Ala Ala
1               5                   10                  15
```

<210> SEQ ID NO 58
<211> LENGTH: 15
<212> TYPE: PRT
<213> ORGANISM: Pseudomonas aeruginosa

<400> SEQUENCE: 58

```
Pro Glu Gln Ala Arg Leu Ala Leu Thr Leu Ala Ala Ala Glu Ser
1               5                   10                  15
```

<210> SEQ ID NO 59
<211> LENGTH: 15
<212> TYPE: PRT
<213> ORGANISM: Pseudomonas aeruginosa

<400> SEQUENCE: 59

```
Ala Arg Leu Ala Leu Thr Leu Ala Ala Ala Glu Ser Glu Arg Phe
1               5                   10                  15
```

<210> SEQ ID NO 60
<211> LENGTH: 15
<212> TYPE: PRT
<213> ORGANISM: Pseudomonas aeruginosa

<400> SEQUENCE: 60

Ala Leu Thr Leu Ala Ala Ala Glu Ser Glu Arg Phe Val Arg Gln
1               5                   10                  15

<210> SEQ ID NO 61
<211> LENGTH: 15
<212> TYPE: PRT
<213> ORGANISM: Pseudomonas aeruginosa

<400> SEQUENCE: 61

Leu Ala Ala Ala Glu Ser Glu Arg Phe Val Arg Gln Gly Thr Gly
1               5                   10                  15

<210> SEQ ID NO 62
<211> LENGTH: 15
<212> TYPE: PRT
<213> ORGANISM: Pseudomonas aeruginosa

<400> SEQUENCE: 62

Ala Glu Ser Glu Arg Phe Val Arg Gln Gly Thr Gly Asn Asp Glu
1               5                   10                  15

<210> SEQ ID NO 63
<211> LENGTH: 15
<212> TYPE: PRT
<213> ORGANISM: Pseudomonas aeruginosa

<400> SEQUENCE: 63

Glu Arg Phe Val Arg Gln Gly Thr Gly Asn Asp Glu Ala Gly Ala
1               5                   10                  15

<210> SEQ ID NO 64
<211> LENGTH: 15
<212> TYPE: PRT
<213> ORGANISM: Pseudomonas aeruginosa

<400> SEQUENCE: 64

Val Arg Gln Gly Thr Gly Asn Asp Glu Ala Gly Ala Ala Asn Gly
1               5                   10                  15

<210> SEQ ID NO 65
<211> LENGTH: 15
<212> TYPE: PRT
<213> ORGANISM: Pseudomonas aeruginosa

<400> SEQUENCE: 65

Gly Thr Gly Asn Asp Glu Ala Gly Ala Ala Asn Gly Pro Ala Asp
1               5                   10                  15

<210> SEQ ID NO 66
<211> LENGTH: 15
<212> TYPE: PRT
<213> ORGANISM: Pseudomonas aeruginosa

<400> SEQUENCE: 66

Asn Asp Glu Ala Gly Ala Ala Asn Gly Pro Ala Asp Ser Gly Asp
1               5                   10                  15

<210> SEQ ID NO 67
<211> LENGTH: 15
<212> TYPE: PRT
<213> ORGANISM: Pseudomonas aeruginosa

<400> SEQUENCE: 67

Ala Gly Ala Ala Asn Gly Pro Ala Asp Ser Gly Asp Ala Leu Leu
1               5                   10                  15

<210> SEQ ID NO 68
<211> LENGTH: 15
<212> TYPE: PRT
<213> ORGANISM: Pseudomonas aeruginosa

<400> SEQUENCE: 68

Ala Asn Gly Pro Ala Asp Ser Gly Asp Ala Leu Leu Glu Arg Asn
1               5                   10                  15

<210> SEQ ID NO 69
<211> LENGTH: 15
<212> TYPE: PRT
<213> ORGANISM: Pseudomonas aeruginosa

<400> SEQUENCE: 69

Pro Ala Asp Ser Gly Asp Ala Leu Leu Glu Arg Asn Tyr Pro Thr
1               5                   10                  15

<210> SEQ ID NO 70
<211> LENGTH: 15
<212> TYPE: PRT
<213> ORGANISM: Pseudomonas aeruginosa

<400> SEQUENCE: 70

Ser Gly Asp Ala Leu Leu Glu Arg Asn Tyr Pro Thr Gly Ala Glu
1               5                   10                  15

<210> SEQ ID NO 71
<211> LENGTH: 15
<212> TYPE: PRT
<213> ORGANISM: Pseudomonas aeruginosa

<400> SEQUENCE: 71

Ala Leu Leu Glu Arg Asn Tyr Pro Thr Gly Ala Glu Phe Leu Gly
1               5                   10                  15

<210> SEQ ID NO 72
<211> LENGTH: 15
<212> TYPE: PRT
<213> ORGANISM: Pseudomonas aeruginosa

<400> SEQUENCE: 72

Glu Arg Asn Tyr Pro Thr Gly Ala Glu Phe Leu Gly Asp Gly Gly
1               5                   10                  15

<210> SEQ ID NO 73
<211> LENGTH: 15
<212> TYPE: PRT
<213> ORGANISM: Pseudomonas aeruginosa

<400> SEQUENCE: 73

Tyr Pro Thr Gly Ala Glu Phe Leu Gly Asp Gly Gly Asp Val Ser
1               5                   10                  15

<210> SEQ ID NO 74
<211> LENGTH: 15

<212> TYPE: PRT
<213> ORGANISM: Pseudomonas aeruginosa

<400> SEQUENCE: 74

Gly Ala Glu Phe Leu Gly Asp Gly Asp Val Ser Phe Ser Thr
1               5                   10                  15

<210> SEQ ID NO 75
<211> LENGTH: 15
<212> TYPE: PRT
<213> ORGANISM: Pseudomonas aeruginosa

<400> SEQUENCE: 75

Phe Leu Gly Asp Gly Gly Asp Val Ser Phe Ser Thr Arg Gly Thr
1               5                   10                  15

<210> SEQ ID NO 76
<211> LENGTH: 15
<212> TYPE: PRT
<213> ORGANISM: Pseudomonas aeruginosa

<400> SEQUENCE: 76

Asp Gly Gly Asp Val Ser Phe Ser Thr Arg Gly Thr Gln Asn Trp
1               5                   10                  15

<210> SEQ ID NO 77
<211> LENGTH: 15
<212> TYPE: PRT
<213> ORGANISM: Pseudomonas aeruginosa

<400> SEQUENCE: 77

Asp Val Ser Phe Ser Thr Arg Gly Thr Gln Asn Trp Thr Val Glu
1               5                   10                  15

<210> SEQ ID NO 78
<211> LENGTH: 15
<212> TYPE: PRT
<213> ORGANISM: Pseudomonas aeruginosa

<400> SEQUENCE: 78

Phe Ser Thr Arg Gly Thr Gln Asn Trp Thr Val Glu Arg Leu Leu
1               5                   10                  15

<210> SEQ ID NO 79
<211> LENGTH: 15
<212> TYPE: PRT
<213> ORGANISM: Pseudomonas aeruginosa

<400> SEQUENCE: 79

Arg Gly Thr Gln Asn Trp Thr Val Glu Arg Leu Leu Gln Ala His
1               5                   10                  15

<210> SEQ ID NO 80
<211> LENGTH: 15
<212> TYPE: PRT
<213> ORGANISM: Pseudomonas aeruginosa

<400> SEQUENCE: 80

Gln Asn Trp Thr Val Glu Arg Leu Leu Gln Ala His Arg Gln Leu
1               5                   10                  15

<210> SEQ ID NO 81
<211> LENGTH: 15
<212> TYPE: PRT
<213> ORGANISM: Pseudomonas aeruginosa

<400> SEQUENCE: 81

Thr Val Glu Arg Leu Leu Gln Ala His Arg Gln Leu Glu Glu Arg
1               5                   10                  15

<210> SEQ ID NO 82
<211> LENGTH: 15
<212> TYPE: PRT
<213> ORGANISM: Pseudomonas aeruginosa

<400> SEQUENCE: 82

Arg Leu Leu Gln Ala His Arg Gln Leu Glu Glu Arg Gly Tyr Val
1               5                   10                  15

<210> SEQ ID NO 83
<211> LENGTH: 15
<212> TYPE: PRT
<213> ORGANISM: Pseudomonas aeruginosa

<400> SEQUENCE: 83

Gln Ala His Arg Gln Leu Glu Glu Arg Gly Tyr Val Phe Val Gly
1               5                   10                  15

<210> SEQ ID NO 84
<211> LENGTH: 15
<212> TYPE: PRT
<213> ORGANISM: Pseudomonas aeruginosa

<400> SEQUENCE: 84

Arg Gln Leu Glu Glu Arg Gly Tyr Val Phe Val Gly Tyr His Gly
1               5                   10                  15

<210> SEQ ID NO 85
<211> LENGTH: 15
<212> TYPE: PRT
<213> ORGANISM: Pseudomonas aeruginosa

<400> SEQUENCE: 85

Glu Glu Arg Gly Tyr Val Phe Val Gly Tyr His Gly Thr Phe Leu
1               5                   10                  15

<210> SEQ ID NO 86
<211> LENGTH: 15
<212> TYPE: PRT
<213> ORGANISM: Pseudomonas aeruginosa

<400> SEQUENCE: 86

Gly Tyr Val Phe Val Gly Tyr His Gly Thr Phe Leu Glu Ala Ala
1               5                   10                  15

<210> SEQ ID NO 87
<211> LENGTH: 15
<212> TYPE: PRT
<213> ORGANISM: Pseudomonas aeruginosa

<400> SEQUENCE: 87

Phe Val Gly Tyr His Gly Thr Phe Leu Glu Ala Ala Gln Ser Ile
1               5                   10                  15

<210> SEQ ID NO 88
<211> LENGTH: 15
<212> TYPE: PRT
<213> ORGANISM: Pseudomonas aeruginosa

<400> SEQUENCE: 88

```
Tyr His Gly Thr Phe Leu Glu Ala Ala Gln Ser Ile Val Phe Gly
1               5                   10                  15

<210> SEQ ID NO 89
<211> LENGTH: 15
<212> TYPE: PRT
<213> ORGANISM: Pseudomonas aeruginosa

<400> SEQUENCE: 89

Thr Phe Leu Glu Ala Ala Gln Ser Ile Val Phe Gly Gly Val Arg
1               5                   10                  15

<210> SEQ ID NO 90
<211> LENGTH: 15
<212> TYPE: PRT
<213> ORGANISM: Pseudomonas aeruginosa

<400> SEQUENCE: 90

Glu Ala Ala Gln Ser Ile Val Phe Gly Gly Val Arg Ala Arg Ser
1               5                   10                  15

<210> SEQ ID NO 91
<211> LENGTH: 15
<212> TYPE: PRT
<213> ORGANISM: Pseudomonas aeruginosa

<400> SEQUENCE: 91

Gln Ser Ile Val Phe Gly Gly Val Arg Ala Arg Ser Gln Asp Leu
1               5                   10                  15

<210> SEQ ID NO 92
<211> LENGTH: 15
<212> TYPE: PRT
<213> ORGANISM: Pseudomonas aeruginosa

<400> SEQUENCE: 92

Val Phe Gly Gly Val Arg Ala Arg Ser Gln Asp Leu Asp Ala Ile
1               5                   10                  15

<210> SEQ ID NO 93
<211> LENGTH: 15
<212> TYPE: PRT
<213> ORGANISM: Pseudomonas aeruginosa

<400> SEQUENCE: 93

Gly Val Arg Ala Arg Ser Gln Asp Leu Asp Ala Ile Trp Arg Gly
1               5                   10                  15

<210> SEQ ID NO 94
<211> LENGTH: 15
<212> TYPE: PRT
<213> ORGANISM: Pseudomonas aeruginosa

<400> SEQUENCE: 94

Ala Arg Ser Gln Asp Leu Asp Ala Ile Trp Arg Gly Phe Tyr Ile
1               5                   10                  15

<210> SEQ ID NO 95
<211> LENGTH: 15
<212> TYPE: PRT
<213> ORGANISM: Pseudomonas aeruginosa

<400> SEQUENCE: 95

Gln Asp Leu Asp Ala Ile Trp Arg Gly Phe Tyr Ile Ala Gly Asp
```

<210> SEQ ID NO 96
<211> LENGTH: 15
<212> TYPE: PRT
<213> ORGANISM: Pseudomonas aeruginosa

<400> SEQUENCE: 96

Asp Ala Ile Trp Arg Gly Phe Tyr Ile Ala Gly Asp Pro Ala Leu
1               5                   10                  15

<210> SEQ ID NO 97
<211> LENGTH: 15
<212> TYPE: PRT
<213> ORGANISM: Pseudomonas aeruginosa

<400> SEQUENCE: 97

Trp Arg Gly Phe Tyr Ile Ala Gly Asp Pro Ala Leu Ala Tyr Gly
1               5                   10                  15

<210> SEQ ID NO 98
<211> LENGTH: 15
<212> TYPE: PRT
<213> ORGANISM: Pseudomonas aeruginosa

<400> SEQUENCE: 98

Phe Tyr Ile Ala Gly Asp Pro Ala Leu Ala Tyr Gly Tyr Ala Gln
1               5                   10                  15

<210> SEQ ID NO 99
<211> LENGTH: 15
<212> TYPE: PRT
<213> ORGANISM: Pseudomonas aeruginosa

<400> SEQUENCE: 99

Ala Gly Asp Pro Ala Leu Ala Tyr Gly Tyr Ala Gln Asp Gln Glu
1               5                   10                  15

<210> SEQ ID NO 100
<211> LENGTH: 15
<212> TYPE: PRT
<213> ORGANISM: Pseudomonas aeruginosa

<400> SEQUENCE: 100

Pro Ala Leu Ala Tyr Gly Tyr Ala Gln Asp Gln Glu Pro Asp Ala
1               5                   10                  15

<210> SEQ ID NO 101
<211> LENGTH: 15
<212> TYPE: PRT
<213> ORGANISM: Pseudomonas aeruginosa

<400> SEQUENCE: 101

Ala Tyr Gly Tyr Ala Gln Asp Gln Glu Pro Asp Ala Arg Gly Arg
1               5                   10                  15

<210> SEQ ID NO 102
<211> LENGTH: 15
<212> TYPE: PRT
<213> ORGANISM: Pseudomonas aeruginosa

<400> SEQUENCE: 102

Tyr Ala Gln Asp Gln Glu Pro Asp Ala Arg Gly Arg Ile Arg Asn
1               5                   10                  15

-continued

<210> SEQ ID NO 103
<211> LENGTH: 15
<212> TYPE: PRT
<213> ORGANISM: Pseudomonas aeruginosa

<400> SEQUENCE: 103

Asp Gln Glu Pro Asp Ala Arg Gly Arg Ile Arg Asn Gly Ala Leu
1               5                   10                  15

<210> SEQ ID NO 104
<211> LENGTH: 15
<212> TYPE: PRT
<213> ORGANISM: Pseudomonas aeruginosa

<400> SEQUENCE: 104

Pro Asp Ala Arg Gly Arg Ile Arg Asn Gly Ala Leu Leu Arg Val
1               5                   10                  15

<210> SEQ ID NO 105
<211> LENGTH: 15
<212> TYPE: PRT
<213> ORGANISM: Pseudomonas aeruginosa

<400> SEQUENCE: 105

Arg Gly Arg Ile Arg Asn Gly Ala Leu Leu Arg Val Tyr Val Pro
1               5                   10                  15

<210> SEQ ID NO 106
<211> LENGTH: 15
<212> TYPE: PRT
<213> ORGANISM: Pseudomonas aeruginosa

<400> SEQUENCE: 106

Ile Arg Asn Gly Ala Leu Leu Arg Val Tyr Val Pro Arg Ser Ser
1               5                   10                  15

<210> SEQ ID NO 107
<211> LENGTH: 15
<212> TYPE: PRT
<213> ORGANISM: Pseudomonas aeruginosa

<400> SEQUENCE: 107

Gly Ala Leu Leu Arg Val Tyr Val Pro Arg Ser Ser Leu Pro Gly
1               5                   10                  15

<210> SEQ ID NO 108
<211> LENGTH: 15
<212> TYPE: PRT
<213> ORGANISM: Pseudomonas aeruginosa

<400> SEQUENCE: 108

Leu Arg Val Tyr Val Pro Arg Ser Ser Leu Pro Gly Phe Tyr Arg
1               5                   10                  15

<210> SEQ ID NO 109
<211> LENGTH: 15
<212> TYPE: PRT
<213> ORGANISM: Pseudomonas aeruginosa

<400> SEQUENCE: 109

Tyr Val Pro Arg Ser Ser Leu Pro Gly Phe Tyr Arg Thr Ser Leu
1               5                   10                  15

<210> SEQ ID NO 110

```
<211> LENGTH: 15
<212> TYPE: PRT
<213> ORGANISM: Pseudomonas aeruginosa

<400> SEQUENCE: 110

Arg Ser Ser Leu Pro Gly Phe Tyr Arg Thr Ser Leu Thr Leu Ala
1               5                   10                  15

<210> SEQ ID NO 111
<211> LENGTH: 15
<212> TYPE: PRT
<213> ORGANISM: Pseudomonas aeruginosa

<400> SEQUENCE: 111

Leu Pro Gly Phe Tyr Arg Thr Ser Leu Thr Leu Ala Ala Pro Glu
1               5                   10                  15

<210> SEQ ID NO 112
<211> LENGTH: 15
<212> TYPE: PRT
<213> ORGANISM: Pseudomonas aeruginosa

<400> SEQUENCE: 112

Phe Tyr Arg Thr Ser Leu Thr Leu Ala Ala Pro Glu Ala Ala Gly
1               5                   10                  15

<210> SEQ ID NO 113
<211> LENGTH: 15
<212> TYPE: PRT
<213> ORGANISM: Pseudomonas aeruginosa

<400> SEQUENCE: 113

Thr Ser Leu Thr Leu Ala Ala Pro Glu Ala Ala Gly Glu Val Glu
1               5                   10                  15

<210> SEQ ID NO 114
<211> LENGTH: 15
<212> TYPE: PRT
<213> ORGANISM: Pseudomonas aeruginosa

<400> SEQUENCE: 114

Thr Leu Ala Ala Pro Glu Ala Ala Gly Glu Val Glu Arg Leu Ile
1               5                   10                  15

<210> SEQ ID NO 115
<211> LENGTH: 15
<212> TYPE: PRT
<213> ORGANISM: Pseudomonas aeruginosa

<400> SEQUENCE: 115

Ala Pro Glu Ala Ala Gly Glu Val Glu Arg Leu Ile Gly His Pro
1               5                   10                  15

<210> SEQ ID NO 116
<211> LENGTH: 15
<212> TYPE: PRT
<213> ORGANISM: Pseudomonas aeruginosa

<400> SEQUENCE: 116

Ala Ala Gly Glu Val Glu Arg Leu Ile Gly His Pro Leu Pro Leu
1               5                   10                  15

<210> SEQ ID NO 117
<211> LENGTH: 15
<212> TYPE: PRT
```

<213> ORGANISM: Pseudomonas aeruginosa

<400> SEQUENCE: 117

Glu Val Glu Arg Leu Ile Gly His Pro Leu Pro Leu Arg Leu Asp
1               5                   10                  15

<210> SEQ ID NO 118
<211> LENGTH: 15
<212> TYPE: PRT
<213> ORGANISM: Pseudomonas aeruginosa

<400> SEQUENCE: 118

Arg Leu Ile Gly His Pro Leu Pro Leu Arg Leu Asp Ala Ile Thr
1               5                   10                  15

<210> SEQ ID NO 119
<211> LENGTH: 15
<212> TYPE: PRT
<213> ORGANISM: Pseudomonas aeruginosa

<400> SEQUENCE: 119

Gly His Pro Leu Pro Leu Arg Leu Asp Ala Ile Thr Gly Pro Glu
1               5                   10                  15

<210> SEQ ID NO 120
<211> LENGTH: 15
<212> TYPE: PRT
<213> ORGANISM: Pseudomonas aeruginosa

<400> SEQUENCE: 120

Leu Pro Leu Arg Leu Asp Ala Ile Thr Gly Pro Glu Glu Glu Gly
1               5                   10                  15

<210> SEQ ID NO 121
<211> LENGTH: 15
<212> TYPE: PRT
<213> ORGANISM: Pseudomonas aeruginosa

<400> SEQUENCE: 121

Arg Leu Asp Ala Ile Thr Gly Pro Glu Glu Glu Gly Gly Arg Leu
1               5                   10                  15

<210> SEQ ID NO 122
<211> LENGTH: 15
<212> TYPE: PRT
<213> ORGANISM: Pseudomonas aeruginosa

<400> SEQUENCE: 122

Ala Ile Thr Gly Pro Glu Glu Glu Gly Gly Arg Leu Glu Thr Ile
1               5                   10                  15

<210> SEQ ID NO 123
<211> LENGTH: 15
<212> TYPE: PRT
<213> ORGANISM: Pseudomonas aeruginosa

<400> SEQUENCE: 123

Gly Pro Glu Glu Glu Gly Gly Arg Leu Glu Thr Ile Leu Gly Trp
1               5                   10                  15

<210> SEQ ID NO 124
<211> LENGTH: 15
<212> TYPE: PRT
<213> ORGANISM: Pseudomonas aeruginosa -continued

<400> SEQUENCE: 124

Glu Glu Gly Gly Arg Leu Glu Thr Ile Leu Gly Trp Pro Leu Ala
1               5                   10                  15

<210> SEQ ID NO 125
<211> LENGTH: 15
<212> TYPE: PRT
<213> ORGANISM: Pseudomonas aeruginosa

<400> SEQUENCE: 125

Gly Arg Leu Glu Thr Ile Leu Gly Trp Pro Leu Ala Glu Arg Thr
1               5                   10                  15

<210> SEQ ID NO 126
<211> LENGTH: 15
<212> TYPE: PRT
<213> ORGANISM: Pseudomonas aeruginosa

<400> SEQUENCE: 126

Glu Thr Ile Leu Gly Trp Pro Leu Ala Glu Arg Thr Val Val Ile
1               5                   10                  15

<210> SEQ ID NO 127
<211> LENGTH: 15
<212> TYPE: PRT
<213> ORGANISM: Pseudomonas aeruginosa

<400> SEQUENCE: 127

Leu Gly Trp Pro Leu Ala Glu Arg Thr Val Val Ile Pro Ser Ala
1               5                   10                  15

<210> SEQ ID NO 128
<211> LENGTH: 15
<212> TYPE: PRT
<213> ORGANISM: Pseudomonas aeruginosa

<400> SEQUENCE: 128

Pro Leu Ala Glu Arg Thr Val Val Ile Pro Ser Ala Ile Pro Thr
1               5                   10                  15

<210> SEQ ID NO 129
<211> LENGTH: 15
<212> TYPE: PRT
<213> ORGANISM: Pseudomonas aeruginosa

<400> SEQUENCE: 129

Glu Arg Thr Val Val Ile Pro Ser Ala Ile Pro Thr Asp Pro Arg
1               5                   10                  15

<210> SEQ ID NO 130
<211> LENGTH: 15
<212> TYPE: PRT
<213> ORGANISM: Pseudomonas aeruginosa

<400> SEQUENCE: 130

Val Val Ile Pro Ser Ala Ile Pro Thr Asp Pro Arg Asn Val Gly
1               5                   10                  15

<210> SEQ ID NO 131
<211> LENGTH: 15
<212> TYPE: PRT
<213> ORGANISM: Pseudomonas aeruginosa

<400> SEQUENCE: 131

Pro Ser Ala Ile Pro Thr Asp Pro Arg Asn Val Gly Gly Asp Leu
1               5                   10                  15

<210> SEQ ID NO 132
<211> LENGTH: 15
<212> TYPE: PRT
<213> ORGANISM: Pseudomonas aeruginosa

<400> SEQUENCE: 132

Ile Pro Thr Asp Pro Arg Asn Val Gly Gly Asp Leu Asp Pro Ser
1               5                   10                  15

<210> SEQ ID NO 133
<211> LENGTH: 15
<212> TYPE: PRT
<213> ORGANISM: Pseudomonas aeruginosa

<400> SEQUENCE: 133

Asp Pro Arg Asn Val Gly Gly Asp Leu Asp Pro Ser Ser Ile Pro
1               5                   10                  15

<210> SEQ ID NO 134
<211> LENGTH: 15
<212> TYPE: PRT
<213> ORGANISM: Pseudomonas aeruginosa

<400> SEQUENCE: 134

Asn Val Gly Gly Asp Leu Asp Pro Ser Ser Ile Pro Asp Lys Glu
1               5                   10                  15

<210> SEQ ID NO 135
<211> LENGTH: 15
<212> TYPE: PRT
<213> ORGANISM: Pseudomonas aeruginosa

<400> SEQUENCE: 135

Gly Asp Leu Asp Pro Ser Ser Ile Pro Asp Lys Glu Gln Ala Ile
1               5                   10                  15

<210> SEQ ID NO 136
<211> LENGTH: 15
<212> TYPE: PRT
<213> ORGANISM: Pseudomonas aeruginosa

<400> SEQUENCE: 136

Asp Pro Ser Ser Ile Pro Asp Lys Glu Gln Ala Ile Ser Ala Leu
1               5                   10                  15

<210> SEQ ID NO 137
<211> LENGTH: 15
<212> TYPE: PRT
<213> ORGANISM: Pseudomonas aeruginosa

<400> SEQUENCE: 137

Ser Ile Pro Asp Lys Glu Gln Ala Ile Ser Ala Leu Pro Asp Tyr
1               5                   10                  15

<210> SEQ ID NO 138
<211> LENGTH: 15
<212> TYPE: PRT
<213> ORGANISM: Pseudomonas aeruginosa

<400> SEQUENCE: 138

Asp Lys Glu Gln Ala Ile Ser Ala Leu Pro Asp Tyr Ala Ser Gln
1               5                   10                  15

<210> SEQ ID NO 139
<211> LENGTH: 15
<212> TYPE: PRT
<213> ORGANISM: Pseudomonas aeruginosa

<400> SEQUENCE: 139

Gln Ala Ile Ser Ala Leu Pro Asp Tyr Ala Ser Gln Pro Gly Lys
1               5                   10                  15

<210> SEQ ID NO 140
<211> LENGTH: 15
<212> TYPE: PRT
<213> ORGANISM: Pseudomonas aeruginosa

<400> SEQUENCE: 140

Ser Ala Leu Pro Asp Tyr Ala Ser Gln Pro Gly Lys Pro Pro Arg
1               5                   10                  15

<210> SEQ ID NO 141
<211> LENGTH: 15
<212> TYPE: PRT
<213> ORGANISM: Pseudomonas aeruginosa

<400> SEQUENCE: 141

Pro Asp Tyr Ala Ser Gln Pro Gly Lys Pro Pro Arg Glu Asp Leu
1               5                   10                  15

<210> SEQ ID NO 142
<211> LENGTH: 219
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: Xaa at position 12 is Ala, Gly, Ser, Gln, or
      Asp
<220> FEATURE:
<221> NAME/KEY: MISC_FEATURE
<222> LOCATION: (38)..(38)
<223> OTHER INFORMATION: Xaa at position 38 is Ala, Gly, Ser, Gln, or
      Arg
<220> FEATURE:
<221> NAME/KEY: MISC_FEATURE
<222> LOCATION: (73)..(73)
<223> OTHER INFORMATION: Xaa at position 73 is Ala, Gly, Ser, Gln, or
      Arg
<220> FEATURE:
<221> NAME/KEY: MISC_FEATURE
<222> LOCATION: (96)..(96)
<223> OTHER INFORMATION: Xaa at position 96 is Ala, Gly, Ser, Gln, or
      Arg
<220> FEATURE:
<221> NAME/KEY: MISC_FEATURE
<222> LOCATION: (119)..(119)
<223> OTHER INFORMATION: Xaa at position 119 is Ala, Gly, Ser, Gln, or
      Arg
<220> FEATURE:
<221> NAME/KEY: MISC_FEATURE
<222> LOCATION: (154)..(154)
<223> OTHER INFORMATION: Xaa at position 154 is Ala, Gly, Ser, Gln, or
      Glu
<220> FEATURE:
<221> NAME/KEY: MISC_FEATURE
<222> LOCATION: (196)..(196)
<223> OTHER INFORMATION: Xaa at position 196 is Ala, Gly, Ser, Gln, or
      Lys
<220> FEATURE:
<221> NAME/KEY: MISC_FEATURE
<222> LOCATION: (198)..(198)

<223> OTHER INFORMATION: Xaa at position 198 is Ala, Gly, Ser, or Gln

<400> SEQUENCE: 142

```
Pro Thr Gly Ala Glu Phe Leu Gly Asp Gly Xaa Val Ser Phe Ser
1               5                   10                  15

Thr Arg Gly Thr Gln Asn Trp Thr Val Glu Arg Leu Leu Gln Ala His
            20                  25                  30

Arg Gln Leu Glu Glu Xaa Gly Tyr Val Phe Val Gly Tyr His Gly Thr
        35                  40                  45

Phe Leu Glu Ala Ala Gln Ser Ile Val Phe Gly Gly Val Arg Ala Arg
    50                  55                  60

Ser Gln Asp Leu Asp Ala Ile Trp Xaa Gly Phe Tyr Ile Ala Gly Asp
65                  70                  75                  80

Pro Ala Leu Ala Tyr Gly Tyr Ala Gln Asp Gln Glu Pro Asp Ala Xaa
                85                  90                  95

Gly Arg Ile Arg Asn Gly Ala Leu Leu Arg Val Tyr Val Pro Arg Ser
            100                 105                 110

Ser Leu Pro Gly Phe Tyr Xaa Thr Ser Leu Thr Leu Ala Ala Pro Glu
        115                 120                 125

Ala Ala Gly Glu Val Glu Arg Leu Ile Gly His Pro Leu Pro Leu Arg
    130                 135                 140

Leu Asp Ala Ile Thr Gly Pro Glu Glu Xaa Gly Gly Arg Leu Glu Thr
145                 150                 155                 160

Ile Leu Gly Trp Pro Leu Ala Glu Arg Thr Val Val Ile Pro Ser Ala
                165                 170                 175

Ile Pro Thr Asp Pro Arg Asn Val Gly Gly Asp Leu Asp Pro Ser Ser
            180                 185                 190

Ile Pro Asp Xaa Glu Xaa Ala Ile Ser Ala Leu Pro Asp Tyr Ala Ser
        195                 200                 205

Gln Pro Gly Lys Pro Pro Arg Glu Asp Leu Lys
    210                 215
```

<210> SEQ ID NO 143
<211> LENGTH: 219
<212> TYPE: PRT
<213> ORGANISM: Artificial Sequence
<220> FEATURE:
<223> OTHER INFORMATION: Synthetic

<400> SEQUENCE: 143

```
Pro Thr Gly Ala Glu Phe Leu Gly Asp Gly Gly Ala Val Ser Phe Ser
1               5                   10                  15

Thr Arg Gly Thr Gln Asn Trp Thr Val Glu Arg Leu Leu Gln Ala His
            20                  25                  30

Arg Gln Leu Glu Glu Gly Gly Tyr Val Phe Val Gly Tyr His Gly Thr
        35                  40                  45

Phe Leu Glu Ala Ala Gln Ser Ile Val Phe Gly Gly Val Arg Ala Arg
    50                  55                  60

Ser Gln Asp Leu Asp Ala Ile Trp Ala Gly Phe Tyr Ile Ala Gly Asp
65                  70                  75                  80

Pro Ala Leu Ala Tyr Gly Tyr Ala Gln Asp Gln Glu Pro Asp Ala Ala
                85                  90                  95

Gly Arg Ile Arg Asn Gly Ala Leu Leu Arg Val Tyr Val Pro Arg Ser
            100                 105                 110

Ser Leu Pro Gly Phe Tyr Ala Thr Ser Leu Thr Leu Ala Ala Pro Glu
        115                 120                 125
```

Ala Ala Gly Glu Val Glu Arg Leu Ile Gly His Pro Leu Pro Leu Arg
            130                 135                 140

Leu Asp Ala Ile Thr Gly Pro Glu Glu Ser Gly Arg Leu Glu Thr
145                 150                 155                 160

Ile Leu Gly Trp Pro Leu Ala Glu Arg Thr Val Val Ile Pro Ser Ala
                165                 170                 175

Ile Pro Thr Asp Pro Arg Asn Val Gly Gly Asp Leu Asp Pro Ser Ser
                180                 185                 190

Ile Pro Asp Ser Glu Ala Ala Ile Ser Ala Leu Pro Asp Tyr Ala Ser
            195                 200                 205

Gln Pro Gly Lys Pro Pro Arg Glu Asp Leu Lys
            210                 215

<210> SEQ ID NO 144
<211> LENGTH: 345
<212> TYPE: PRT
<213> ORGANISM: Artificial Sequence
<220> FEATURE:
<223> OTHER INFORMATION: Synthetic

<400> SEQUENCE: 144

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
                20                  25                  30

Glu Gln Cys Gly Tyr Pro Val Gln Arg Leu Val Ala Leu Tyr Leu Ala
            35                  40                  45

Ala Arg Leu Ser Trp Asn Gln Val Asp Gln Val Ile Arg Asn Ala Leu
50                  55                  60

Ala Ser Pro Gly Ser Gly Gly Asp Leu Gly Glu Ala Ile Arg Glu Gln
65                  70                  75                  80

Pro Glu Gln Ala Arg Leu Ala Leu Thr Leu Ala Ala Glu Ser Glu
                85                  90                  95

Arg Phe Val Arg Gln Gly Thr Gly Asn Asp Glu Ala Gly Ala Ala Asn
                100                 105                 110

Gly Pro Ala Asp Ser Gly Asp Ala Leu Leu Glu Arg Asn Tyr Pro Thr
            115                 120                 125

Gly Ala Glu Phe Leu Gly Asp Gly Gly Asp Val Ser Phe Ser Thr Arg
        130                 135                 140

Gly Thr Gln Asn Trp Thr Val Glu Arg Leu Leu Gln Ala His Arg Gln
145                 150                 155                 160

Leu Glu Glu Arg Gly Tyr Val Phe Val Gly Tyr His Gly Thr Phe Leu
                165                 170                 175

Glu Ala Ala Gln Ser Ile Val Phe Gly Val Arg Ala Arg Ser Gln
            180                 185                 190

Asp Leu Asp Ala Ile Trp Arg Gly Phe Tyr Ile Ala Gly Asp Pro Ala
            195                 200                 205

Leu Ala Tyr Gly Tyr Ala Gln Asp Gln Glu Pro Asp Ala Arg Gly Arg
        210                 215                 220

Ile Arg Asn Gly Ala Leu Leu Arg Val Tyr Val Pro Arg Ser Ser Leu
225                 230                 235                 240

Pro Gly Phe Tyr Arg Thr Ser Leu Thr Leu Ala Ala Pro Glu Ala Ala
                245                 250                 255

Gly Glu Val Glu Arg Leu Ile Gly His Pro Leu Pro Leu Arg Leu Asp
                260                 265                 270

Ala Ile Thr Gly Pro Glu Glu Gly Gly Arg Leu Glu Thr Ile Leu
            275                 280                 285

Gly Trp Pro Leu Ala Glu Arg Thr Val Val Ile Pro Ser Ala Ile Pro
290                 295                 300

Thr Asp Pro Arg Asn Val Gly Gly Asp Leu Asp Pro Ser Ser Ile Pro
305                 310                 315                 320

Asp Lys Glu Gln Ala Ile Ser Ala Leu Pro Asp Tyr Ala Ser Gln Pro
                325                 330                 335

Gly Lys Pro Pro Arg Glu Asp Leu Lys
            340                 345

<210> SEQ ID NO 145
<211> LENGTH: 15
<212> TYPE: PRT
<213> ORGANISM: Artificial Sequence
<220> FEATURE:
<223> OTHER INFORMATION: Synthetic

<400> SEQUENCE: 145

Leu Val Ala Leu Tyr Leu Ala Ala Ala Leu Ser Trp Asn Gln Val
1               5                   10                  15

<210> SEQ ID NO 146
<211> LENGTH: 24
<212> TYPE: DNA
<213> ORGANISM: Artificial Sequence
<220> FEATURE:
<223> OTHER INFORMATION: Synthetic

<400> SEQUENCE: 146
gtccaccttg gtgttgctgg gctt                                          24

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147
agactctccc ctgttgaagc tctt                                          24

<210> SEQ ID NO 148
<211> LENGTH: 23
<212> TYPE: DNA
<213> ORGANISM: Artificial Sequence
<220> FEATURE:
<223> OTHER INFORMATION: Synthetic

<400> SEQUENCE: 148
caggtgcagc tggtgcagtc tgg                                           23

<210> SEQ ID NO 149
<211> LENGTH: 23
<212> TYPE: DNA
<213> ORGANISM: Artificial Sequence
<220> FEATURE:
<223> OTHER INFORMATION: Synthetic

<400> SEQUENCE: 149
caggtcaact taagggagtc tgg                                           23

<210> SEQ ID NO 150

```
<211> LENGTH: 23
<212> TYPE: DNA
<213> ORGANISM: Artificial Sequence
<220> FEATURE:
<223> OTHER INFORMATION: Synthetic

<400> SEQUENCE: 150
gaggtgcagc tggtggagtc tgg                                          23

<210> SEQ ID NO 151
<211> LENGTH: 23
<212> TYPE: DNA
<213> ORGANISM: Artificial Sequence
<220> FEATURE:
<223> OTHER INFORMATION: Synthetic

<400> SEQUENCE: 151
caggtgcagc tgcaggagtc ggg                                          23

<210> SEQ ID NO 152
<211> LENGTH: 23
<212> TYPE: DNA
<213> ORGANISM: Artificial Sequence
<220> FEATURE:
<223> OTHER INFORMATION: Synthetic

<400> SEQUENCE: 152
gaggtgcagc tgttgcagtc tgc                                          23

<210> SEQ ID NO 153
<211> LENGTH: 23
<212> TYPE: DNA
<213> ORGANISM: Artificial Sequence
<220> FEATURE:
<223> OTHER INFORMATION: Synthetic

<400> SEQUENCE: 153
caggtacagc tgcagcagtc agg                                          23

<210> SEQ ID NO 154
<211> LENGTH: 23
<212> TYPE: DNA
<213> ORGANISM: Artificial Sequence
<220> FEATURE:
<223> OTHER INFORMATION: Synthetic

<400> SEQUENCE: 154
gacatccaga tgacccagtc tcc                                          23

<210> SEQ ID NO 155
<211> LENGTH: 23
<212> TYPE: DNA
<213> ORGANISM: Artificial Sequence
<220> FEATURE:
<223> OTHER INFORMATION: Synthetic

<400> SEQUENCE: 155
gatgttgtga tgactcagtc tcc                                          23

<210> SEQ ID NO 156
<211> LENGTH: 23
<212> TYPE: DNA
<213> ORGANISM: Artificial Sequence
<220> FEATURE:
<223> OTHER INFORMATION: Synthetic

<400> SEQUENCE: 156
```
gaaattgtgt tgacgcagtc tcc                                         23

<210> SEQ ID NO 157
<211> LENGTH: 23
<212> TYPE: DNA
<213> ORGANISM: Artificial Sequence
<220> FEATURE:
<223> OTHER INFORMATION: Synthetic

<400> SEQUENCE: 157
gacatcgtga tgacccagtc tcc                                         23

<210> SEQ ID NO 158
<211> LENGTH: 23
<212> TYPE: DNA
<213> ORGANISM: Artificial Sequence
<220> FEATURE:
<223> OTHER INFORMATION: Synthetic

<400> SEQUENCE: 158
gaaacgacac tcacgcagtc tcc                                         23

<210> SEQ ID NO 159
<211> LENGTH: 23
<212> TYPE: DNA
<213> ORGANISM: Artificial Sequence
<220> FEATURE:
<223> OTHER INFORMATION: Synthetic

<400> SEQUENCE: 159
gaaattgtgc tgactcagtc tcc                                         23

<210> SEQ ID NO 160
<211> LENGTH: 41
<212> TYPE: DNA
<213> ORGANISM: Artificial Sequence
<220> FEATURE:
<223> OTHER INFORMATION: Synthetic

<400> SEQUENCE: 160
gcccagccgg ccatggccca ggtgcagctg gtgcagtctg g                     41

<210> SEQ ID NO 161
<211> LENGTH: 41
<212> TYPE: DNA
<213> ORGANISM: Artificial Sequence
<220> FEATURE:
<223> OTHER INFORMATION: Synthetic

<400> SEQUENCE: 161
gcccagccgg ccatggccca ggtcaactta agggagtctg g                     41

<210> SEQ ID NO 162
<211> LENGTH: 41
<212> TYPE: DNA
<213> ORGANISM: Artificial Sequence
<220> FEATURE:
<223> OTHER INFORMATION: Synthetic

<400> SEQUENCE: 162
gcccagccgg ccatggccga ggtgcagctg gtggagtctg g                     41

<210> SEQ ID NO 163
<211> LENGTH: 40
<212> TYPE: DNA

<213> ORGANISM: Artificial Sequence
<220> FEATURE:
<223> OTHER INFORMATION: Synthetic

<400> SEQUENCE: 163
cccagccggc catggcccag gtgcagctgc aggagtcggg           40

<210> SEQ ID NO 164
<211> LENGTH: 41
<212> TYPE: DNA
<213> ORGANISM: Artificial Sequence
<220> FEATURE:
<223> OTHER INFORMATION: Synthetic

<400> SEQUENCE: 164
gcccagccgg ccatggccga ggtgcagctg ttgcagtctg c          41

<210> SEQ ID NO 165
<211> LENGTH: 41
<212> TYPE: DNA
<213> ORGANISM: Artificial Sequence
<220> FEATURE:
<223> OTHER INFORMATION: Synthetic

<400> SEQUENCE: 165
gcccagccgg ccatggccca ggtacagctg cagcagtcag g          41

<210> SEQ ID NO 166
<211> LENGTH: 60
<212> TYPE: DNA
<213> ORGANISM: Artificial Sequence
<220> FEATURE:
<223> OTHER INFORMATION: Synthetic

<400> SEQUENCE: 166
acctccagat ccgccaccac cggatccgcc tccgcctgag gagacggtga ccagggtgcc    60

<210> SEQ ID NO 167
<211> LENGTH: 60
<212> TYPE: DNA
<213> ORGANISM: Artificial Sequence
<220> FEATURE:
<223> OTHER INFORMATION: Synthetic

<400> SEQUENCE: 167
acctccagat ccgccaccac cggatccgcc tccgcctgaa gagacggtga ccattgtccc    60

<210> SEQ ID NO 168
<211> LENGTH: 60
<212> TYPE: DNA
<213> ORGANISM: Artificial Sequence
<220> FEATURE:
<223> OTHER INFORMATION: Synthetic

<400> SEQUENCE: 168
acctccagat ccgccaccac cggatccgcc tccgcctgag gagacggtga ccagggttcc    60

<210> SEQ ID NO 169
<211> LENGTH: 60
<212> TYPE: DNA
<213> ORGANISM: Artificial Sequence
<220> FEATURE:
<223> OTHER INFORMATION: Synthetic

<400> SEQUENCE: 169
acctccagat ccgccaccac cggatccgcc tccgcctgag gagacggtga ccgtggtccc    60

```
<210> SEQ ID NO 170
<211> LENGTH: 59
<212> TYPE: DNA
<213> ORGANISM: Artificial Sequence
<220> FEATURE:
<223> OTHER INFORMATION: Synthetic

<400> SEQUENCE: 170
ggatccggtg gtggcggatc tggaggtggc ggaagcgaca tccagatgac ccagtctcc      59

<210> SEQ ID NO 171
<211> LENGTH: 59
<212> TYPE: DNA
<213> ORGANISM: Artificial Sequence
<220> FEATURE:
<223> OTHER INFORMATION: Synthetic

<400> SEQUENCE: 171
ggatccggtg gtggcggatc tggaggtggc ggaagcgatg ttgtgatgac tcagtctcc      59

<210> SEQ ID NO 172
<211> LENGTH: 59
<212> TYPE: DNA
<213> ORGANISM: Artificial Sequence
<220> FEATURE:
<223> OTHER INFORMATION: Synthetic

<400> SEQUENCE: 172
ggatccggtg gtggcggatc tggaggtggc ggaagcgaaa ttgtgttgac gcagtctcc      59

<210> SEQ ID NO 173
<211> LENGTH: 59
<212> TYPE: DNA
<213> ORGANISM: Artificial Sequence
<220> FEATURE:
<223> OTHER INFORMATION: Synthetic

<400> SEQUENCE: 173
ggatccggtg gtggcggatc tggaggtggc ggaagcgaca tcgtgatgac ccagtctcc      59

<210> SEQ ID NO 174
<211> LENGTH: 59
<212> TYPE: DNA
<213> ORGANISM: Artificial Sequence
<220> FEATURE:
<223> OTHER INFORMATION: Synthetic

<400> SEQUENCE: 174
ggatccggtg gtggcggatc tggaggtggc ggaagcgaaa cgacactcac gcagtctcc      59

<210> SEQ ID NO 175
<211> LENGTH: 59
<212> TYPE: DNA
<213> ORGANISM: Artificial Sequence
<220> FEATURE:
<223> OTHER INFORMATION: Synthetic

<400> SEQUENCE: 175
ggatccggtg gtggcggatc tggaggtggc ggaagcgaaa ttgtgctgac tcagtctcc      59

<210> SEQ ID NO 176
<211> LENGTH: 48
<212> TYPE: DNA
<213> ORGANISM: Artificial Sequence
<220> FEATURE:
```

```
<223> OTHER INFORMATION: Synthetic

<400> SEQUENCE: 176
gagtcattct cgacttgcgg ccgcacgttt gatttccacc ttggtccc        48

<210> SEQ ID NO 177
<211> LENGTH: 48
<212> TYPE: DNA
<213> ORGANISM: Artificial Sequence
<220> FEATURE:
<223> OTHER INFORMATION: Synthetic

<400> SEQUENCE: 177
gagtcattct cgacttgcgg ccgcacgttt gatctccagc ttggtccc        48

<210> SEQ ID NO 178
<211> LENGTH: 48
<212> TYPE: DNA
<213> ORGANISM: Artificial Sequence
<220> FEATURE:
<223> OTHER INFORMATION: Synthetic

<400> SEQUENCE: 178
gagtcattct cgacttgcgg ccgcacgttt gatatccact ttggtccc        48

<210> SEQ ID NO 179
<211> LENGTH: 48
<212> TYPE: DNA
<213> ORGANISM: Artificial Sequence
<220> FEATURE:
<223> OTHER INFORMATION: Synthetic

<400> SEQUENCE: 179
gagtcattct cgacttgcgg ccgcacgttt gatctccacc ttggtccc        48

<210> SEQ ID NO 180
<211> LENGTH: 48
<212> TYPE: DNA
<213> ORGANISM: Artificial Sequence
<220> FEATURE:
<223> OTHER INFORMATION: Synthetic

<400> SEQUENCE: 180
gagtcattct cgacttgcgg ccgcacgttt aatctccagt cgtgtccc        48

<210> SEQ ID NO 181
<211> LENGTH: 45
<212> TYPE: DNA
<213> ORGANISM: Artificial Sequence
<220> FEATURE:
<223> OTHER INFORMATION: Synthetic

<400> SEQUENCE: 181
gcttccgcca cctccagatc cgccaccacc ggatccgcct ccgcc           45

<210> SEQ ID NO 182
<211> LENGTH: 45
<212> TYPE: DNA
<213> ORGANISM: Artificial Sequence
<220> FEATURE:
<223> OTHER INFORMATION: Synthetic

<400> SEQUENCE: 182
ggcggaggcg gatccggtgg tggcggatct ggaggtggcg gaagc           45
```

```
<210> SEQ ID NO 183
<211> LENGTH: 33
<212> TYPE: DNA
<213> ORGANISM: Artificial Sequence
<220> FEATURE:
<223> OTHER INFORMATION: Synthetic

<400> SEQUENCE: 183
gtcctcgcaa ctgcggccca gccggccatg gcc                              33

<210> SEQ ID NO 184
<211> LENGTH: 24
<212> TYPE: DNA
<213> ORGANISM: Artificial Sequence
<220> FEATURE:
<223> OTHER INFORMATION: Synthetic

<400> SEQUENCE: 184
gagtcattct cgacttgcgg ccgc                                        24

<210> SEQ ID NO 185
<211> LENGTH: 18
<212> TYPE: DNA
<213> ORGANISM: Artificial Sequence
<220> FEATURE:
<223> OTHER INFORMATION: Synthetic

<400> SEQUENCE: 185
gcccagccgg ccatggcc                                               18

<210> SEQ ID NO 186
<211> LENGTH: 36
<212> TYPE: DNA
<213> ORGANISM: Artificial Sequence
<220> FEATURE:
<223> OTHER INFORMATION: Synthetic

<400> SEQUENCE: 186
acctccagat ccgccaccac cggatccgcc tccgcc                           36

<210> SEQ ID NO 187
<211> LENGTH: 36
<212> TYPE: DNA
<213> ORGANISM: Artificial Sequence
<220> FEATURE:
<223> OTHER INFORMATION: Synthetic

<400> SEQUENCE: 187
ggatccggtg gtggcggatc tggaggtggc ggaagc                           36

<210> SEQ ID NO 188
<211> LENGTH: 30
<212> TYPE: PRT
<213> ORGANISM: Pseudomonas aeruginosa

<400> SEQUENCE: 188

Glu Gln Leu Glu Gln Cys Gly Tyr Pro Val Gln Arg Leu Val Ala Leu
1               5                   10                  15

Tyr Leu Ala Ala Arg Leu Ser Trp Asn Gln Val Asp Gln Val
            20                  25                  30

<210> SEQ ID NO 189
<211> LENGTH: 42
<212> TYPE: PRT
<213> ORGANISM: Pseudomonas aeruginosa
```

-continued

<400> SEQUENCE: 189

Tyr Ala Gln Asp Gln Glu Pro Asp Ala Arg Gly Arg Ile Arg Asn Gly
1               5                   10                  15

Ala Leu Leu Arg Val Tyr Val Pro Arg Ser Ser Leu Pro Gly Phe Tyr
            20                  25                  30

Arg Thr Ser Leu Thr Leu Ala Ala Pro Glu
        35                  40

<210> SEQ ID NO 190
<211> LENGTH: 12
<212> TYPE: PRT
<213> ORGANISM: Pseudomonas aeruginosa

<400> SEQUENCE: 190

Ile Arg Asn Gly Ala Leu Leu Arg Val Tyr Val Pro
1               5                   10

<210> SEQ ID NO 191
<211> LENGTH: 12
<212> TYPE: PRT
<213> ORGANISM: Pseudomonas aeruginosa

<400> SEQUENCE: 191

Leu Arg Val Tyr Val Pro Arg Ser Ser Leu Pro Gly
1               5                   10

<210> SEQ ID NO 192
<211> LENGTH: 12
<212> TYPE: PRT
<213> ORGANISM: Pseudomonas aeruginosa

<400> SEQUENCE: 192

Phe Tyr Ile Ala Gly Asp Pro Ala Leu Ala Tyr Gly
1               5                   10

<210> SEQ ID NO 193
<211> LENGTH: 12
<212> TYPE: PRT
<213> ORGANISM: Pseudomonas aeruginosa

<400> SEQUENCE: 193

Arg Leu Leu Gln Ala His Arg Gln Leu Glu Glu Arg
1               5                   10

<210> SEQ ID NO 194
<211> LENGTH: 12
<212> TYPE: PRT
<213> ORGANISM: Pseudomonas aeruginosa

<400> SEQUENCE: 194

Glu Glu Gly Gly Arg Leu Glu Thr Ile Leu Gly Trp
1               5                   10

<210> SEQ ID NO 195
<211> LENGTH: 12
<212> TYPE: PRT
<213> ORGANISM: Pseudomonas aeruginosa

<400> SEQUENCE: 195

Gly Arg Leu Glu Thr Ile Leu Gly Trp Pro Leu Ala
1               5                   10

<210> SEQ ID NO 196

```
<211> LENGTH: 12
<212> TYPE: PRT
<213> ORGANISM: Pseudomonas aeruginosa

<400> SEQUENCE: 196

Phe Val Gly Tyr His Gly Thr Phe Leu Glu Ala Ala
1               5                   10

<210> SEQ ID NO 197
<211> LENGTH: 12
<212> TYPE: PRT
<213> ORGANISM: Pseudomonas aeruginosa

<400> SEQUENCE: 197

Tyr His Gly Thr Phe Leu Glu Ala Ala Gln Ser Ile
1               5                   10

<210> SEQ ID NO 198
<211> LENGTH: 18
<212> TYPE: PRT
<213> ORGANISM: Pseudomonas aeruginosa

<400> SEQUENCE: 198

Gly Pro Glu Glu Glu Gly Gly Arg Leu Glu Thr Ile Leu Gly Trp Pro
1               5                   10                  15

Leu Ala

<210> SEQ ID NO 199
<211> LENGTH: 18
<212> TYPE: PRT
<213> ORGANISM: Pseudomonas aeruginosa

<400> SEQUENCE: 199

Phe Val Gly Tyr His Gly Thr Phe Leu Glu Ala Ala Gln Ser Ile Val
1               5                   10                  15

Phe Gly

<210> SEQ ID NO 200
<211> LENGTH: 12
<212> TYPE: PRT
<213> ORGANISM: Pseudomonas aeruginosa

<400> SEQUENCE: 200

Arg Gln Pro Arg Gly Trp Glu Gln Leu Glu Gln Cys
1               5                   10

<210> SEQ ID NO 201
<211> LENGTH: 18
<212> TYPE: PRT
<213> ORGANISM: Pseudomonas aeruginosa

<400> SEQUENCE: 201

Ile Arg Asn Gly Ala Leu Leu Arg Val Tyr Val Pro Arg Ser Ser Leu
1               5                   10                  15

Pro Gly

<210> SEQ ID NO 202
<211> LENGTH: 14
<212> TYPE: PRT
<213> ORGANISM: Pseudomonas aeruginosa

<400> SEQUENCE: 202

Glu Glu Gly Gly Arg Leu Glu Thr Ile Leu Gly Trp Pro Leu
```

-continued

```
1               5                   10

<210> SEQ ID NO 203
<211> LENGTH: 18
<212> TYPE: PRT
<213> ORGANISM: Pseudomonas aeruginosa

<400> SEQUENCE: 203

Pro Asp Ala Arg Gly Arg Ile Arg Asn Gly Ala Leu Leu Arg Val Tyr
1               5                   10                  15

Val Pro
```